United States Patent
Merali et al.

(10) Patent No.: US 9,585,380 B2
(45) Date of Patent: Mar. 7, 2017

(54) SSAT MRNA TRANSLATION REPRESSION AND ACTIVATION

(75) Inventors: Salim Merali, Bryn Mawr, PA (US); Oscar Mauricio Perez Leal, Barranquilla (CO); Magid Abou-Gharbia, Exton, PA (US); Wayne E. Childers, New Hope, PA (US)

(73) Assignee: TEMPLE UNIVERSITY—Of The Commonwealth System of Higher Education, Philadelphia, PA (US)

( * ) Notice: Subject to any disclaimer, the term of this patent is extended or adjusted under 35 U.S.C. 154(b) by 110 days.

(21) Appl. No.: 14/342,063

(22) PCT Filed: Aug. 31, 2012

(86) PCT No.: PCT/US2012/053445
§ 371 (c)(1),
(2), (4) Date: Mar. 24, 2014

(87) PCT Pub. No.: WO2013/033597
PCT Pub. Date: Mar. 7, 2013

(65) Prior Publication Data
US 2014/0234827 A1 Aug. 21, 2014

Related U.S. Application Data

(60) Provisional application No. 61/530,498, filed on Sep. 2, 2011, provisional application No. 61/680,497, filed on Aug. 7, 2012.

(51) Int. Cl.
*A01N 1/02* (2006.01)
*C12N 9/10* (2006.01)
*G01N 33/50* (2006.01)
*C12Q 1/68* (2006.01)

(52) U.S. Cl.
CPC ......... *A01N 1/0226* (2013.01); *C12N 9/1029* (2013.01); *C12Q 1/6802* (2013.01); *C12Y 201/03* (2013.01); *G01N 33/502* (2013.01); *G01N 2500/04* (2013.01)

(58) Field of Classification Search
None
See application file for complete search history.

(56) References Cited

U.S. PATENT DOCUMENTS

| 5,498,522 A | 3/1996 | Porter |
| 5,840,559 A * | 11/1998 | Hillman ............... C12N 9/1029 435/193 |
| 6,017,529 A | 1/2000 | Hillman |
| 6,342,534 B1 | 1/2002 | Bergeron, Jr. |
| 6,413,775 B1 | 7/2002 | Porter et al. |
| 6,727,066 B2 | 4/2004 | Kaser |
| 6,811,967 B2 | 11/2004 | Sitar et al. |
| 2009/0061488 A1 | 3/2009 | Liao et al. |
| 2009/0252714 A1 | 10/2009 | Sahin et al. |
| 2011/0081708 A1 | 4/2011 | Liu et al. |

OTHER PUBLICATIONS

Babbar et al., "Tumor Necrosis Factor Induces Spermidine/Spermine N1-Acetyltransferase through Nuclear Factor B in Non-small Cell Lung Cancer Cells", 2006, J Biol Chem. 281:24182-24192.
Bewley et al., "Structures of wild-type and mutant human spermidine/spermine te-acetyltransferase, a potential therapeutic drug target", 2006, PNAS 103:2063-2068.
Butcher et al., "Polyamine-dependent Regulation of Spermidine-Spermine N1-Acetyltransferase mRNA Translation", 2007, J Biol Chem. 282:28530-28539.
Casero et al, "Isolation and Characterization of a cDNA Clone That Codes for Human spermidine/spermine N1-acetyltransferase", 1991, J Bio Chem. 266:810-814.
Coleman et al, "Targeted expression of spermidine/spermine N1-acetyltransferase increases susceptibility to chemically induced skin carcinogenesis", 2002, Carcinogenesis 23:359-364.
Fogel-Petrovi et al, "Structural Basis for Differential Induction of Spermidine/Spermine N1-Acetyltransferase Activity by Novel Spermine Analogs", 1997, Molecular Pharmacology 52:69-74.
Fogel-Petrovi et al., Effects of Polyamine Analogs, and inhibitors of Protein Synthesis on Spermidine/Spermine N1-Acetyltransferase Gene Expression, 1996, Biochemisttry 35:14436-14444 (Abstract only).
Ivanov et al., "A profusion of upstream open reading frame mechanisma in polyamine-responsive translational regulation", 2010, NAR 38:353-359.
Kee et al., 2004, "Activated polyamine catabolism depletes acetyl-CoA pools and suppresses prostate tumor growth in TRAMP mice", J Biol Chem. Sep. 17, 2004;279(38):40076-83. Epub Jul. 13, 2004.
Kozak, "An analysis of 5'-noncoding sequences from 699 vertebrate messenger RNAs", 1987, NAR 15:8125-8148.
PMID 20031193, abstracting—Marverti et al., "Spermidine/Spermine N1-Acetyltransferase modulation by novel folate cycle inhibitors in cisplatin-sensitive and -resistant human ovarian cancer cell lines", 2010, Gynecologic Oncology 117:202-210.
Murray-Stewart et al., "Spermidine/spermine N1-acetyltransferase (SSAT) activity in human small-cell lung carcinoma cells following transfection with a genomic SSAT construct", 2003, Biochem J 373:629-634.

(Continued)

*Primary Examiner* — Nashaat Nashed
(74) *Attorney, Agent, or Firm* — Drinker Biddle & Reath L.L.P.

(57) ABSTRACT

The invention provides an isolated nucleic acid having a sequence encoding a spermidine/spermine acetyltransferase ("SSAT"), wherein translation of an mRNA comprising the encoded SSAT has increased basal translation and increased stimulated translation, compared to a wild-type mRNA encoding SSAT. Methods of use for the nucleic acid are also provided. Methods and compositions are also provided for reducing ischemia-reperfusion injury in organs or tissue for transplantation.

35 Claims, 41 Drawing Sheets

(56) References Cited

OTHER PUBLICATIONS

Parry et al., 1995, "Post-transcriptional regulation of the content of spermidine/spermine N1-acetyltransferase by N1N12-bis(ethyl)spermine", The Biochemical Journal 305 ( Pt 2):451-458.
Pegg, "Regulation of Ornithine Decarboxylase", 2006, J Biol Chem. 281(21):14529-14532.
Perez-Leal et al., "Regulation of polyamine metabolism by translational control", Amino Acids (2012) 42:611-617, (Aug. 3, 2011 Epub ahead of print).
Uimari et al, "Spermine analogue-regulated expression of spermidine/spermine N1-acetyltransferase and its effects on depletion of intracellular polyamine pools in mouse fetal fibroblasts", 2009, Biochem J. 422:101-109.
Vilela et al, "Regulation of fungal gene expression via short open reading frames in the mRNA 5'untranslated region", 2003, Molecular Microbiology 49:859-867.
Vujic et al., Effects of Conditional Overexpression of Spermidine/spermine N1-Acetyltransferase on Polyamine Pool Dynamics, Cell Growth, and Sensitivity to Polyamine Analogs 2000, J Biol Chem. 275:38319-38328.
Sun et al., "Adenovirus-mediated expression of SSAT inhibits colorectal cancer cell growth in vitro", 2008 Acta Pharmacologica Sinica 29:606-613.
Perez-Leal et al., "Polyamine-Regulated Translation of Spermidine/Spermine-N1-Acetyltransferase", Feb. 12, 2012 Mol. Cell. Biol. 32(8):1453.
Montemayor et al., "The Crystal Structure of Spermidine/Spermine N1-Acetyltransferase in Complex with Spermine Provides Insights into Substrate Binding and Catalysis", 2008 Biochemistry 47, 9145-9153.
Lee et al., "Suppression of Exogenous Gene Expression by Spermidine/Spermine N1-Acetyltransferase 1 (SSAT1) Contransfection", 2010 J. Biol. Chem. 285:15548-15556.
*Homo sapiens* spermidine/spermine N1-acetyltransferase 1 (SAT1), transcript variant 1, mRNA, NCBI Reference Sequence: NM_002970.2 (Feb. 19, 2011).
Mus musculus spermidine/spermine N1-Acetyltransferase 1(SAT1), mRNA, NCBI Reference Sequence: NM_009121.3 (Feb. 19, 2011).
McCloskey et al., "Properties and Regulation of Human Spermidine/Spermine N1-Acetyltransferase Stably Expressed in Chinese Hamster Ovary Cells", Mar. 5, 1999 The Journal of Biological Chemistry, 274:6175-6182.

\* cited by examiner

|   | SEQ ID No. |
|---|---|
| ** * * * * ***** * ** * ** * **** * * ****** * * ***** ******* | |
| MAXXXXXRXAXXXDXXDXLRLIKELAKXEXMEXQVXLTEKXLXEDGFGXHPFYHCXXAEVX 60 Consen. | 1 |
| MAKFKIRPATASDCSDILRLIKELAKYEYMEDQVMLTEKDLLEDGFGEHPFYHCLIAEVP 60 Q9JHW6 | 9 |
| MAKFKIRPATASDCSDILRLIKELAKYEYMEDQVVLTEKDLLEDGFGEHPFYHCLVAEVP 60 Q6P9U6 | 8 |
| MAKFKIRPATASDCSDILRLIKELAKYEYMEDQVILTEKDLQEDGFGEHPFYHCLVAEVP 60 P48026 | 7 |
| MAKFVIRPATAADCSDILRLIKELAKYEYMEEQVMLTEKDLLEDGFGEHPFYHCLVAEVP 60 Q3T0Q0 | 5 |
| MAKFVIRPATAADCSDILRLIKELAKYEYMEEQVMLTEKDLLEDGFGEHPFYHCLVAEVP 60 A9YUB6 | 6 |
| MAKFVIRPATAADCSDILRLIKELAKYEYMEEQVILTEKDLLEDGFGEHPFYHCLVAEVP 60 Q28999 | 4 |
| MAKFVIRPATAADCSDLLRLIKELAKYEYMEDMEDQVVLTEKELLEDGFGEHPFYHCLVAEVP 60 P21673 | 3 |
| MASFSIRAARPEDCSDLLRLIKELAKYEDMEDQVVLTEKELLEDGFGEHPFYHCLVAEVP 60 Q8AXL1 | 10 |
| MANYVIRSAVPGDCKDILRLIKELAKYEEMENQVVLTEKDLLEDGFGEHPFYHCLVAEVP 60 Q804J9 | 12 |
| MANYTIRSAVPGDCKDILRLIKELAKYEEMENQVVLTEKDLLEDGFGEHPFYHCLVAEVP 60 C1C4T9 | 13 |
| MAKFIIRSANAGDCKDILRLIKELAKYEEMENQVVLTEKDLLEDGFGEHPFYHCLVAEVP 60 Q68F31 | 11 |
| MASYILRKAEPKDVSDILRLIKELAKFEEMEDQVILTEKDLLEDGFGDHPFYHCMVAEVA 60 Q4V8U3 | 14 |

FIG. 1A

| FIG. 1 |
|---|
| FIG. 1A |
| FIG. 1B |

```
*         *******************   **        **  **     **  *  *
KXXXXXXGXXXVGFAMYYFTYDPWIGKLLYLEDFXVMXXXRGXGXGSXIXKXLXQXAXXX     120  Consen.
KEHWTPEGHSIVGFAMYYFTYDPWIGKLLYLEDFFVMSDYRGFGIGSEILKNLSQVAMKC    120  Q9JHW6
KEHWTPEGHSIVGFAMYYFTYDPWIGKLLYLEDFFVMSDYRGFGIGSEILKNLSQVAMKC    120  Q6P9U6
KEHWTPEGHSIVGFAMYYFTYDPWIGKLLYLEDFFVMSDYRGFGIGSEILKNLSQVAMKC    120  P48026
KEHLTPEGHSIVGFAMYYFTYDPWIGKLLYLEDFFVMSDYRGFGIGSEILKKLSQVAMKC    120  Q3T0Q0
KEHLTPEGHSIVGFAMYYFTYDPWIGKLLYLEDFFVMSDYRGFGIGSEILKKLSQVAMKC    120  A9YUB6
KEHLTPEGHSIVGFAMYYFTYDPWIGKLLYLEDFFVMSDYRGFGIGSEILKNLSQVAMKC    120  Q28999
KEHWTPEGHSIVGFAMYYFTYDPWIGKLLYLEDFFVMSDYRGFGIGSEILKNLSQVAMRC    120  P21673
KEQWSSEGHSIVGFAMYYFTYDPWIGKLLYLEDFYVMAEYRGLGIGSEILKNLSQVAVKC    120  Q8AXL1
KENQTIDGYTIVGFAMYYFTYDPWIGKLLYLEDFFVMNEFRGSGIGSDIFKHLSQIAVKC    120  Q804J9
KENQTIDGYTIVGFAMYYFTYDPWIGKLLYLEDFFVMNEFRGSGIGSDIFKHLSQIAVKC    120  C1C4T9
KETESVDGYTVVGFAMYYFTYDPWIGKLLYLEDFFVMDEFRGFGMGSEIFKHLGQIAMKC    120  Q68F31
KQHQSADGHVIVGFAMYYFTYDPWIGKLLYLEDFYVMKEYRGFGIGSEILKKLSQTAVRT    120  Q4V8U3

*  *******  ** * *********************** *************   *
RCSSMHFXVAEWNXXSIXFYKRRGASDLSXEEGWRLFKIDKXXLXKXXXXX     171  Consen.
RCSSMHFLVAEWNEPSINFYKRRGASDLSSEEGWRLFKIDKEYLLKMAAEE     171  Q9JHW6
RCSSMHFLVAEWNEPSINFYKRRGASDLSSEEGWRLFKIDKEYLLKMAAEE     171  Q6P9U6
RCSSMHFLVAEWNEPSINFYKRRGASDLSSEEGWRLFKIDKEYLLKMAAEE     171  P48026
RCSSMHFLVAEWNEPSINFYKRRGASDLSSEEGWRLFKIDKEYLLKMAAEE     171  Q3T0Q0
RCSSMHFLVAEWNEPSINFYKRRGASDLSSEEGWRLFKIDKEYLLKMAAD-     170  A9YUB6
RCSSMHFLVAEWNEPSINFYKRRGASDLSSEEGWRLFKIDKEYLLKMAAEE     171  Q28999
RCSSMHFLVAEWNEPSIRFYKRRGASDLSSEEGWRLFKIDKEYLLKMATEE     171  P21673
RCSSMHFLVAEWNEPSIRFYKRRGASDLSTEEGWRLFKIDKEYLLKMATEE     171  Q8AXL1
RCSSMHFLVAEWNEPSIRFYKRRGASDLSTEEGWRLFKIDKEYLCKMAAEE     171  Q804J9
RCSSMHFLVAEWNEPSIRFYKRRGASDLSTEEGWRLFKIDKEYLCKMAAEE     171  C1C4T9
RCSSMHFLVAEWNEPSIKFYKRRGASDLSTEEGWRLFKIDKEYLCKLAAEE     171  Q68F31
RCSSMHFIVAEWNTTSIEFYKRRGASDLSHEEGWRLFKIDKQSLLKMTSEE     171  Q4V8U3
```

FIG. 1B

| Residue | Residue type | Exemplary amino acids | Residue | Residue type | Exemplary amino acids |
|---|---|---|---|---|---|
| X3 | polar | K,S,N | X69 | polar | H,Y |
| X4 | aromatic | F,Y | X70 | small | S,T,V |
| X5 |  | V,K,S,I | X71 | hydrophobic, aliphatic | I,V |
| X6 | hydrophobic, aliphatic | I,L | X95 | aromatic | F,Y |
| X8 |  | P,A,S,K | X98 |  | S,A,D,N,K |
| X10 |  | T,R,N,V,E | X99 | charged | D,E |
| X11 | hydrophobic | A,P | X100 | aromatic | Y,F |
| X12 |  | A,S,E,G,K | X105 | hydrophobic | I,M |
| X14 |  | C,V | X108 | charged | E,D |
| X15 |  | S,K | X110 | hydrophobic | L,F |
| X17 | hydrophobic, aliphatic | I,L | X112 | polar | N,H,K |
| X27 | aromatic | Y,F | X114 | polar | S,G |
| X29 | polar | Y,D,E | X118 | hydrophobic | M,V |
| X32 | polar | E,D,N | X119 | charged | R,K |
| X35 | hydrophobic | I,V,M | X120 |  | C,T |
| X40 | charged | D,E | X128 | hydrophobic, aliphatic | L,I |
| X42 | hydrophobic | L,Q | X134 | polar | E,T |
| X48 | charged | E,D | X135 |  | P,T |
| X55 | hydrophobic | L,M | X138 | polar | N,R,K,E |
| X56 | hydrophobic, aliphatic | I,V | X150 | polar | S,T,H |
| X60 | hydrophobic | P,A | X162 | polar | E,Q |
| X62 | polar | E,Q | X163 | polar | Y,S |
| X63 | polar | H,Q,T,N | X165 | hydrophobic | L,C |
| X64 | big | W,L,E,Q | X167 | hydrophobic | M,L |
| X65 | polar | T,S | X168 | small | A,T |
| X66 |  | P,S,V,I,A | X169 | small | T,A,S |
| X67 | charged | E,D | X170 | charged | E,D |
|  |  |  | X171 | charged | E |

FIG. 2

| Sequence | | SEQ ID No. |
|---|---|---|
| `****  ********  *  *  ** ********  ***************  ****` | | |
| MAKFXIRPATAXDCSDILRLIKELAKYEYMEXQVXLTEKDLXEDGFGEHPFYHCLXAEVP | 60 | CONSEN 2 |
| MAKFVIRPATAADCSDILRLIKELAKYEYMEEQVILTEKDLLEDGFGEHPFYHCLVAEVP | 60 | P21673 3 |
| MAKFKIRPATASDCSDILRLIKELAKYEYMEDQVVLTEKDLLEDGFGEHPFYHCLVAEVP | 60 | Q6P9U6 8 |
| MAKFKIRPATASDCSDILRLIKELAKYEYMEDQVMLTEKDLLEDGFGEHPFYHCLIAEVP | 60 | Q9JHW6 9 |
| MAKFKIRPATASDCSDILRLIKELAKYEYMEDQVILTEKDLQEDGFGEHPFYHCLVAEVP | 60 | P48026 7 |
| MAKFVIRPATAADCSDILRLIKELAKYEYMEEQVMLTEKDLLEDGFGEHPFYHCLVAEVP | 60 | Q3T0Q0 5 |
| MAKFVIRPATAADCSDILRLIKELAKYEYMEEQVMLTEKDLLEDGFGEHPFYHCLVAEVP | 60 | A9YUB6 6 |
| MAKFVIRPATAADCSDILRLIKELAKYEYMEEQVILTEKDLLEDGFGEHPFYHCLVAEVP | 60 | Q28999 4 |

FIG. 3A

| FIG. 3 |
|---|
| FIG. 3A |
| FIG. 3B |

```
*   ********************************************************
KPHXTPEGHSIVGFAMYYFTYDPWIGKLLLYLEDFFVMSDYRGFGIGSEILKNLSQVAMXC  120  CONSEN
KEHWTPEGHSIVGFAMYYFTYDPWIGKLLLYLEDFFVMSDYRGFGIGSEILKNLSQVAMRC  120  P21673
KEHWTPEGHSIVGFAMYYFTYDPWIGKLLLYLEDFFVMSDYRGFGIGSEILKNLSQVAMKC  120  Q6P9U6
KEHWTPEGHSIVGFAMYYFTYDPWIGKLLLYLEDFFVMSDYRGFGIGSEILKNLSQVAMKC  120  Q9JHW6
KEHWTPEGHSIVGFAMYYFTYDPWIGKLLLYLEDFFVMSDYRGFGIGSEILKNLSQVAMKC  120  P48026
KEHLTPEGHSIVGFAMYYFTYDPWIGKLLLYLEDFFVMSDYRGFGIGSEILKNLSQVAMKC  120  Q3T0Q0
KEHLTPEGHSIVGFAMYYFTYDPWIGKLLLYLEDFFVMSDYRGFGIGSEILKKLSQVAMKC  120  A9YUB6
KEHLTPEGHSIVGFAMYYFTYDPWIGKLLLYLEDFFVMSDYRGFGIGSEILKNLSQVAMKC  120  Q28999

********************************************  *
RCSSMHFLVAEWNEPSINFYKRRGASDLSSEEGWRLFKIDKEYLLKMAXXX  171  CONSEN
RCSSMHFLVAEWNEPSINFYKRRGASDLSSEEGWRLFKIDKEYLLKMATEE  171  P21673
RCSSMHFLVAEWNEPSINFYKRRGASDLSSEEGWRLFKIDKEYLLKMAAEE  171  Q6P9U6
RCSSMHFLVAEWNEPSINFYKRRGASDLSSEEGWRLFKIDKEYLLKMAAEE  171  Q9JHW6
RCSSMHFLVAEWNEPSINFYKRRGASDLSSEEGWRLFKIDKEYLLKMAAEE  171  P48026
RCSSMHFLVAEWNEPSINFYKRRGASDLSSEEGWRLFKIDKEYLLKMAAEE  171  Q3T0Q0
RCSSMHFLVAEWNEPSINFYKRRGASDLSSEEGWRLFKIDKEYLLKMAAD-  170  A9YUB6
RCSSMHFLVAEWNEPSINFYKRRGASDLSSEEGWRLFKIDKEYLLKMAAEE  171  Q28999
```

| Residue | Residue type | Exemplary amino acids |
|---|---|---|
| X5 | aromatic | V,K |
| X12 | small | A,S |
| X32 | polar | E,D |
| X35 | hydrophobic | I,V,M |
| X42 | hydrophobic | L,Q |
| X56 | hydrophobic, aliphatic | I,V |
| X64 | big | W,L, |
| X119 | charged | R,K |
| X169 | small | T,A |
| X170 | charged | E,D |
| X171 | charged | E |

FIG. 5

SEQ ID No. 15

CTGGTGTTTATCCGTCACTCGCCGAGGTTCCTTGGGTCATGGTGCCAGCCTGACTG
AGAAGAGGACGCTCCCGGGAGACGAATGAGGAACCACCTCCTCCTACTGTTCAAGT
ACAGGGGCCTGGTCCGCAAAGGGAAGAAAAGCAAAGACGAAA<u>ATG</u>GCTAAATTC
GTGATCCGCCCAGCCACTGCCGCCGACTGCAGTGACATACTGCGGCTGATCAAGG
AGCTGGCTAAATATGAATACATGGAAGAACAAGTAATCTTAACTGAAAAGATCTGC
TAGAAGATGGTTTTGGAGAGCACCCCTTTTACCACTGCCTGGTTGCAGAAGTGCCG
AAAGAGCACTGGACTCCGGAAGGACACAGCATTGTTGGTTTTGCCATGTACTATTTT
ACCTATGACCCGTGGATTGGCAAGTTATTGTATCTTGAGGACTTCTTCGTGATGAGT
GATTATAGAGGCTTTGGCATAGGATCAGAAATTCTGAAGAATCTAAGCCAGGTTGCA
ATGAGGTGTCGCTGCAGCAGCATGCACTTCTTGGTAGCAGAATGGAATGAACCATC
CATCAACTTCTATAAA<u>AGA</u>AGAGGTGCTTCTGATCTGTCCAGTGAAGAGGGTTGGA
GACTGTTCAAGATCGACAAGGAGTACTTGCTAAAAATGGCAACAGAGGAG<u>T</u>GAGGA
GTGCTGCTGTAGATGACAACCTCCATTCTATTTTAGAATAAATTCCCAACTTCTCTTG
CTTTCTATGCTGTTTGTAGTGAAATAATAGAATGAGCACCCATTCCAAAGCTTTATTA
CCAGTGGCGTTGTTGCATGTTTGAAATGAGGTCTGTTTAAAGTGGCAATCTCAGATG
CAGTTTGGAGAGTCAGATCTTTCTCCTTGAATATCTTTCGATAAACAACAAGGTGGT
GTGATCTTAATATATTTGAAAAAACTTCATTCTCGTGAGTCATTTAAATGTGTACAAT
GTACACACTGGTACTTAGAGTTTCTGTTTGATTCTTTTTTAATAAACTACTCTTTGATT
TAAAAAAAAAAAAAAAAA

SEQ ID Nos. 16 (DNA) and 17 (protein)

```
atg gct aaa ttc gtg atc cgc cca gcc act gcc gcc gac tgc agt gac     48
Met Ala Lys Phe Val Ile Arg Pro Ala Thr Ala Ala Asp Cys Ser Asp
 1               5                  10                  15 ata ctg cgg ctg atc aag gag ctg gct aaa tat gaa tac atg gaa gaa     96
Ile Leu Arg Leu Ile Lys Glu Leu Ala Lys Tyr Glu Tyr Met Glu Glu
             20                  25                  30 caa gta atc tta act gaa aaa gat ctg cta gaa gat ggt ttt gga gag    144
Gln Val Ile Leu Thr Glu Lys Asp Leu Leu Glu Asp Gly Phe Gly Glu
         35                  40                  45 cac ccc ttt tac cac tgc ctg gtt gca gaa gtg ccg aaa gag cac tgg    192
His Pro Phe Tyr His Cys Leu Val Ala Glu Val Pro Lys Glu His Trp
     50                  55                  60
```

FIG. 6A

| FIG. 6 |
|---|
| FIG. 6A |
| FIG. 6B |

FIG. 6B

```
act ccg gaa gga cac agc att gtt ggt ttt gcc atg tac tat ttt acc    240
Thr Pro Glu Gly His Ser Ile Val Gly Phe Ala Met Tyr Tyr Phe Thr
 65              70              75              80 tat gac ccg tgg att ggc aag tta ttg tat ctt gag gac ttc gtg        288
Tyr Asp Pro Trp Ile Gly Lys Leu Leu Tyr Leu Glu Asp Phe Val
             85              90              95 atg agt gat tat aga ggc ttt ggc ata ggc atc att ctg aag aat        336
Met Ser Asp Tyr Arg Gly Phe Gly Ile Gly Ile Ile Leu Lys Asn
        100             105             110 cta agc cag gtt gca atg agg tgt cgc tgc agc atg cac ttc ttg        384
Leu Ser Gln Val Ala Met Arg Cys Arg Cys Ser Met His Phe Leu
    115             120             125 gta gca gaa tgg aat gaa cca tcc atc aac ttc tat aaa aga aga ggt    432
Val Ala Glu Trp Asn Glu Pro Ser Ile Asn Phe Tyr Lys Arg Arg Gly
            130             135             140 gct tct gat ctg tcc agt gaa gag ggt ggg gtg aga ctg ttc aag atc gac 480
Ala Ser Asp Leu Ser Ser Glu Glu Gly Gly Val Arg Leu Phe Lys Ile Asp
145             150             155             160 aag gag tac ttg cta aaa atg gca aca gag gag tga                    516
Lys Glu Tyr Leu Leu Lys Met Ala Thr Glu Glu *
            165             170
```

FIG. 7

SEQ ID No. 18

```
      -150            -140            -130            -120
CTGGT GTTTATCCGT CACTCGCCGA GGTTCCTTGG GTCATGGTGC

-110            -100            -90             -80
CAGCCTGACT GAGAAGAGGA CGCTCCCGGG AGACGAATGA

-70             -60             -50             -40
GGAACCACCT CCTCCTACTG TTCAAGTACA GGGGCCTGGT

-30             -20             -10             -1 +1
CCGCAAAGGG AAGAAAAGCA AAAGACGAAA ATG
```

SEQ ID No. 19

ATGGCTAAATTCGTGATCCGCCCAGCCACTGCCGCCGACTGCAGTGACATACTGCGGCTGATCAAGGA
GCTGGCTAAATATGAATACATGGAAGAACAAGTAATCTTAACTGAAAAAGATCTGCTAGAAGATGGTT
TTGGAGAGCACCCCTTTTACCACTGCCTGGTTGCCAAGAGTGCCGAAAGACACTGGACTCCGAAGGA
CACAGCATTGTTGGTTTTGCCATGAGTGATTATAGAGGCTTTGGCATAGGATCAGAAATTCTGAAGAATCTAA
TGAGGACTTCTTCGTGATGAGGTGTCGCTGCAGCAGCATGCACTTCTTGGTAGCAGAGAATGAACCATCC
GCCAGGTTGCAATGAGGTGTCGCTGCAGCAGGTGCTTCTGATCTGTCCAGTGAAGAGGGTTGGAGACTGTTCAAGAT
ATCAACTTCTATAAACGCAGAGGTACTTGCTAAAAATGGCTAAAAATGGCAACAGAGGAG

FIG. 8A

SEQ ID No. 20

CCACCCTCCTCCTACTGTTCAAGTACACAGGGGCCCTGGTCCCGACTGCAGCCACTGCCGCCCAAAGGGAAGAAAAGCAAAAGACGAAAAT
GGCTAAATTCGTGATCAATATGAATACATCCGCCCAGCCACTGCCGCCGACTAATCTTAACTGAAAAAGATCTGCGGCTGATCAAGGAGC
TGGCTAAATATGAATACATGGAAGAACAAGTAATCTTAACTGAAAAAGATCTGCTAGAAGATGGTTTT
GGAGAGCACCCCTTTTACCACTGCCTGGTTGCCAAGAGTGCCGAAAGAGCACTGGACTCCGAAGACA
CAGCATTGTTGGTTTTGCCATGAGTGATTATAGAGGCTTTGGCATAGGATCAGAAATTCTGAAGAATCTAATG
AGGACTTCTTCGTGATGAGGTGTCGCTGCAGCAGCATGCACTTCTTGGTAGCAGAGAGGGTTGGAGACTGTTCAAGC
CAGGTTGCAATGAGGTGTCGCTGCAGCAGGTGCTTCTGATCTGTCCAGTGAAGAGGGTTGGAGACTGTTCAAGATCG
CAACTTCTATAAACGCAGAGGTACTTGCTAAAAATGGCAACAGAGGAG

FIG. 8B

SEQ ID No. 21

CTGGTGTTTATCCGTCACTCGCCGAGGTTCCTTGGGTCATAGTGCCAGCCTGACTGAGAAGAGGACGC
TCCCGGGACGAATAAGGAACCACCTCCTCCTACTGTTCAAGTACAGGGGCCTGGTTCCGCAAAGGAA
GAAAAGCAAAAGACGAAAATGGCTAAATTCGTGATCCGCCACTGCCGCCGACTGCAGTGACAT
ACTGCGCTGATCAAGGAGCTGGCTAAATATGAATACATGGAAGAACAAGTAATCTTAACTGAAAAAG
ATCTGCTAGAAGATGGTTTTGGAGAGCACAGCATTGTTGGTTTTGCCAGAAGTGCCGAAAGAG
CACTGGACTCCCGGAAGGACACAGCATTGTTGAGGACTTCTTCGTGATGAGTGATTATAGAGCCCGTGGAT
TGGCAAGTTATTGTATCTTGAGGACTTCTTCGTGATGAGTGATTATAGAGGCTTTGGCATAGGATCAG
AAATTCTGAAGAATGAACCATCAACTTCTATAAACGCAGAGGTGCTTCTGATCTGTCCAGTGAAGAGCA
GAATGGAATGAACCATCAACTTCTATAAACGCAGAGGTGCTTCTGATCTGTCCAGTGAAGAGGG
TTGGAGACTGTTCAAGATCGACAAGGAGTACTTGCTAAAAATGGCAACAGAGGAG

FIG. 8C

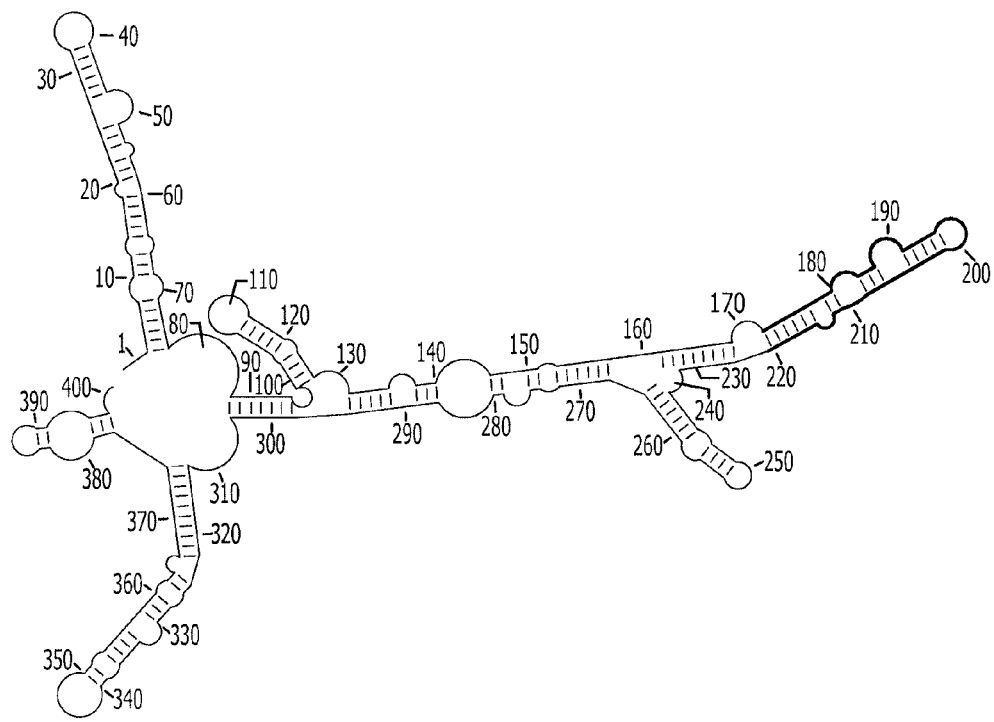
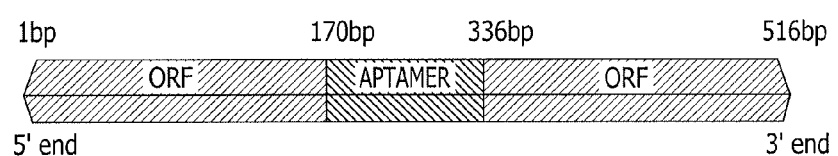
FIG. 9A

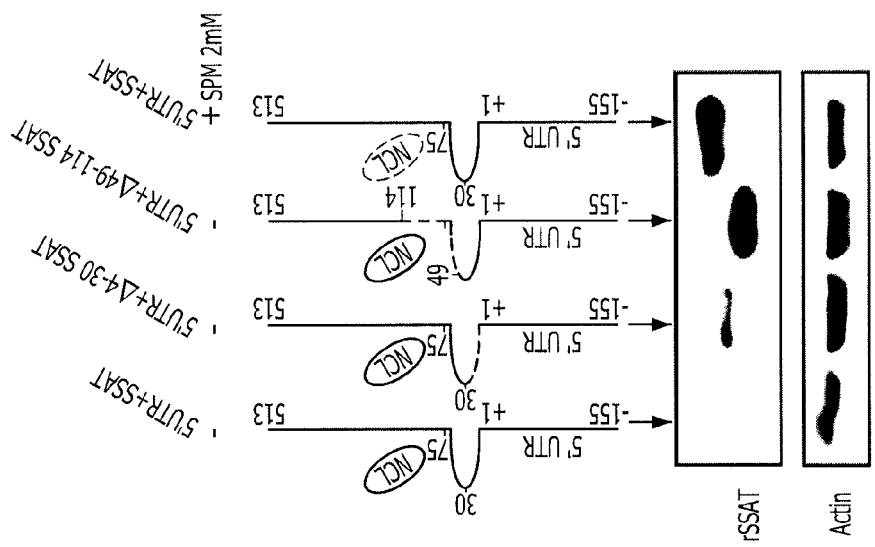
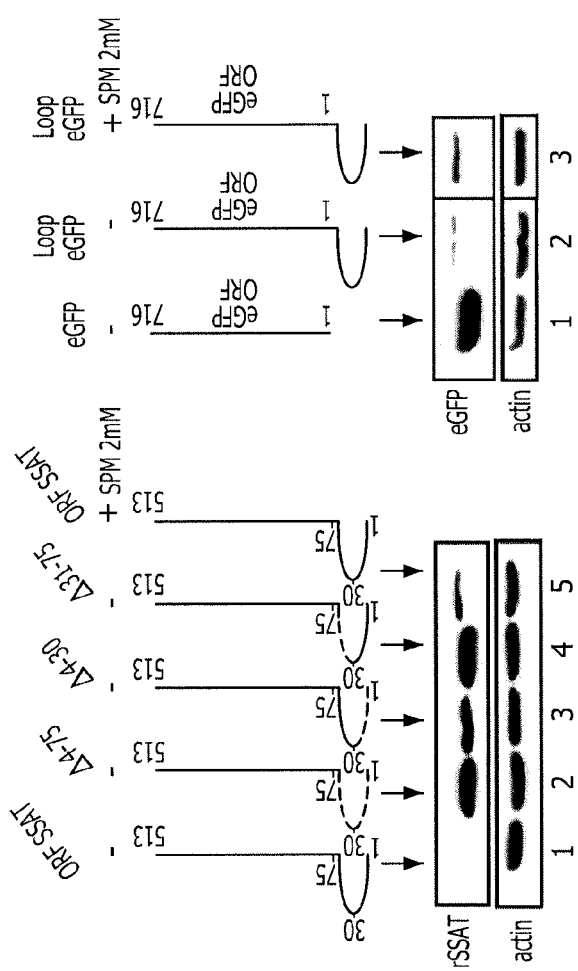
FIG. 13D
FIG. 13C
FIG. 13B

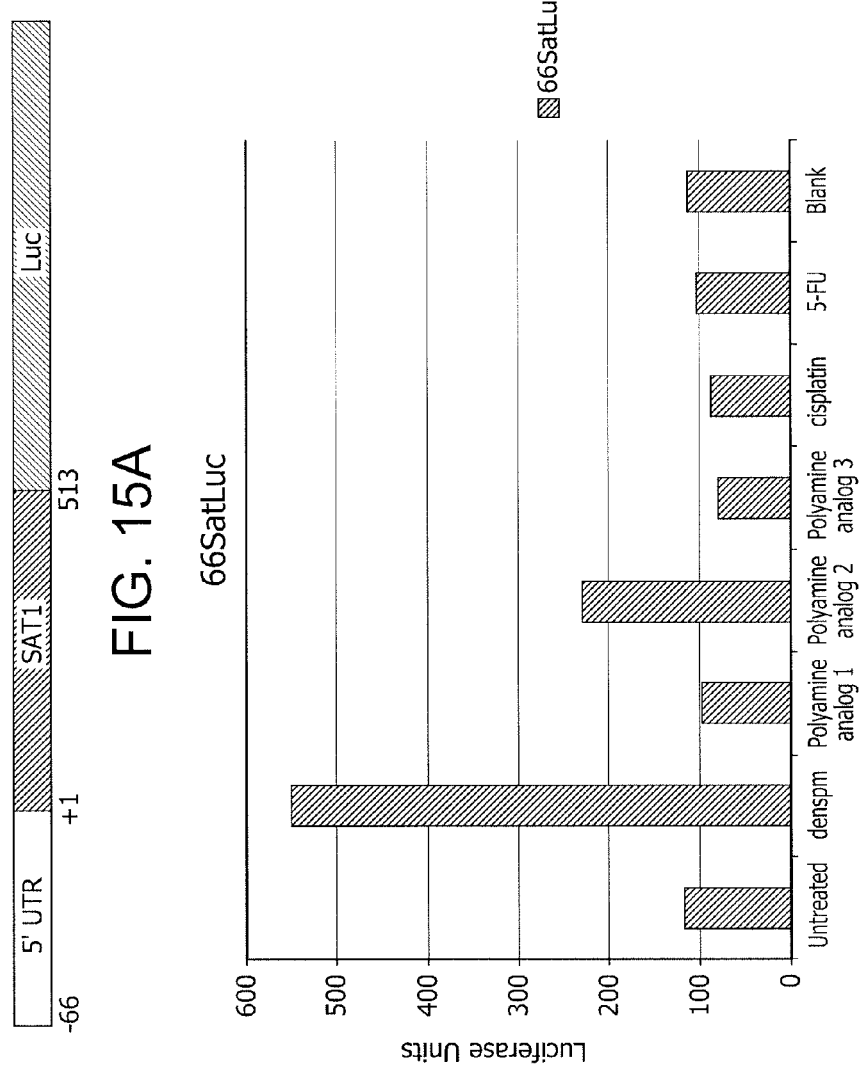

Nucleotides 400-453 of SSAT ORF aa143

A427C
A429G

SEQUENCE LISTING

```
<160> NUMBER OF SEQ ID NOS: 84

<210> SEQ ID NO 1
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(6)
<223> OTHER INFORMATION: Any amino acid
<220> FEATURE:
<221> NAME/KEY: MISC_FEATURE
<222> LOCATION: (3)..(171)
<223> OTHER INFORMATION: For MOD-RES, see specification and Figure 2 as
      filed for detailed description of substitutions and preferred
      embodiments
```

```
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(12)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (48)..(48)
<223> OTHER INFORMATION: Any amino acid
<220> FEATURE:
<221> NAME/KEY: MOD_RES
<222> LOCATION: (55)..(56)
<223> OTHER INFORMATION: Any amino acid
<220> FEATURE:
<221> NAME/KEY: MOD_RES
<222> LOCATION: (60)..(60)
<223> OTHER INFORMATION: Any amino acid
<220> FEATURE:
<221> NAME/KEY: MOD_RES
<222> LOCATION: (62)..(67)
<223> OTHER INFORMATION: Any amino acid
<220> FEATURE:
<221> NAME/KEY: MOD_RES
<222> LOCATION: (69)..(71)
<223> OTHER INFORMATION: Any amino acid
<220> FEATURE:
<221> NAME/KEY: MOD_RES
<222> LOCATION: (95)..(95)
<223> OTHER INFORMATION: Any amino acid
<220> FEATURE:
<221> NAME/KEY: MOD_RES
<222> LOCATION: (98)..(100)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (105)..(105)
<223> OTHER INFORMATION: Any amino acid
<220> FEATURE:
<221> NAME/KEY: MOD_RES
<222> LOCATION: (108)..(108)
```

```
<223> OTHER INFORMATION: Any amino acid
<220> FEATURE:
<221> NAME/KEY: MOD_RES
<222> LOCATION: (110)..(110)
<223> OTHER INFORMATION: Any amino acid
<220> FEATURE:
<221> NAME/KEY: MOD_RES
<222> LOCATION: (112)..(112)
<223> OTHER INFORMATION: Any amino acid
<220> FEATURE:
<221> NAME/KEY: MOD_RES
<222> LOCATION: (114)..(114)
<223> OTHER INFORMATION: Any amino acid
<220> FEATURE:
<221> NAME/KEY: MOD_RES
<222> LOCATION: (116)..(116)
<223> OTHER INFORMATION: Any amino acid
<220> FEATURE:
<221> NAME/KEY: MOD_RES
<222> LOCATION: (118)..(120)
<223> OTHER INFORMATION: Any amino acid
<220> FEATURE:
<221> NAME/KEY: MOD_RES
<222> LOCATION: (128)..(128)
<223> OTHER INFORMATION: Any amino acid
<220> FEATURE:
<221> NAME/KEY: MOD_RES
<222> LOCATION: (134)..(135)
<223> OTHER INFORMATION: Any amino acid
<220> FEATURE:
<221> NAME/KEY: MOD_RES
<222> LOCATION: (138)..(138)
<223> OTHER INFORMATION: Any amino acid
<220> FEATURE:
<221> NAME/KEY: MOD_RES
<222> LOCATION: (150)..(150)
<223> OTHER INFORMATION: Any amino acid
<220> FEATURE:
<221> NAME/KEY: MOD_RES
<222> LOCATION: (162)..(163)
<223> OTHER INFORMATION: Any amino acid
<220> FEATURE:
<221> NAME/KEY: MOD_RES
<222> LOCATION: (165)..(165)
<223> OTHER INFORMATION: Any amino acid
<220> FEATURE:
<221> NAME/KEY: MOD_RES
<222> LOCATION: (167)..(171)
<223> OTHER INFORMATION: Any amino acid

<400> SEQUENCE: 1

Met Ala Xaa Xaa Xaa Xaa Arg Xaa Ala Xaa Xaa Asp Xaa Xaa Asp
1               5                   10                  15

Xaa Leu Arg Leu Ile Lys Glu Leu Ala Lys Xaa Glu Xaa Met Glu Xaa
            20                  25                  30

Gln Val Xaa Leu Thr Glu Lys Xaa Leu Xaa Glu Asp Gly Phe Gly Xaa
        35                  40                  45

His Pro Phe Tyr His Cys Xaa Xaa Ala Glu Val Xaa Lys Xaa Xaa Xaa
    50                  55                  60

Xaa Xaa Xaa Gly Xaa Xaa Xaa Val Gly Phe Ala Met Tyr Tyr Phe Thr
65                  70                  75                  80

Tyr Asp Pro Trp Ile Gly Lys Leu Leu Tyr Leu Glu Asp Phe Xaa Val
                85                  90                  95

Met Xaa Xaa Xaa Arg Gly Xaa Gly Xaa Gly Ser Xaa Ile Xaa Lys Xaa
            100                 105                 110

Leu Xaa Gln Xaa Ala Xaa Xaa Xaa Arg Cys Ser Ser Met His Phe Xaa
        115                 120                 125

Val Ala Glu Trp Asn Xaa Xaa Ser Ile Xaa Phe Tyr Lys Arg Arg Gly
    130                 135                 140
```

```
Ala Ser Asp Leu Ser Xaa Glu Glu Gly Trp Arg Leu Phe Lys Ile Asp
145                 150                 155                 160

Lys Xaa Xaa Leu Xaa Lys Xaa Xaa Xaa Xaa
            165                 170

<210> SEQ ID NO 2
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MISC_FEATURE
<222> LOCATION: (5)..(171)
<223> OTHER INFORMATION: For MOD_RES, see specification and Figure 4 as
      filed for detailed description of substitutions and preferred
      embodiments
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (35)..(35)
<223> OTHER INFORMATION: Any amino acid
<220> FEATURE:
<221> NAME/KEY: MOD_RES
<222> LOCATION: (42)..(42)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (119)..(119)
<223> OTHER INFORMATION: Any amino acid
<220> FEATURE:
<221> NAME/KEY: MOD_RES
<222> LOCATION: (169)..(171)
<223> OTHER INFORMATION: Any amino acid

<400> SEQUENCE: 2

Met Ala Lys Phe Xaa Ile Arg Pro Ala Thr Ala Xaa Asp Cys Ser Asp
1               5                   10                  15

Ile Leu Arg Leu Ile Lys Glu Leu Ala Lys Tyr Glu Tyr Met Glu Xaa
            20                  25                  30

Gln Val Xaa Leu Thr Glu Lys Asp Leu Xaa Glu Asp Gly Phe Gly Glu
        35                  40                  45

His Pro Phe Tyr His Cys Leu Xaa Ala Glu Val Pro Lys Pro His Xaa
50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110
```

Leu Ser Gln Val Ala Met Xaa Cys Arg Cys Ser Ser Met His Phe Leu
            115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Xaa Xaa Xaa
                165                 170

<210> SEQ ID NO 3
<211> LENGTH: 171
<212> TYPE: PRT
<213> ORGANISM: Homo sapiens

<400> SEQUENCE: 3

Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Ile Leu Thr Glu Lys Asp Leu Leu Glu Asp Gly Phe Gly Glu
        35                  40                  45

His Pro Phe Tyr His Cys Leu Val Ala Glu Val Pro Lys Glu His Trp
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110

Leu Ser Gln Val Ala Met Arg Cys Arg Cys Ser Ser Met His Phe Leu
            115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Thr Glu Glu
                165                 170

<210> SEQ ID NO 4
<211> LENGTH: 171
<212> TYPE: PRT
<213> ORGANISM: Sus scrofa

<400> SEQUENCE: 4

Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Ile Leu Thr Glu Lys Asp Leu Leu Glu Asp Gly Phe Gly Glu
        35                  40                  45

His Pro Phe Tyr His Cys Leu Val Ala Glu Val Pro Lys Glu His Leu
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

```
Met Ser Asp Tyr Arg Gly Phe Gly Ile Gly Ser Glu Ile Leu Lys Asn
            100                 105                 110

Leu Ser Gln Val Ala Met Lys Cys Arg Cys Ser Ser Met His Phe Leu
        115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
                165                 170
```

<210> SEQ ID NO 5
<211> LENGTH: 171
<212> TYPE: PRT
<213> ORGANISM: Bos taurus

<400> SEQUENCE: 5

```
Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Met Leu Thr Glu Lys Asp Leu Leu Glu Asp Gly Phe Gly Glu
        35                  40                  45

His Pro Phe Tyr His Cys Leu Val Ala Glu Val Pro Lys Glu His Leu
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Val
            85                  90                  95

Met Ser Asp Tyr Arg Gly Phe Gly Ile Gly Ser Glu Ile Leu Lys Lys
            100                 105                 110

Leu Ser Gln Val Ala Met Lys Cys Arg Cys Ser Ser Met His Phe Leu
        115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
                165                 170
```

<210> SEQ ID NO 6
<211> LENGTH: 170
<212> TYPE: PRT
<213> ORGANISM: Capra hircus

<400> SEQUENCE: 6

```
Met Ala Lys Phe Val Ile Arg Pro Ala Thr Ala Ala Asp Cys Ser Asp
1               5                   10                  15

Ile Leu Arg Leu Ile Lys Glu Leu Ala Lys Tyr Glu Tyr Met Glu Glu
            20                  25                  30

Gln Val Met Leu Thr Glu Lys Asp Leu Leu Glu Asp Gly Phe Gly Glu
        35                  40                  45

His Pro Phe Tyr His Cys Leu Val Ala Glu Val Pro Lys Glu His Leu
    50                  55                  60

Thr Pro Glu Gly His Ser Ile Val Gly Phe Ala Met Tyr Tyr Phe Thr
65                  70                  75                  80
```

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Lys
              100                 105                 110

Leu Ser Gln Val Ala Met Lys Cys Arg Cys Ser Ser Met His Phe Leu
          115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Asp
              165                 170

<210> SEQ ID NO 7
<211> LENGTH: 171
<212> TYPE: PRT
<213> ORGANISM: Mus musculus

<400> SEQUENCE: 7

Met Ala Lys Phe Lys Ile Arg Pro Ala Thr Ala Ser Asp Cys Ser Asp
1               5                   10                  15

Ile Leu Arg Leu Ile Lys Glu Leu Ala Lys Tyr Glu Tyr Met Glu Asp
              20                  25                  30

Gln Val Ile Leu Thr Glu Lys Asp Leu Gln Glu Asp Gly Phe Gly Glu
          35                  40                  45

His Pro Phe Tyr His Cys Leu Val Ala Glu Val Pro Lys Glu His Trp
50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
              100                 105                 110

Leu Ser Gln Val Ala Met Lys Cys Arg Cys Ser Ser Met His Phe Leu
          115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
              165                 170

<210> SEQ ID NO 8
<211> LENGTH: 171
<212> TYPE: PRT
<213> ORGANISM: Rattus norvegicus

<400> SEQUENCE: 8

Met Ala Lys Phe Lys Ile Arg Pro Ala Thr Ala Ser Asp Cys Ser Asp
1               5                   10                  15

Ile Leu Arg Leu Ile Lys Glu Leu Ala Lys Tyr Glu Tyr Met Glu Asp
              20                  25                  30

Gln Val Val Leu Thr Glu Lys Asp Leu Leu Glu Asp Gly Phe Gly Glu
          35                  40                  45

His Pro Phe Tyr His Cys Leu Val Ala Glu Val Pro Lys Glu His Trp
50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110

Leu Ser Gln Val Ala Met Lys Cys Arg Cys Ser Ser Met His Phe Leu
        115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
                165                 170

<210> SEQ ID NO 9
<211> LENGTH: 171
<212> TYPE: PRT
<213> ORGANISM: Cricetulus griseus

<400> SEQUENCE: 9

Met Ala Lys Phe Lys Ile Arg Pro Ala Thr Ala Ser Asp Cys Ser Asp
1               5                   10                  15

Ile Leu Arg Leu Ile Lys Glu Leu Ala Lys Tyr Glu Tyr Met Glu Asp
                20                  25                  30

Gln Val Met Leu Thr Glu Lys Asp Leu Leu Glu Asp Gly Phe Gly Glu
            35                  40                  45

His Pro Phe Tyr His Cys Leu Ile Ala Glu Val Pro Lys Glu His Trp
        50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110

Leu Ser Gln Val Ala Met Lys Cys Arg Cys Ser Ser Met His Phe Leu
        115                 120                 125

Val Ala Glu Trp Asn Glu Pro Ser Ile Asn Phe Tyr Lys Arg Arg Gly
130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
                165                 170

<210> SEQ ID NO 10
<211> LENGTH: 171
<212> TYPE: PRT
<213> ORGANISM: Gallus gallus

<400> SEQUENCE: 10

Met Ala Ser Phe Ser Ile Arg Ala Ala Arg Pro Glu Asp Cys Ser Asp
1               5                   10                  15

Leu Leu Arg Leu Ile Lys Glu Leu Ala Lys Tyr Glu Asp Met Glu Asp
                20                  25                  30

Gln Val Val Leu Thr Glu Lys Glu Leu Leu Glu Asp Gly Phe Gly Glu
            35                  40                  45

His Pro Phe Tyr His Cys Leu Val Ala Glu Val Pro Lys Glu Gln Trp
    50                  55                  60

Ser Ser Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Tyr Val
                85                  90                  95

Met Ala Glu Tyr Arg Gly Leu Gly Ile Gly Ser Glu Ile Leu Lys Asn
            100                 105                 110

Leu Ser Gln Val Ala Val Lys Cys Arg Cys Ser Ser Met His Phe Leu
        115                 120                 125

Val Ala Glu Trp Asn Glu Pro Ser Ile Arg Phe Tyr Lys Arg Arg Gly
    130                 135                 140

Ala Ser Asp Leu Ser Thr Glu Glu Gly Trp Arg Leu Phe Lys Ile Asp
145                 150                 155                 160

Lys Glu Tyr Leu Leu Lys Met Ala Thr Glu Glu
                165                 170

<210> SEQ ID NO 11
<211> LENGTH: 171
<212> TYPE: PRT
<213> ORGANISM: Xenopus laevis

<400> SEQUENCE: 11

Met Ala Lys Phe Ile Ile Arg Ser Ala Asn Ala Gly Asp Cys Lys Asp
1               5                   10                  15

Ile Leu Arg Leu Ile Lys Glu Leu Ala Lys Tyr Glu Glu Met Glu Asn
            20                  25                  30

Gln Val Val Leu Thr Glu Lys Asp Leu Leu Glu Asp Gly Phe Gly Glu
        35                  40                  45

His Pro Phe Tyr His Cys Leu Val Ala Glu Val Pro Lys Glu Thr Glu
    50                  55                  60

Ser Val Asp Gly Tyr Thr Val Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Asp Glu Phe Arg Gly Phe Gly Met Gly Ser Glu Ile Phe Lys His
            100                 105                 110

Leu Gly Gln Ile Ala Met Lys Cys Arg Cys Ser Ser Met His Phe Leu
        115                 120                 125

Val Ala Glu Trp Asn Glu Pro Ser Ile Lys Phe Tyr Lys Arg Arg Gly
    130                 135                 140

Ala Ser Asp Leu Ser Thr Glu Glu Gly Trp Arg Leu Phe Lys Ile Asp
145                 150                 155                 160

Lys Glu Tyr Leu Cys Lys Leu Ala Ala Glu Glu
                165                 170

<210> SEQ ID NO 12
<211> LENGTH: 171
<212> TYPE: PRT
<213> ORGANISM: Pelophylax ridibundus

<400> SEQUENCE: 12

Met Ala Asn Tyr Val Ile Arg Ser Ala Val Pro Gly Asp Cys Lys Asp
1               5                   10                  15

Ile Leu Arg Leu Ile Lys Glu Leu Ala Lys Tyr Glu Glu Met Glu Asn
            20                  25                  30

```
Gln Val Val Leu Thr Glu Lys Asp Leu Leu Glu Asp Gly Phe Gly Glu
            35                  40                  45

His Pro Phe Tyr His Cys Leu Val Ala Glu Val Pro Lys Glu Asn Gln
     50                  55                  60

Thr Ile Asp Gly Tyr Thr Ile Val Gly Phe Ala Met Tyr Tyr Phe Thr
 65                  70                  75                  80

Tyr Asp Pro Trp Ile Gly Lys Leu Leu Tyr Leu Glu Asp Phe Phe Val
                 85                  90                  95

Met Asn Glu Phe Arg Gly Ser Gly Ile Gly Ser Asp Ile Phe Lys His
            100                 105                 110

Leu Ser Gln Ile Ala Val Lys Cys Arg Cys Ser Ser Met His Phe Leu
        115                 120                 125

Val Ala Glu Trp Asn Glu Pro Ser Ile Arg Phe Tyr Lys Arg Arg Gly
    130                 135                 140

Ala Ser Asp Leu Ser Thr Glu Glu Gly Trp Arg Leu Phe Lys Ile Asp
145                 150                 155                 160

Lys Glu Tyr Leu Cys Lys Met Ala Ala Glu Glu
                165                 170

<210> SEQ ID NO 13
<211> LENGTH: 171
<212> TYPE: PRT
<213> ORGANISM: Rana catesbeiana

<400> SEQUENCE: 13

Met Ala Asn Tyr Thr Ile Arg Ser Ala Val Pro Gly Asp Cys Lys Asp
1               5                   10                  15

Ile Leu Arg Leu Ile Lys Glu Leu Ala Lys Tyr Glu Glu Met Glu Asn
            20                  25                  30

Gln Val Val Leu Thr Glu Lys Asp Leu Leu Glu Asp Gly Phe Gly Glu
            35                  40                  45

His Pro Phe Tyr His Cys Leu Val Ala Glu Val Pro Lys Glu Asn Gln
     50                  55                  60

Thr Ile Asp Gly Tyr Thr Ile Val Gly Phe Ala Met Tyr Tyr Phe Thr
 65                  70                  75                  80

Tyr Asp Pro Trp Ile Gly Lys Leu Leu Tyr Leu Glu Asp Phe Phe Val
                 85                  90                  95

Met Asn Glu Phe Arg Gly Ser Gly Ile Gly Ser Asp Ile Phe Lys His
            100                 105                 110

Leu Ser Gln Ile Ala Val Lys Cys Arg Cys Ser Ser Met His Phe Leu
        115                 120                 125

Val Ala Glu Trp Asn Glu Pro Ser Ile Arg Phe Tyr Lys Arg Arg Gly
    130                 135                 140

Ala Ser Asp Leu Ser Thr Glu Glu Gly Trp Arg Leu Phe Lys Ile Asp
145                 150                 155                 160

Lys Glu Tyr Leu Cys Lys Met Ala Ala Glu Glu
                165                 170

<210> SEQ ID NO 14
<211> LENGTH: 171
<212> TYPE: PRT
<213> ORGANISM: Danio rerio

<400> SEQUENCE: 14

Met Ala Ser Tyr Ile Leu Arg Lys Ala Glu Pro Lys Asp Val Ser Asp
1               5                   10                  15
```

Ile Leu Arg Leu Ile Lys Glu Leu Ala Lys Phe Glu Glu Met Glu Asp
             20                  25                  30

Gln Val Ile Leu Thr Glu Lys Asp Leu Leu Glu Asp Gly Phe Gly Asp
         35                  40                  45

His Pro Phe Tyr His Cys Met Val Ala Glu Val Ala Lys Gln His Gln
 50                  55                  60

Ser Ala Asp Gly His Val Ile Val Gly Phe Ala Met Tyr Tyr Phe Thr
 65                  70                  75                  80

Tyr Asp Pro Trp Ile Gly Lys Leu Leu Tyr Leu Glu Asp Phe Tyr Val
                 85                  90                  95

Met Lys Glu Tyr Arg Gly Phe Gly Ile Gly Ser Glu Ile Leu Lys Lys
            100                 105                 110

Leu Ser Gln Thr Ala Val Arg Thr Arg Cys Ser Ser Met His Phe Ile
        115                 120                 125

Val Ala Glu Trp Asn Thr Thr Ser Ile Glu Phe Tyr Lys Arg Arg Gly
130                 135                 140

Ala Ser Asp Leu Ser His Glu Glu Gly Trp Arg Leu Phe Lys Ile Asp
145                 150                 155                 160

Lys Gln Ser Leu Leu Lys Met Thr Ser Glu Glu
                165                 170

<210> SEQ ID NO 15
<211> LENGTH: 1041
<212> TYPE: DNA
<213> ORGANISM: Homo sapiens

<400> SEQUENCE: 15
ctggtgttta tccgtcactc gccgaggttc cttgggtcat ggtgccagcc tgactgagaa      60
gaggacgctc ccgggagacg aatgaggaac cacctcctcc tactgttcaa gtacaggggc     120
ctggtccgca agggaagaa aagcaaaaga cgaaaatggc taaattcgtg atccgcccag      180
ccactgccgc cgactgcagt gacatactgc ggctgatcaa ggagctggct aaatatgaat     240
acatggaaga acaagtaatc ttaactgaaa aagatctgct agaagatggt tttggagagc     300 accccttta ccactgcctg gttgcagaag tgccgaaaga gcactggact ccggaaggac      360
acagcattgt tggttttgcc atgtactatt ttacctatga cccgtggatt ggcaagttat     420
tgtatcttga ggacttcttc gtgatgagtg attatagagg ctttggcata ggatcagaaa     480
ttctgaagaa tctaagccag gttgcaatga ggtgtcgctg cagcagcatg cacttcttgg     540
tagcagaatg gaatgaacca tccatcaact tctataaaag aagaggtgct tctgatctgt     600
ccagtgaaga gggttggaga ctgttcaaga tcgacaagga gtacttgcta aaaatggcaa     660
cagaggagtg aggagtgctg ctgtagatga caacctccat tctattttag aataaattcc     720
caacttctct tgctttctat gctgtttgta gtgaaataat agaatgagca cccattccaa     780
agctttatta ccagtggcgt tgttgcatgt ttgaaatgag gtctgtttaa gtggcaatc     840 tcagatgcag tttggagagt cagatctttc tccttgaata tctttcgata acaacaagg      900 tggtgtgatc ttaatatatt tgaaaaaaac ttcattctcg tgagtcattt aaatgtgtac     960
aatgtacaca ctggtactta gagtttctgt tgattctttt ttaataaaac tactctttga    1020
tttaaaaaaa aaaaaaaaa a                                                1041

<210> SEQ ID NO 16
<211> LENGTH: 516
<212> TYPE: DNA

<213> ORGANISM: Homo sapiens
<220> FEATURE:
<221> NAME/KEY: CDS
<222> LOCATION: (1)..(513)

<400> SEQUENCE: 16

```
atg gct aaa ttc gtg atc cgc cca gcc act gcc gcc gac tgc agt gac      48
Met Ala Lys Phe Val Ile Arg Pro Ala Thr Ala Ala Asp Cys Ser Asp
1               5                  10                  15 ata ctg cgg ctg atc aag gag ctg gct aaa tat gaa tac atg gaa gaa      96
Ile Leu Arg Leu Ile Lys Glu Leu Ala Lys Tyr Glu Tyr Met Glu Glu
            20                  25                  30 caa gta atc tta act gaa aaa gat ctg cta gaa gat ggt ttt gga gag     144
Gln Val Ile Leu Thr Glu Lys Asp Leu Leu Glu Asp Gly Phe Gly Glu
        35                  40                  45 cac ccc ttt tac cac tgc ctg gtt gca gaa gtg ccg aaa gag cac tgg     192
His Pro Phe Tyr His Cys Leu Val Ala Glu Val Pro Lys Glu His Trp
    50                  55                  60 act ccg gaa gga cac agc att gtt ggt ttt gcc atg tac tat ttt acc     240
Thr Pro Glu Gly His Ser Ile Val Gly Phe Ala Met Tyr Tyr Phe Thr
65                  70                  75                  80 tat gac ccg tgg att ggc aag tta ttg tat ctt gag gac ttc ttc gtg     288
Tyr Asp Pro Trp Ile Gly Lys Leu Leu Tyr Leu Glu Asp Phe Phe Val
                85                  90                  95 atg agt gat tat aga ggc ttt ggc ata gga tca gaa att ctg aag aat     336
Met Ser Asp Tyr Arg Gly Phe Gly Ile Gly Ser Glu Ile Leu Lys Asn
            100                 105                 110 cta agc cag gtt gca atg agg tgt cgc tgc agc agc atg cac ttc ttg     384
Leu Ser Gln Val Ala Met Arg Cys Arg Cys Ser Ser Met His Phe Leu
        115                 120                 125 gta gca gaa tgg aat gaa cca tcc atc aac ttc tat aaa aga aga ggt     432
Val Ala Glu Trp Asn Glu Pro Ser Ile Asn Phe Tyr Lys Arg Arg Gly
    130                 135                 140 gct tct gat ctg tcc agt gaa gag ggt tgg aga ctg ttc aag atc gac     480
Ala Ser Asp Leu Ser Ser Glu Glu Gly Trp Arg Leu Phe Lys Ile Asp
145                 150                 155                 160 aag gag tac ttg cta aaa atg gca aca gag gag tga                     516
Lys Glu Tyr Leu Leu Lys Met Ala Thr Glu Glu
                165                 170
```

<210> SEQ ID NO 17
<211> LENGTH: 171
<212> TYPE: PRT
<213> ORGANISM: Homo sapiens

<400> SEQUENCE: 17

```
Met Ala Lys Phe Val Ile Arg Pro Ala Thr Ala Ala Asp Cys Ser Asp
1               5                  10                  15

Ile Leu Arg Leu Ile Lys Glu Leu Ala Lys Tyr Glu Tyr Met Glu Glu
            20                  25                  30

Gln Val Ile Leu Thr Glu Lys Asp Leu Leu Glu Asp Gly Phe Gly Glu
        35                  40                  45

His Pro Phe Tyr His Cys Leu Val Ala Glu Val Pro Lys Glu His Trp
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110
```

Leu Ser Gln Val Ala Met Arg Cys Arg Cys Ser Ser Met His Phe Leu
        115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Thr Glu Glu
                165                 170

<210> SEQ ID NO 18
<211> LENGTH: 158
<212> TYPE: DNA
<213> ORGANISM: Homo sapiens

<400> SEQUENCE: 18
ctggtgttta tccgtcactc gccgaggttc cttgggtcat ggtgccagcc tgactgagaa    60
gaggacgctc ccgggagacg aatgaggaac cacctcctcc tactgttcaa gtacaggggc   120
ctggtccgca agggaagaa aagcaaaaga cgaaaatg                            158

<210> SEQ ID NO 19
<211> LENGTH: 513
<212> TYPE: DNA
<213> ORGANISM: Homo sapiens

<400> SEQUENCE: 19
atggctaaat tcgtgatccg cccagccact gccgccgact gcagtgacat actgcggctg    60
atcaaggagc tggctaaata tgaatacatg gaagaacaag taatcttaac tgaaaaagat   120
ctgctagaag atggttttgg agagcacccc ttttaccact gcctggttgc agaagtgccg   180
aaagagcact ggactccgga aggacacagc attgttggtt ttgccatgta ctattttacc   240
tatgacccgt ggattggcaa gttattgtat cttgaggact tcttcgtgat gagtgattat   300
agaggctttg cataggatc agaaattctg aagaatctaa gccaggttgc aatgaggtgt   360
cgctgcagca gcatgcactt cttggtagca gaatggaatg aaccatccat caacttctat   420
aaacgcagag gtgcttctga tctgtccagt gaagagggt ggagactgtt caagatcgac   480
aaggagtact tgctaaaaat ggcaacagag gag                                513

<210> SEQ ID NO 20
<211> LENGTH: 579
<212> TYPE: DNA
<213> ORGANISM: Homo sapiens

<400> SEQUENCE: 20
ccacctcctc ctactgttca agtacagggg cctggtccgc aaagggaaga aaagcaaaag    60
acgaaaatgg ctaaattcgt gatccgccca gccactgccg ccgactgcag tgacatactg   120
cggctgatca aggagctggc taaatatgaa tacatggaag aacaagtaat cttaactgaa   180
aaagatctgc tagaagatgg ttttggagag caccccttt accactgcct ggttgcagaa   240
gtgccgaaag agcactggac tccggaagga cacagcattg ttggttttgc catgtactat   300
tttacctatg acccgtggat tggcaagtta ttgtatcttg aggacttctt cgtgatgagt   360
gattatagag gctttggcat aggatcagaa attctgaaga atctaagcca ggttgcaatg   420
aggtgtcgct gcagcagcat gcacttcttg gtagcagaat ggaatgaacc atccatcaac   480
ttctataaac gcagaggtgc ttctgatctg tccagtgaag agggtggag actgttcaag   540 atcgacaagg agtacttgct aaaaatggca acagaggag        579

<210> SEQ ID NO 21
<211> LENGTH: 667
<212> TYPE: DNA
<213> ORGANISM: Homo sapiens

<400> SEQUENCE: 21
ctggtgttta tccgtcactc gccgaggttc cttgggtcat agtgccagcc tgactgagaa        60
gaggacgctc ccggggacga ataaggaacc acctcctcct actgttcaag tacaggggcc       120
tggtccgcaa agggaagaaa agcaaaagac gaaaatggct aaattcgtga tccgcccagc       180
cactgccgcc gactgcagtg acatactgcg gctgatcaag gagctggcta aatatgaata       240
catggaagaa caagtaatct taactgaaaa agatctgcta aagatggtt ttggagagca       300
cccctttttac cactgcctgg ttgcagaagt gccgaaagag cactggactc cggaaggaca       360
cagcattgtt ggttttgcca tgtactattt tacctatgac ccgtggattg gcaagttatt       420
gtatcttgag gacttcttcg tgatgagtga ttatagaggc tttggcatag gatcagaaat       480
tctgaagaat ctaagccagg ttgcaatgag gtgtcgctgc agcagcatgc acttcttggt       540
agcagaatgg aatgaaccat ccatcaactt ctataaacgc agaggtgctt ctgatctgtc       600
cagtgaagag ggttggagac tgttcaagat cgacaaggag tacttgctaa aaatggcaac       660
agaggag        667

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcccaccggt ctcctctgtt gccattttta gc        32

<210> SEQ ID NO 23
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggatccgc cgccaccatg gctaaattcg tgatccg        37

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgggatccgc cgccaccatg gccgccgact gcagtgac        38

<210> SEQ ID NO 25
<211> LENGTH: 41
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 25
cgggatccgc cgccaccatg gacatactgc ggctgatcaa g                         41

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cgggatccgc cgccaccatg aaatatgaat acatggaaga acaag                     45

<210> SEQ ID NO 27
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgggatccgc cgccaccatg gctaaattcg tgatccgccc agccactaaa tatgaataca     60
tggaagaaca ag                                                         72

<210> SEQ ID NO 28
<211> LENGTH: 91
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgggatccgc cgccaccatg gctaaattcg tgatccgccc agccactgcc gccgactgca     60
gtgacataga tctgctagaa gatggttttg g                                    91

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgggatccct ggtgtttatc cgtcactcg                                       29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgggatccct ggtgtttatc cgtcactcg                                       29

<210> SEQ ID NO 31
<211> LENGTH: 116

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tagcagatct ttttcagtta agattacttg ttcttccatg tattcatatt tagccagctc      60
cttgatcagc cgcagtatgt cactgcagtc ggccattttc gtcttttgct tttctt        116

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaaaaagatc tgctagaaga tggtt                                           25

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcccaccggt ctcctctgtt gccattttta gc                                   32

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tagcagatct ttgtcactgc agtcggcggc                                      30

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgggatcccc acctcctcct actgttcaag ta                                   32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcccaccggt ctcctctgtt gccattttta gc                                   32

<210> SEQ ID NO 37

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgggatccgc cgccaccatg gtgaagctcg cgaagg                                   36

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcccaccggt agtcggttct gtgccttcca                                          30

<210> SEQ ID NO 39
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgggatccgc cgccaccatg acggctttca atctctttgt tg                            42

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcccaccggt ttcaaacttc gtcttctttc cttg                                     34

<210> SEQ ID NO 41
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgggatccgc cgccaccatg acggctttca atctctttgt tg                            42

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcccaccggt ttcacccttα ggtttggccc                                          30

<210> SEQ ID NO 43
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cgggatccgc cgccaccatg acggctttca atctctttgt tg                          42

<210> SEQ ID NO 44
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcccaccggt ttgacctttc tctccagtat agtacag                                37

<210> SEQ ID NO 45
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cgggatccgc cgccaccatg gaatcaaaaa ctctggtttt aagc                        44

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tcccaccggt ttcaccctta ggtttggccc                                        30

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgggatccgc cgccaccatg gtgagcaagg gcgag                                  35

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcccaccggt tcgagatctg agtccggact t                                      31

<210> SEQ ID NO 49
<211> LENGTH: 110
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 49
cgggatccgc cgccaccatg gctaaattcg tgatccgccc agccactgcc gccgactgca      60
gtgacatact gcggctgatc aaggagctgg ctatggtgag caagggcgag                110

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
taatacgact cactataggg atggctaaat tcgtgatccg                            40

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ccgtggtgcc cttgcgggca gaagtccaaa tgcgatcctt cgcaaccagg cagtggtaaa      60
ag                                                                    62

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
caagggcacc acggtcggat cctctaagcc aggttgcaat gag                        43

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcactcctct gttgccattt tt                                              22

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
taatacgact cactataggg atggctaaat tcgtgatccg                            40
```

```
<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcactcctct gttgccattt tt                                              22

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
taatacgact cactataggg tactgcggct gatcaaggag                           40

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tcactcctct gttgccattt tt                                              22

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
taatacgact cactataggg atggctaaat tcgtgatccg                           40

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctccttgtcg atcttgaaca gtc                                             23

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
taatacgact cactataggg tactgcggct gatcaaggag                           40

<210> SEQ ID NO 61
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctccttgtcg atcttgaaca gtc                                           23

<210> SEQ ID NO 62
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
taatacgact cactataggg gatctgctag aagatggttt tgg                     43

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctccttgtcg atcttgaaca gtc                                           23

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
taatacgact cactataggg tactgcggct gatcaaggag                         40

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaagttgatg gatggttcat tcc                                           23

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
taatacgact cactataggg gatctgctag aagatggttt tgg                     43

<210> SEQ ID NO 67
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gaagttgatg gatggttcat tcc                                              23

<210> SEQ ID NO 68
<211> LENGTH: 140
<212> TYPE: RNA
<213> ORGANISM: Homo sapiens

<400> SEQUENCE: 68
auggcuaaau ucgugauccg cccagccacu gccgccgacu gcagugacau acugcggcug      60
aucaaggagc uggcuaaaua ugaauacaug gaagaacaag uaaucuuaac ugaaaaagau     120
cugcuagaag augguuuugg                                                 140

<210> SEQ ID NO 69
<211> LENGTH: 513
<212> TYPE: RNA
<213> ORGANISM: Homo sapiens

<400> SEQUENCE: 69
auggcuaaau ucgugauccg cccagccacu gccgccgacu gcagugacau acugcggcug      60
aucaaggagc uggcuaaaua ugaauacaug gaagaacaag uaaucuuaac ugaaaaagau     120
cugcuagaag augguuuugg agagcacccc uuuuaccacu gccugguugc agaagugccg     180
aaagagcacu ggacuccgga aggacacagc auuguugguu uugccaugua cuauuuuacc     240
uaugacccgu ggauuggcaa guuauuguau cuugaggacu ucuucgugau gagugauuau     300
agaggcuuug gcauaggauc agaaauucug aagaaucuaa gccagguugc aaugaggugu     360
cgcugcagca gcaugcacuu cuugguagca gaauggaaug aaccauccau caacuucuau     420
aaaagaagag gugcuucuga ucuguccagu gaagagguu ggagacuguu caagaucgac     480
aaggaguacu ugcuaaaaau ggcaacagag gag                                  513

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
atggtgaagc tcgcgaaggc                                                  20

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gggaaagcag agggacagaa gc                                               22

<210> SEQ ID NO 72
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 72

His His His His His His
1               5

<210> SEQ ID NO 73
<211> LENGTH: 1089
<212> TYPE: DNA
<213> ORGANISM: Homo sapiens

<400> SEQUENCE: 73
```

| | | | | | |
|---|---|---|---|---|---|
| ggccaatgtt | caaatgcgca | gctcttagtc | gcgggccgac | tggtgtttat | ccgtcactcg | 60 |
| ccgaggttcc | ttgggtcatg | gtgccagcct | gactgagaag | aggacgctcc | cgggagacga | 120 |
| atgaggaacc | acctcctcct | actgttcaag | tacaggggcc | tggtccgcaa | agggaagaaa | 180 |
| agcaaaagac | gaaaatggct | aaattcgtga | tccgcccagc | cactgccgcc | gactgcagtg | 240 |
| acatactgcg | gctgatcaag | gagctggcta | aatatgaata | catggaagaa | caagtaatct | 300 |
| taactgaaaa | agatctgcta | aagatggttt | tggagagca | ccccttttac | cactgcctgg | 360 |
| ttgcagaagt | gccgaaagag | cactggactc | cggaaggaca | cagcattgtt | ggttttgcca | 420 |
| tgtactattt | tacctatgac | ccgtggattg | gcaagttatt | gtatcttgag | gacttcttcg | 480 |
| tgatgagtga | ttatagaggc | tttggcatag | gatcagaaat | tctgaagaat | ctaagccagg | 540 |
| ttgcaatgag | gtgtcgctgc | agcagcatgc | acttcttggt | agcagaatgg | aatgaaccat | 600 |
| ccatcaactt | ctataaaaga | gaggtgcttc | tgatctgtc | cagtgaagag | ggttggagac | 660 |
| tgttcaagat | cgacaaggag | tacttgctaa | aaatggcaac | agaggagtga | ggagtgctgc | 720 |
| tgtagatgac | aacctccatt | ctattttaga | ataaattccc | aacttctctt | gctttctatg | 780 |
| ctgtttgtag | tgaaataata | gaatgagcac | ccattccaaa | gctttattac | cagtggcgtt | 840 |
| gttgcatgtt | tgaaatgagg | tctgtttaaa | gtggcaatct | cagatgcagt | ttggagagtc | 900 |
| agatctttct | ccttgaatat | ctttcgataa | acaacaaggt | ggtgtgatct | taatatattt | 960 |
| gaaaaaaact | tcattctcgt | gagtcattta | aatgtgtaca | atgtacacac | tggtacttag | 1020 |
| agtttctgtt | tgattctttt | ttaataaact | actctttgat | ttaaaaaaaa | aaaaaaaaa | 1080 |
| aaaaaaaaa | | | | | | 1089 |

```
<210> SEQ ID NO 74
<211> LENGTH: 568
<212> TYPE: DNA
<213> ORGANISM: Sus scrofa

<400> SEQUENCE: 74
```

| | | | | | |
|---|---|---|---|---|---|
| ggggcctggt | gcgcaaaggg | aagaaaagca | aaagacgaaa | atggctaaat | tcgttatccg | 60 |
| cccggccact | gctgccgact | gcagtgatat | cctgcggctg | atcaaggaat | ggctaaata | 120 |
| cgaatacatg | gaagaacaag | taatattaac | tgaaaaagat | ctgctagaag | atggtttcgg | 180 |
| agagcacccc | ttctaccact | gcctggttgc | agaagtgccc | aaggagcatc | taactccgga | 240 |
| aggacacagc | attgttggtt | ttgccatgta | ctatttact | tatgacccat | ggattggcaa | 300 |
| actgttgtat | cttgaggact | tcttcgtgat | gagtgattat | agaggctttg | gcataggatc | 360 |
| agaaatcctg | aagaatctaa | gccaggttgc | aatgaaatgt | cgctgcagca | gcatgcactt | 420 |

```
cttggtagct gagtggaatg aaccatctat caacttctac aaaagaagag gtgcttctga    480
tctgtccagt gaagagggat ggagactctt caagatcgac aaggagtact tgctaaaaat    540
ggcagcagag gaatgaggcg tgccggtg                                       568
```

<210> SEQ ID NO 75
<211> LENGTH: 1201
<212> TYPE: DNA
<213> ORGANISM: Bos taurus

<400> SEQUENCE: 75

```
ggcgcgcgcg gctccagttg cagtgagctg cttgtcttac gttgttcgca gaggttcgcc     60
gggtcatggt gccatcctga ctgggaagag gacgctccgg ggagacgaat gaggaaccac    120
ctcctcctac tgttcaagta caggggcctg gtccgcaaag ggaagaaaag caaaagtcga    180
aaatggctaa attcgtgatc cgcccggcca ccgctgccga ctgcagtgac atcctgcggc    240
tgatcaagga attggctaaa tacgaataca tggaagagca agtaatgtta actgaaaaag    300
atctgctgga agacggtttc ggagagcacc ccttctacca ctgcttagtt gcagaagtgc    360
ccaaggagca cctgactccg gaaggacaca gcattgttgg ttttgccatg tactatttta    420
cctatgatcc atggatcggc aaactgttgt atcttgagga cttctttgtg atgagcgatt    480
atagaggctt tggcataggc tcagaaattc tgaagaagct aagccaggtt gcaatgaagt    540
gtcgctgcag cagcatgcac ttcttggtgg cagagtggaa tgaaccatct atcaacttct    600
acaaaagaag aggtgcctct gatctatcca gcgaagaggg atggagactc ttcaagatcg    660
acaaggagta cttgctaaaa atggcagcag aggagtgagg agtgctggtg tagaaaatga    720
cagcttccat tctatttag aataacttct caacttatct tgctttctct cctctttgta    780
gtgaaataat agaatgagca cccattccaa agctttatta ccagtggcgt tgttgcatgt    840
ttgaaataag gtctgtttaa gatggcaatc ttgtatacag gttggagaca gatttctctt    900
ttaacatctt ttgataaaca acaggtggta tgataatgtc tatgaaaaaa acttcattct    960
tgtgagtcat ttaaatgtgt acaatgtaca cactggtact tagagtttct gttttgattc   1020
tttttttaat aaagtacccct ttgatttaat taaaaaaaaa aaaaaaaaaa aaaaaaaaa   1080 aaaaaaaaaa aaaaaaaaaa aaaaaaaaaa aaaaaaaaaa aaaaaaaaaa aaaaaaaaaa   1140
aaaaaaaaaa aaaaaaaaaa aaaaaaaaaa aaaaaaaaaa aaaagaaaaa aaaaaaaaaa   1200
a                                                                   1201
```

<210> SEQ ID NO 76
<211> LENGTH: 513
<212> TYPE: DNA
<213> ORGANISM: Capra hircus

<400> SEQUENCE: 76

```
atggctaaat tcgtgatccg cccggccacc gctgccgact gcagtgacat cctgcggctg     60
atcaaggaat tggctaaata cgaatacatg gaagagcaag taatgttaac tgaaaaagat    120
ctgctagaag acggtttcgg agagcacccc ttctaccact gcttagttgc agaagtgccc    180
aaggagcacc tgactccgga aggacacagc attgttggtt ttgccatgta ctattttacc    240
tatgatccat ggattggcaa actgttgtat cttgaggact ctttgtgat gagcgattat    300 agaggctttg gcataggctc agaaattctg aagaagctaa gccaggttgc aatgaagtgt    360
cgctgcagca gcatgcactt cttggtggca gagtggaatg aaccatctat caacttctac    420
aaaagaagag gtgcctctga tctatccagc gaagagggat ggagactctt caagatcgac    480
```
aaggagtact tgctaaaaat ggcagcagat tag                       513

<210> SEQ ID NO 77
<211> LENGTH: 1054
<212> TYPE: DNA
<213> ORGANISM: Mus musculus

<400> SEQUENCE: 77
gtgctgcgca gtttccccga agtaagtttg ccagttttct gtcttatact gaggttcgcc      60
gggtcatggt gccagcctga ctgagaagag gacgctcccg ggaaacgaat gaggaaccac     120
ctcctcctgc tgttcaagta caggggcctg gtgcgcaaag ggaagaaaag caaaagacga     180
aaatggctaa atttaagatc cgtccagcca ctgcctctga ctgcagtgac atcctgcgac     240
tgatcaagga actggctaaa tatgaataca tggaagatca agtcatttta actgagaaag     300
atctccaaga ggatggcttt ggagaacacc ccttctacca ctgcctggtt gcagaagtgc     360
ctaaagagca ctggaccccc tgaaggacata gcattgttgg gttcgccatg tactatttta     420
cctatgaccc atggattggc aagttgctgt atcttgaaga cttcttcgtg atgagtgatt     480
acagaggctt tggtatagga tcagaaattt tgaagaatct aagccaggtt gccatgaagt     540
gtcgctgcag cagtatgcac ttcttggtag cagaatggaa tgaaccatct atcaacttct     600
acaaaagaag aggtgcttcg gatctgtcca gtgaagaggg atggaggctc ttcaagattg     660
acaaagagta cttgctaaaa atggcagcag aggagtgagg cgtgccggtg tagacaatga     720
caacctccat tgtgctttag aataattctc agcttcccctt gctttctatc ttgtgtgtag     780
tgaaataata gagcgagcac ccattccaaa gctttattac cagtgacgtt gttgcatgtt     840
tgaaattcgg tctgttttaaa gtggcagtca tgtatgtggt ttggaggcag aattcttgaa     900
catcttttga tgaagaacaa ggtggtatga tcttactata aagaaaaac aaaacttcat     960
tcttgtgagt catttaaatg tgtacaatgt acacactggt acttagagtt ctgttttga    1020
ttctttttt tttaaataaa ctactctttg attt                                 1054

<210> SEQ ID NO 78
<211> LENGTH: 1195
<212> TYPE: DNA
<213> ORGANISM: Rattus norvegicus

<400> SEQUENCE: 78
ggggaacaga gggcggtgct tcctcaggct tgcatcttta ctggtcgaga tctctatgtc      60
tcttagtccg ggaggagct tctgcatact taaaaggcac tgtcttgcca ctgtagctgc     120
gcagctcccc agagtaagtc tgccagtttt ctgtcttcta ctgaggttcg ccgggtcatg     180
gtgccagcct gactgagaag aggacgctcc cgggaaacga atgaggaacc acctcctcct     240
gctgttcaag tacaggggcc tggtgcgcaa agggaagaaa agcaaaagac gaaaatggct     300
aaatttaaga tccgtccagc cactgcctct gactgcagtg acatcctgcg actgatcaag     360
gaactggcta aatatgaata catggaagat caagtagttt aactgagaa agatctctta     420
gaggatggtt ttggagagca ccccttctac cactgcctgg ttgcagaagt gcctaaagag     480
cactggaccc ctgaaggaca cagcattgtt ggttttgcca tgtactattt tacctatgac     540
ccatggattg gcaagttact gtatcttgaa gacttctttg tgatgagtga ttaccgaggc     600
tttggtatag gatcagaaat tttgaagaat ctaagccagg ttgctatgaa gtgtcgctgc     660
agcagtatgc acttcttggt agcagagtgg aatgaaccat ctatcaactt ctacaaaaga     720

| | | | | |
|---|---|---|---|---|
| agaggtgctt | cggatctgtc | cagtgaagag | ggatggagac | tattcaagat tgacaaagaa | 780 |
| tacttgctaa | aaatggcagc | agaggagtga | ggtgtgccgg | tatagacaat gaccacctcc | 840 |
| attgtgcttt | agaataaatt | ctcaacttcc | cttgctttct | atctcgtttg tagtgaaata | 900 |
| atagagtgag | catccattcc | aaagctttat | taccagtggc | gttgttgcat gtttgaaatt | 960 |
| cggtctgttt | aaaatggcag | tcatgtatgt | ggtttggagg | cagaattctt gaacatcttt | 1020 |
| tgatgaagaa | caaggtggta | tcatctttat | atatgaaaaa | caaaacttca ttcttgtgag | 1080 |
| tcatttaaat | gtgtacaatg | tacacactgg | tacttagagt | ttctgttttg attctttttt | 1140 |
| aaaaaaataa | actactcttt | gattcgaaaa | aaaaaaaaaa | aaaaaaaaa aaaaa | 1195 |

<210> SEQ ID NO 79
<211> LENGTH: 516
<212> TYPE: DNA
<213> ORGANISM: Cricetulus griseus

<400> SEQUENCE: 79

| | | | | |
|---|---|---|---|---|
| atggctaaat | tcaagatccg | tccagccact | gcctctgact | gcagtgacat cctgcgactg | 60 |
| atcaaggaac | tggctaaata | tgaatacatg | gaagatcaag | taatgttaac cgagaaagat | 120 |
| ctcctagagg | atggttttgg | agaacacccc | ttctaccact | gcctgattgc agaagtgcct | 180 |
| aaagagcact | ggacccctga | aggacacagc | attgttggtt | cgccatgta ctatttacc | 240 |
| tatgacccat | ggattggcaa | gttactttat | cttgaagact | ctttgtgat gagtgattac | 300 |
| agagggtttg | gcataggatc | agaaattttg | aagaatctaa | gccaggttgc catgaagtgt | 360 |
| cgctgcagca | gtatgcactt | cttggtagca | gaatggaatg | aaccatctat caacttctac | 420 |
| aaacgaagag | gtgcttctga | cctgtccagt | gaagagggat | ggaggctctt caagattgac | 480 |
| aaagagtact | tgctaaaaat | ggcagcagag | gagtaa | | 516 |

<210> SEQ ID NO 80
<211> LENGTH: 1021
<212> TYPE: DNA
<213> ORGANISM: Gallus gallus

<400> SEQUENCE: 80

| | | | | |
|---|---|---|---|---|
| cgtcgccgaa | gtcggtgggt | gagtcgtctg | cctgctgaac | gccgccggga catgctcgca | 60 |
| gcctgactga | ccgcaggtgg | ccgccgcgcc | cgggacacga | atgaagaaac agctgctcct | 120 |
| cctgttcaca | caccggggac | tcgtcagccg | agggggccgc | aggggaaac gccgtcgaaa | 180 |
| atggcttcgt | tcagtatccg | cgccgcgcgt | cccgaggact | gctccgacct gctgcgactg | 240 |
| atcaaggaac | tagccaagta | cgaggacatg | gaggatcaag | tggtgctaac cgagaaagag | 300 |
| ctgcttgagg | acggctttgg | cgagcacccg | ttctaccact | gtctcgttgc ggaggtgccg | 360 |
| aaagaacagt | ggtcgtccga | agggcacagc | attgtgggct | ttgctatgta ttacttcact | 420 |
| tacgatccat | ggattggaaa | gctgttgtat | cttgaagatt | tctatgtgat ggctgagtac | 480 |
| agaggacttg | gcattggatc | agaaatcctg | aagaatttga | gtcaggttgc tgtcaagtgc | 540 |
| cgctgcagca | gtatgcactt | cctagttgca | gagtggaatg | agccctccat caggttctac | 600 |
| aagaaaggg | gtgcctctga | tctgtccact | gaagagggct | ggaggctctt caaaatcgac | 660 |
| aaagagtatc | tcttgaagat | ggcaacagaa | gagtagtgag | agaaggttcc agcgactaaa | 720 |
| ctcttcaaat | gaatatacat | gctctctgaa | taaactcctt | cttgctttct gtgttcatag | 780 |
| tggaataaaa | tagtgtggat | gctaatacta | tgcaactgtg | gtcatagagt aattggtact | 840 |
| gtgagctgga | gtggaggcat | ctcaagttga | atatgtgctt | gtatccatcc tttaccagtg | 900 |

| | |
|---|---|
| tgggcttgta atctttgtat atgaaaactt cattcttgta agtgtcattc aaatgtgtac | 960 |
| aatgtacaca ctggtagggt ttgttttatt tccttttata agaataaata gttttcactc | 1020 |
| t | 1021 |

<210> SEQ ID NO 81
<211> LENGTH: 1061
<212> TYPE: DNA
<213> ORGANISM: Xenopus laevis

<400> SEQUENCE: 81

| | |
|---|---|
| cggacgcgtg ggcttttgtt atcacggtgg ctgcagcgat tgaactctgt cgagtcaggg | 60 |
| tcccagactg actaaggaga gcaagctcct gggaagcgaa tgaagaaaca cgtcctacta | 120 |
| ctcttcacat acagaggact tgtcaggaaa ggaaaaaaga gcaagagaag aaaatggcca | 180 |
| agtttatcat acgatccgct aatgccgggg actgtaagga tatattgcga ctcataaagg | 240 |
| aactggcaaa atatgaggaa atggagaacc aagttgtcct aactgagaaa gatctgcttg | 300 |
| aagacggatt tggagaacat ccattttacc actgtcttgt tgctgaagtg cctaaggaga | 360 |
| ccgagagtgt cgatgggtat acagttgttg ggtttgcaat gtactacttc acatatgacc | 420 |
| cgtggattgg aaaattgctt tatctggaag acttctttgt gatggatgaa ttcagaggtt | 480 |
| ttggcatggg atcagagata ttcaagcact gggtcaaat tgcgatgaag tgtcgctgca | 540 |
| gcagcatgca cttcctggtt gcagaatgga atgagccatc cataaagttc tacaagagac | 600 |
| gtggcgcatc tgacctttct acagaagaag atggcgcct cttcaaaatc gataaagagt | 660 |
| acttgtgtaa acttgcagct gaagagtgag aactcttcca gaggcagcaa atatctcaat | 720 |
| aaaagaataa ccttcttgat tgtttgcatg tcattattgt agtttaattg tagagtagct | 780 |
| actccaaagc tttattacca gtgacattga aacgtgtctc cagatctcct agcaaaacta | 840 |
| ttgtggcaac attttccaag cgttcttcaa accttagttt cccagttgtc tgtattatat | 900 |
| gtaacttcat tgttgtaagt catttgtgta caatgtacac actggtatgt aggtttctat | 960 |
| ttataccatt aacctgtttt tatgaattaa aaaagcagta tttgttctaa aaaaaaaaa | 1020 |
| aaaaaaaaaa aaaaaaaaa aaaaaaaaa aaaaaaaaa a | 1061 |

<210> SEQ ID NO 82
<211> LENGTH: 913
<212> TYPE: DNA
<213> ORGANISM: Pelophylax ridibunda

<400> SEQUENCE: 82

| | |
|---|---|
| aaaaaagagc aagagacgaa aatggccaat tatgtcatac gatcagctgt acccggagac | 60 |
| tgtaaagaca ttctgcgact cataaaggaa ttggctaaat atgaagaaat ggaaaaccaa | 120 |
| gtagtgttaa ctgagaaaga tcttttagaa gatggctttg gagaacatcc tttctaccac | 180 |
| tgtcttgttg ctgaagtacc aaaagagaac cagactattg atggatacac cattgtgggg | 240 |
| tttgctatgt actacttcac atatgaccca tggataggga agcttctgta cttggaagac | 300 |
| ttctttgtca tgaatgaatt cagaggatct ggcatcgggt cagatatatt caagcacttg | 360 |
| agtcagattg ctgtaaagtg ccgttgtagc agcatgcact tcctggtggc cgaatggaat | 420 |
| gagccatcga tcaggttcta taaagacgt ggagcatcag atctgtccac tgaagaaggc | 480 |
| tggcgcctct ttaaaattga caaggagtac ctgtgcaaga tggcggctga ggagtgaact | 540 |
| cagtgcctcc aagaagaaat tgttacttac aaataaaatt gcttttcttt tgcctgctta | 600 |

| | |
|---|---|
| gtattcctttt agcgtcttgc atgcaactaa ttcaaaagct atagtacagg ggcattatag | 660 |
| catgcaattg tcaccttac cccccccccc ccccccctct gcttttttcag ctatgccctt | 720 |
| catggcccaa gactgtttaa agagccctaa aaataagatc ctcagttgta tgtgtaatat | 780 |
| atgttacttc attcttgtaa gtcatttgat tgtgtacagt gtacacactg gtatttaggg | 840 |
| tttttgtata attaaccagt ttttttatt ttaattaaag agcagcatgt gttgtactat | 900 |
| gaaaaaaaaa aaa | 913 |

<210> SEQ ID NO 83
<211> LENGTH: 1010
<212> TYPE: DNA
<213> ORGANISM: Rana catesbeiana

<400> SEQUENCE: 83

| | |
|---|---|
| gggggggagtc tctgccgagt cagggtccca gactgactaa ggagcggaag cccctgggaa | 60 |
| gcgaatgaag aaacaccttc tactactctt cacattcaga ggtctagtca gaaaaggaaa | 120 |
| aaagagcaag aaacgaaaat ggccaattat accatacgat cagctgtgcc cggagactgt | 180 |
| aaagacattt tgcgacttat aaaggaattg gctaaatatg aagaaatgga aaaccaagta | 240 |
| gtgttaactg agaaagatct tttagaagat ggctttgggg aacatccttt ctaccactgt | 300 |
| cttgttgctg aagtaccaaa agagaaccag actattgatg gatacaccat tgttgggttt | 360 |
| gctatgtact acttcacata tgacccatgg ataggaaagc ttctgtattt ggaagacttt | 420 |
| tttgtcatga atgaattcag aggatcaggc atcgggtcag atatattcaa gcatttgagt | 480 |
| cagattgctg taaagtgccg ttgtagcagc atgcacttcc tggtggccga atggaatgag | 540 |
| ccatcaatca ggttctataa agagacgtgga gcatcagatc tgtccactga gaaggttgg | 600 |
| cgcctctttta aaattgacaa ggagtacctg tgcaagatgg cggctgagga gtgaactcag | 660 |
| tgcccccaa gaagaaattg ttacttacaa ataaaattgc ttttcttttg cctgcttagt | 720 |
| attcttttagt gtcttgcatg gcaactaatt caaaagcttt agtaccagtg gcattgtaac | 780 |
| atacaattgt cacccccccc gcccctgct tttttagca atgccattca cggcccaaga | 840 |
| ctgtttaaag agccctaaaa ataagattct cagttgtatg tgtatatgt taacttcatt | 900 |
| cttgtaagtc atttgattgt gtacagtgta cacactggta tttagggttt ttgtataatt | 960 |
| aaccagttt tattttattt taattaaaaa ccagcatgtg ttgtactatc | 1010 |

<210> SEQ ID NO 84
<211> LENGTH: 818
<212> TYPE: DNA
<213> ORGANISM: Danio rerio

<400> SEQUENCE: 84

| | |
|---|---|
| acaaatgaac cagagctgct gcatgtgtgt ccgagcagaa agcagatctc agacctgtag | 60 |
| ctgagggtga acctctgaga agcggatgaa gaaacaaata attctacact tcacataccg | 120 |
| aggactagtc agcaaaggaa aaaagagcaa gagaagaaga agaaaatggc cagttatata | 180 |
| ttacggaaag ccgaacccaa ggacgtgtct gacatactgc gactcataaa ggaattggcg | 240 |
| aaatttgagg aaatggagga ccaagttatt ctcactgaaa aagatctgct ggaggacggt | 300 |
| tttggagatc atcctttcta tcactgtatg gtggctgaag tggccaaaca gcatcagagc | 360 |
| gccgacggtc atgtgatcgt tggctttgcc atgtattatt tcacctatga cccctggatt | 420 |
| gggaaactgc tctacctgga agatttctac gtcatgaagg agtatcgggg tttcgggatt | 480 |
| gggtctgaaa tcctgaagaa actcagtcag acggcggtga ggacgcgctg cagtagtatg | 540 |

```
cacttcatag tggcagagtg gaacaccacc tccattgagt tctacaagcg gcgaggagcg    600
tccgacctct cgcacgagga gggatggaga ctcttcaaga tcgacaaaca gagtctcctc    660
aagatgacca gcgaggagtg aagcgctctg gaggaccacc tgctgttcag tttagtggac    720
acaactttaa aagtcatggt gcatctaaac acatgctgcg tcccaattcg catactatcc    780
atcctatgta ggaatgttcc aaaaaaaaaa aaaaaaaa                            818
```

SSAT MRNA TRANSLATION REPRESSION AND ACTIVATION

CROSS-REFERENCE TO RELATED APPLICATIONS

The benefit of the filing dates of U.S. Provisional Patent Application No. 61/530,498, filed Sep. 2, 2011, and U.S. Provisional Application No. 61/680,497, filed Aug. 7, 2012, is hereby claimed. The entire disclosures of the aforesaid applications are incorporated herein by reference.

REFERENCE TO GOVERNMENT SUPPORT

This invention was made with government support under grant No. RO1AI064017 awarded by the National Institutes of Health. The government has certain rights in the invention.

SEQUENCE LISTING

The instant application contains a substitute Sequence Listing which has been submitted in ASCII format via EFS-Web and is hereby incorporated by reference in its entirety. Said ASCII copy, created on Sep. 20, 2016 is named Second_Substitute_35926_0422_00_US_509753_SL and is 61,985 bytes in size.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

Polyamines are small positively charged molecules present in all cells. Common polyamines include putrescine, spermidine and spermine. Polyamines function in a myriad of biochemical processes including polynucleotide stabilization, transcription and translation regulation, enzyme activity modulation, iron channel regulation, and oxidative stress responses (Pegg et al., 1982, The American Journal of Physiology 243(5):C212-221; Wang et al., Polyamine cell signaling: physiology, pharmacology, and cancer research, Humana Press, Totowa, N.J., 2006). Polyamines are essential for cell growth; rates of synthesis and content both increase with increased cell proliferation. As a consequence, manipulation of polyamine metabolism has been an anticancer strategy, with pool depletion in tumor cells used as a surrogate marker of efficacy (Kramer and Gerner, 2004). For instance, inhibitors of the rate limiting enzymes have been evaluated clinically as anticancer and chemopreventive agents (Gerner et al., 2004, Nat. Rev. Cancer 4(10):781-792).

Because polyamines affect so many cell processes, control of intracellular pools is critical and levels are maintained within a relatively narrow range by shifts in anabolism/catabolism as well as import/export (Alhonen-Hongisto et al., 1980; Porter and Bergeron, 1988). Translation control mechanisms are known to be involved in eukaryotic cell regulation of polyamine metabolism (Coffino, 2001, Nature Reviews Molecular Cell Biology 2(3):188-194; Pegg, 2006, J Biol Chem. 281(21):14529-14532; Raney et al., 2002, J Biol Chem. 277(8):5988-5994).

Ornithine decarboxylase (ODC) is the rate-limiting anabolic enzyme. ODC is regulated by a translational control mechanism that responds to polyamine levels and involves a strong secondary structure in the mRNA 5' UTR, fast protein turnover, and control of homodimerization required for enzymatic activity (Pegg, 2006, J Biol Chem. 281(21):14529-14532). ODC "antizyme" controls ODC by blocking homodimerization and increasing turnover; antizyme itself is regulated by a translational control mechanism involving polyamine-induced ribosomal frame-shifting (Coffino, 2001, Nature Reviews Molecular Cell Biology 2(3):188-194).

Spermidine/spermine acetyltransferase (SSAT) is the principal catabolic regulator. SSAT uses acetyl-CoA to acetylate spermidine and spermine. The acetylation reduces the positive charge of spermidine and spermine, thus making them inert and facilitating their excretion. SSAT has an extremely low basal expression and turns over faster than ODC, yet is quickly inducible to high activity when polyamines are in excess (Casero et al., 2009, Biochemical Journal 421:323-338). Experimental manipulations that increase SSAT transcription produce only limited increases in translation and, conversely, increases in translation by stimulation with polyamines can occur with little change in transcription (Fogel-Petrovic et al., 1996, FEBS letters 391 (1-2):89-94; Parry et al., 1995, The Biochemical Journal 305 (Pt 2):451-458). The postulation has been that SSAT mRNA is maintained in a translationally repressed status such that cells are able to respond quickly to changes in polyamine levels by releasing the translational repression. There is some evidence to support this, but there is little information regarding the underlying molecular mechanism. Data indicate that the 3' and 5' UTRs are not involved, the 5' terminus of the coding region is involved, and a repressor protein is likely to be involved, though to date, none has been identified (Butcher et al., 2007, J Biol Chem. 282:28530-28539; Parry et al., 1995, The Biochemical Journal 305 (Pt 2):451-458). Data also suggest that increased polyamine flux consequent to SSAT induction can restrict tumor growth, for instance, in prostate adenocarcinoma (Kee et al., 2004, J Biol Chem 279(38):40076-83, Epub 2004 Jul. 13; Babbar et al., 2011. Recent Results Cancer Res. 2011; 188:49-64; Simoneau et al., 2008, Cancer Epidemiol Biomarkers Prev. 2008 February; 17(2):292-9).

During recovery and preservation organs are anoxic, as they are in ischemia, and following transplantation they are reperfused. Reperfusion may result in ischemia-reperfusion injury (IRI). IRI may also arise following resumption of blood flow to an organ when blood flow is interrupted, such as following brain injury or myocardial infarction. IRI is estimated to be responsible for 10% of early graft loss in the case of transplanted livers (Amersi et al., J. Clin. Invest. 1999; 104:1631).

Agents that repress SSAT translation may possess therapeutic activity in disorders or diseases characterized at least in part by increased SSAT activity. Exemplary diseases having such increased SSAT activity include ischemia-reperfusion injury, stroke and myocardial infarction. In particular, prevention of SSAT translation provides an opportunity for prevention of IRI, including IRI after liver or renal transplant, myocardial infarction (Han et al. (2009) Int J Cardiol 132:142-144; Zahedi et al. (2009) Am J Physiol Gastrointest Liver Physiol 296:G899-G90) and brain injury (Zahedi et al. (2010) J Neurotrauma 27:515-525).

In each of these conditions, ischemic injury has been suggested to increase SSAT activity to a level that causes cell toxicity. Studies with SSAT knockout animals have confirmed that renal ischemia-reperfusion injury is at least partially SSAT dependent because SSAT knockout animals have very mild injury compared to wild type animals (Zahedi et al. 2009).

Ischemic reperfusion injuries such as acute renal failure, acute liver failure, stroke, and myocardial infarction are prevalent causes of morbidity and mortality. In particular, kidney ischemic reperfusion injury is the leading cause of acute renal failure and dysfunction of transplanted kidneys. Treatment options for IRI are few.

There is also an unmet need in the art to identify the mechanism underlying translational repression in eukaryotic cell regulation of polyamine metabolism and to identify agents that relieve translational repression. There is also a need to identify agents that increase or decrease translation of SSAT for use in therapies where increased or decreased expression of SSAT is desired. The present disclosure addresses this need.

SUMMARY

The following summary is not an extensive overview. It is intended to neither identify key or critical elements of the various embodiments, not delineate the scope of them.

Provided is an isolated nucleic acid comprising a first sequence encoding the polypeptide of SEQ ID No. 1, wherein the nucleotide sequence encoding Arg142 of SEQ ID No. 1 is CGC. In an embodiment, the first sequence encoding the polypeptide of SEQ ID No. 1 is SEQ ID NO. 2. The first sequence encoding the polypeptide of SEQ ID No. 2 may be selected from the group consisting: SEQ ID No. 3, SEQ ID No. 4, SEQ ID No. 5, SEQ ID No. 5, SEQ ID No. 6, SEQ ID No. 7, SEQ ID No. 8, and SEQ ID No. 9. In an embodiment, the isolated nucleic acid is RNA or DNA.

The isolated nucleic acid may further comprise a second sequence encoding a reporter polypeptide, wherein the first sequence is operably linked to the second sequence. In an embodiment, the isolated nucleic comprising a second sequence encoding a reporter polypeptide is RNA.

The isolated nucleic acid may further comprise a nucleotide sequence encoding a 5' untranslated region of an mRNA encoding a spermidine/spermine acetyltransferase operably linked 5' to the first sequence, wherein the 5' untranslated region comprises a Kozak sequence and does not comprise an open reading frame. In an embodiment, the sequence encoding the 5' untranslated region comprises nucleotides 1 to 66 of SEQ ID No. 20 or nucleotides 1 to 155 of SEQ ID No. 21.

A vector comprising an expression cassette wherein said expression cassette comprises the isolated nucleic acid is provided. A kit comprising the isolated nucleic acid or a vector comprising the isolated nucleic is provided.

Also provided is an isolated nucleic acid comprising a first sequence encoding the amino acids 1-26 of SEQ ID No. 1 operably linked to a second sequence encoding amino acids 134-171 of SEQ ID No. 1, wherein the nucleotide sequence encoding Arg142 of SEQ ID No. 1 is CGC. A vector comprising an expression cassette wherein said expression cassette comprises the isolated nucleic acid is provided. A kit comprising the isolated nucleic acid or a vector comprising the isolated nucleic is provided.

Further provided is a method for identifying an agent that increases translation of an mRNA encoding spermidine/spermine acetyltransferase. The mRNA is a nucleic acid comprising a first sequence encoding the polypeptide of SEQ ID No. 1, wherein the nucleotide sequence encoding Arg142 of SEQ ID No. 1 is CGC. The method comprises the steps of assessing the level of translation of an mRNA in the absence of a candidate agent to obtain a reference level of translation; and assessing the level of translation of the mRNA in the presence of the candidate agent to obtain a test level of translation. The candidate agent is identified as an agent that increases translation if the test level of translation is greater than the reference level of translation.

Also provided is a method for identifying an agent that decreases translation of an mRNA encoding spermidine/spermine acetyltransferase. The mRNA is a nucleic acid comprising a first sequence encoding the polypeptide of SEQ ID No. 1, wherein the nucleotide sequence encoding Arg142 of SEQ ID No. 1 is CGC. The method comprises the steps of: assessing the level of translation of an mRNA in the absence of a candidate agent to obtain a reference level of translation; and assessing the level of translation of the mRNA in the presence of the candidate agent to obtain a test level of translation. The candidate agent is identified as an agent that decreases translation if the test level of translation is less than the reference level of translation.

In some embodiments of the methods for identifying an agent, the mRNA further comprises a second sequence encoding a reporter polypeptide, wherein the first sequence is operably linked to the second sequence. The reporter polypeptide may be selected from the group consisting of luciferase and green fluorescent protein. In some embodiments, the first sequence of the mRNA encodes SEQ ID NO. 2. In some embodiments, assessing the level of translation is a cell-based assay.

In an alternative embodiment of the methods for identifying an agent, the mRNA does not encode a functional SSAT, wherein the predicted secondary structure of the mRNA encoding the mutated SSAT is substantially the same as the predicted secondary structure for SEQ ID No. 19. In some embodiments of the methods for identifying an agent, the mRNA comprises a sequence encoding amino acids 1-26 of SEQ ID No. 1, 2 or 3 operably linked to a sequence encoding amino acids 134-171 of SEQ ID Nos. 1, 2 or 3, wherein the codon for Arg142 (numbering as for SEQ ID No. 1) is CGC, and wherein the predicted secondary structure of the sequence encoding amino acids 1-26 of SEQ ID No. 1, 2 or 3 is a stem loop and the predicted secondary structure of the sequence encoding amino acids 134-171 of SEQ ID Nos. 1, 2 or 3 is the same as the secondary structure predicted for nucleotides 400-513 of SEQ ID No. 19.

Further provided is a method of increasing the amount of SSAT polypeptide in a cell. The method comprises comprising administering to a cell a vector comprising an expression cassette wherein said expression cassette comprises an nucleic acid comprising a first sequence encoding the polypeptide of SEQ ID No. 1, wherein the nucleotide sequence encoding Arg142 of SEQ ID No. 1 is CGC the nucleic acid of claim 1, wherein expression of said nucleic acid increases the amount of SSAT polypeptide in the cell. The cell may be in vivo, in vitro or ex vivo. In an embodiment, the cell may be a cell of a cellular proliferative disorder or disease. Exemplary cells of a cellular proliferative disorder or disease include a melanoma cell or a prostate carcinoma cell. In some embodiments, the cell is a human cell.

A method for preventing or treating ischemia-reperfusion injury in organs or tissue for transplantation is provided. The method comprises contacting organs or tissue with an effective amount of a composition comprising an agent that decreases translation of an mRNA encoding spermidine/spermine acetyltransferase, which agent has been identified to decrease said translation by the method comprising: (1) assessing the level of translation of an indicator RNA in the absence of the agent to obtain a reference level of translation, wherein the indicator RNA is a nucleic acid comprising a first sequence encoding the polypeptide of SEQ ID No. 1, wherein the nucleotide sequence encoding Arg142 of SEQ ID No. 1 is CGC; (2) assessing the level of translation of the indicator RNA in the presence of the agent to obtain a test level of translation, wherein the agent is identified as an agent that decreases translation of the indicator RNA if the test level of translation is less than the reference level of translation.

In embodiments, the identified agent decreases the level of translation of the indicator RNA by at least about 85% over the reference level of translation. In other embodiments, the identified agent decreases the level of translation by at least about 86%, 87%, 88%, 89%, 90%, 91%, 92%, 93%, 94%, 95%, 96%, 97%, 98%, 99% or 100%.

In another embodiment, a method for reducing ischemia-reperfusion injury in organs or tissue for transplantation comprises contacting organs or tissue with an effective amount of a composition comprising at least one agent that decreases translation of an mRNA encoding spermidine/spermine acetyltransferase, wherein said at least one agent is selected from the group consisting of astemizole, terfenadine, vanoxerine, suloctidil, digitoxigenin, digoxin, parthenolide, chrysene-1,4-quinone, sertindole, lanatoside C, beta-escin, alexidine, fluspirilen, thonzonium, toremifene, proscillaridin A, pyrvinium, aripiprazole, and pharmaceutically acceptable salts thereof. In some embodiments, the agent is vanoxerine dihydrochloride, alexidine dihydrochloride, thonzonium bromide or pyrvinium pamoate, and combinations thereof.

In some embodiments, the composition for reducing ischemia-reperfusion injury comprises a saline solution. In other embodiments, the for reducing ischemia-reperfusion injury composition comprises an organ preservation solution.

In some embodiments, the composition for reducing ischemia-reperfusion injury is contacted with the organ or tissue in the body of a donor of the organ or tissue. In other embodiments, the composition for reducing ischemia-reperfusion injury is contacted with the organ or tissue in the body of a recipient of the organ or tissue. In other embodiments, the composition for reducing ischemia-reperfusion injury is contacted with the organ or tissue ex vivo.

In some embodiments, the organ or tissue comprises organs or tissue comprising heart, liver, kidney, lung, pancreas, intestine, eyeball, cornea, bone, skin, vasculature or heart valve.

A composition for preventing or treating ischemia-reperfusion injury in organs or tissue for transplantation is provided. The composition comprises an organ preservation solution containing an effective amount of an agent that decreases translation of an mRNA encoding spermidine/spermine acetyltransferase in said organs or tissues, said agent selected from the group consisting of astemizole, terfenadine, vanoxerine, suloctidil, digitoxigenin, digoxin, parthenolide, chrysene-1,4-quinone, sertindole, lanatoside C, beta-escin, alexidine, fluspirilen, thonzonium, toremifene, proscillaridin A, pyrvinium, aripiprazole, and combinations thereof, and pharmaceutically acceptable salts thereof.

BRIEF DESCRIPTION OF THE DRAWINGS

For the purpose of illustrating the methods disclosed herein, there are depicted in the drawings certain embodiments. However, the methods and related products are not limited to the precise arrangements and instrumentalities of the embodiments depicted in the drawings.

FIGS. 1A and 1B depict an alignment of amino acid sequences of spermidine/spermine acetyltransferase homologs (SEQ ID NOs. 3-14). A consensus sequence (SEQ ID No. 1) is also depicted based on the alignment. Asterisks indicate invariant amino acid positions in SEQ ID Nos. 3-14.

FIG. 2 is a table of the general type of amino acid found at the variable residues of SEQ ID No. 1 and exemplary amino acids for each X residue, based on SEQ ID NOs. 3-14.

FIGS. 3A and 3B depict an alignment of amino acid sequences of spermidine/spermine acetyltransferase mammalian homologs (SEQ ID Nos. 3-9). A consensus sequence (SEQ ID No. 2) is also depicted based on the alignment. Asterisks indicate invariant amino acid positions in SEQ ID Nos. 3-9.

FIG. 4 is a table of the general type of amino acid found at the variable residues of SEQ ID No. 2 and exemplary amino acids for each X residue based on SEQ ID Nos. 3-9.

FIG. 5 depicts a cDNA sequence (SEQ ID No. 15) that is an exemplary SSAT mRNA. The ATG initation codon for the SSAT coding region is underlined, as is the termination codon TGA. The codon for Arg142 is double-underlined.

FIGS. 6A and 6B depict the nucleotide sequence of the coding sequence (SEQ ID No. 16) and the corresponding amino acid sequence (SEQ ID No. 17) of human SSAT.

FIG. 7 depicts the 5' UTR sequence of the human SSAT mRNA (SEQ ID No. 18) in FIG. 5. The initiation codons of the two upstream open reading frames (uORFs) are underlined. The initiation codon of the SSAT coding sequence is bolded.

FIGS. 8A, 8B and 8C depict exemplary nucleic acid sequences of the invention. In the sequences, the initiation codon of the SSAT coding sequence is underlined. The CGC codon for Arg142 is double-underlined. The uORF initations codons are italicized and underlined. FIG. 8A depicts a coding sequence for human SSAT starting with the initiation codon, but lacking the termination codon. The codon encoding Arg142 is CGC (SEQ ID No. 19). FIG. 8B depicts a sequence (SEQ ID No. 20) which contains the sequence of FIG. 8A and further include 5' UTR nucleotides −66 to −1 of the human SSAT mRNA. FIG. 8C depicts a sequence (SEQ ID No. 21) which contains the sequence of FIG. 8A and further include 5' UTR nucleotides −155 to −1 of the human SSAT mRNA, in which the two uORF initiation codons are removed by mutation to ATA (underlined and italicized).

FIGS. 9A, 9B and 9C relate to identification of SSAT RNA binding proteins that repress translation. FIG. 9A depicts schematically the SSAT RNA bait molecule (bottom schematic). The Mfold predicted secondary structure for the SSAT RNA bait molecule is also shown (top schematic). The chimeric RNA contains the first 170 bp and last 181 bp of the human SSAT coding region linked to a streptomycin-binding RNA aptamer. FIG. 9B is an image of proteins separated by SDS-PAGE, and stained with Sypro Ruby. The proteins (lane 2) were eluted from a Sepharose-streptomycin column on which the RNA bait molecule was immobilized and incubated with a HEK293T cell lysate. A control column containing aptamer-linked GFP RNA did not bind any proteins (lane 1). Enolase 1 (ENO1); Y box protein 1 (YBX1); DNA-binding protein A (CSDA); La protein (SSB); ATPdependent RNA helicase A (DHX9); and nucleolin (NCL). FIG. 9C is an image of a Western blot. RNA-interacting proteins were individually knocked down and the effect of recombinant SSAT (rSSAT) expression assayed by Western blot using actin as the loading control. Lanes 1-6 contain proteins from cells treated with the indicated siRNA. Lane 7 is a negative control based on cells treated with non-targeting siRNA. Lane 8 is a positive control based on cells exposed to $N^1$-$N^{11}$ diethylnorspermine (DENS).

FIG. 10A is a schematic of nucleolin polypeptide with amino acid numbers noted. N-term=N-terminal region; RRM1-RRM4=RNA recognition motifs 1-4; GAR=Glycine/Arginine rich domain. FIG. 10B is an image of a Western blot using an anti-His tag monoclonal antibody confirmed expression of nucleolin fragments by transiently transfected cells. FIG. 10C is an image of a Western blot analysis with anti-His tag antibody showing nucleolin fragment binding to SSAT RNA column. FIG. 10D is an image of a Western blot of lysates of HEK293T that were exposed to 2 mM spermine for 48 hrs and illustrating nucleolin degradation.

FIG. 12A depicts schematically seven chimeric RNA-bait molecules to define the nucleolin-binding region of SSAT mRNA. 1-516 is the original chimera and graphics/labels indicate nucleotides omitted in other bait molecules. FIG. 12B is an image of a Western blot analysis. Eluates from HEK293T cell cytoplasmic lysates incubated on columns prepared with the seven bait molecules or a non-specific RNA (control column) were blotted using an anti-nucleolin monoclonal antibody. Lane 1 (C+) is the positive control with HEK293T cell lysate. FIG. 12C is an image of a Western blot detection of recombinant SSAT (rSSAT) (top image) and actin loading controls (bottom image). HEK293T cells were transiently transfected with plasmids to express the complete SSAT ORF (ORF SSAT) or mutant SSAT's using constructs lacking bp's coding for ORF nucleotides 52-117 (ORF SSAT Δ52-117) or 4-45 (ORF SSAT Δ4-45).

FIGS. 13A-13D relate to translation repression and a stem loop in the 5' end of the SSAT coding region. FIG. 13A is a schematic depicting the Mfold calculated RNA secondary structure of the first 140 bp of the SSAT coding sequence (SEQ ID No. 68). The nucleotides between arrows 1 and 2 are deleted in the Δ52-117 construct. The nucleotides between arrows 3 and 4 are deleted in the Δ4-45. FIG. 13B depicts schematics of different stem-loop mutants and a Western blot of SSAT protein expression detected for each in the absence (−) or presence (+) of spermine. FIG. 13C depicts schematics of a hybrid construction ("Loop eGFP") comprising the SSAT 1-75 stem-loop fused in-frame to a sequence encoding eGFP (enhanced green fluorescent protein) as a reporter polypeptide. Below is an image of a Western blot probing eGFP expression. FIG. 13D depicts schematics of mutants of SSAT having the 5' UTR and deletions that impair stem loop formation or ability to bind to nucleolin. Below is an image of a Western blot probing for SSAT translation.

FIG. 14A depicts schematically a series of mutant constructs, above an image of a Western blot to examine the effect of the mutations on SSAT translation. Black dots indicate the location of the starting codons of the uORFs. FIG. 14B depicts schematically a series of mutant constructs and a Western blot of SSAT expression for each in the absence (−) or presence (+) of spermine.

FIGS. 15A and 15B relate to a reporter system to detect pharmacophores. FIG. 15A is a schematic depiction of a chimeric construct comprising a 5' UTR lacking the uORF's and the SSAT coding sequence linked in-frame to the luciferase coding sequence. FIG. 15B is a bar graph illustrating luciferase activity of the chimeric construct in the presence of different small molecules.

FIG. 16A schematically depicts chimeric constructs (top) and an image of a Western blot (bottom) demonstrating translation data obtained using the chimeric constructs. GFP=green fluorescent protein. Loop=sequence from SSAT mRNA containing a stem loop secondary structure. SAT1 400-513=nucleotides 400-513 of the SSAT coding sequence. SAT1 454-513=nucleotides 454-513 of the SSAT coding sequence. FIG. 16B depicts the sequence of nucleotides 397 to 469 of SEQ ID No. 16. Nucleotides 400-453 are boxed.

FIG. 18A is the predicted RNA secondary structure for the wild type SSAT ORF. Nucleotides 151-227 and 393-454 of SEQ ID No. 69 are depicted. FIG. 18N is the predicted secondary structure for mutant 13 RNA, having the single mutation T459C. Nucleotides 274-314, 339-352, and 381-473 of SEQ ID No. 69 are depicted, where nucleotide 459 is changed to C.

FIG. 19A depicts schematically a chimeric construct comprising the 66 nucleotides of the 5'UTR, nucleotides 1-513 encoding SSAT linked in-frame with the coding sequence for luciferase. FIG. 19B is a bar graph depicting luciferase activity for each of the mutant constructs (mutants 1-5 and 7-13) in the absence (left bar) or presence (right bar) of DENSPM. FIG. 19C is a bar graph depicting luciferase activity for mutant 6 in the absence (left bar) or presence (right bar) of DENSPM. Note the difference in scale of the y-axis for FIGS. 19B and 19C.

DEFINITIONS

Figure 9B:
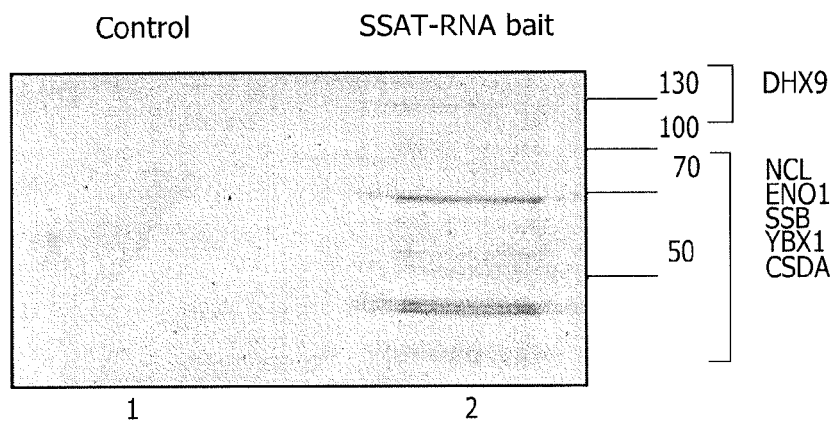

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20%, more preferably ±10%, more preferably ±5%, even more preferably ±1%, and still more preferably ±0.1%.

As used herein, "spermidine/spermine acetyltransferase" ("SSAT") is an enzyme (classified as EC 2.3.1.57). SSAT catalyzes the catalyzes the N(1)-acetylation of spermidine and spermine.

As used herein, a "functional" biological molecule is a biological molecule in a form in which it exhibits a property by which it is characterized. A functional enzyme, for example, is one which exhibits the characteristic catalytic activity by which the enzyme is characterized.

As used herein, a "functional SSAT" refers to any polypeptide that has at least about 5%, at least about 10% SSAT, at least about 20%, preferably at least about 25% and more preferably at least about 50% of the catalytic activity as a SSAT molecule of SEQ ID No. 3, assayed under the same conditions.

As used herein, "translation repression" refers to the condition wherein basal translation of an mRNA is very low or not detectable, relative to basal translation of a gene whose mRNA is translated at a relatively constant level. Examples of such genes are HSP90 and beta-actin.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term "nucleic acid" also specifically includes nucleic acids composed of bases other than the five biologically occurring bases (adenine, guanine, thymine, cytosine and uracil).

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequence.

A "polynucleotide" means a single strand or parallel and anti-parallel strands of a nucleic acid. Thus, a polynucleotide may be either a single-stranded or a double-stranded nucleic acid. The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein, the term "reporter gene" means a gene, the expression of which can be detected using a known method. By way of example, the firefly luciferase gene may be used as a reporter gene in a medium because expression of the luciferase gene can be detected using known methods.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

By "expression cassette" is meant a nucleic acid molecule comprising a coding sequence operably linked to promoter/regulatory sequences necessary for transcription and translation of the coding sequence.

As used herein, as "expression vector" refers to a vector comprising a recombinant polynucleotide comprising an expression cassette. An expression vector comprises sufficient cis-acting elements for expression; other elements for expression can be supplied by the host cell or in an in vitro expression system. Expression vectors useful in the invention include all those known in the art, such as cosmids, plasmids (e.g., naked or contained in liposomes) and viruses that incorporate the recombinant polynucleotide.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

An "mRNA-coding region" of a gene consists of the nucleotide residues of the coding strand of the gene and the nucleotide residues of the non-coding strand of the gene which are homologous with or complementary to, respectively, an mRNA molecule which is produced by transcription of the gene. It is understood that, owing to mRNA processing which occurs in certain instances in eukaryotic cells, the mRNA-coding region of a gene may comprise a single region or a plurality of regions separated from one another in the gene as it occurs in the genome. Where the mRNA-coding region of a gene comprises separate regions in a genome, "mRNA-coding region" refers both individually and collectively to each of these regions.

As used herein "mRNA" refers to an RNA molecule encoding a polypeptide sequence and comprising the regulatory sequences for translation. Such regulatory sequences may include untranslated sequences and include a 5' untranslated region (5' UTR), and a 3' untranslated region ('3-UTR). An mRNA may be modified post-transcriptionally to comprise a 5' cap. In particular, the 5'UTR can contain regulatory elements for effecting translation, such as a Kozak sequence. The 3'UTR can comprise a polyadenylation signal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

By "organ preservation solution" is meant any solution that is adapted to perfuse, to flush or to preserve organs for transplantation, which solution has a protective function in maintaining organs or tissues for transplantation following removal from a donor individual.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.
The term "peptide" typically refers to short polypeptides.

A "hybrid protein" or "fusion protein" is a protein made up of amino acid sequences derived from at least two different sources.

As used herein an "N-terminal fragment of SSAT" refers to a polypeptide fragment comprising at least amino acids 1-10, preferably at least amino acids 1-20, or more preferably at least about amino acid 1-26 of SEQ ID No. 1, 2 or 3.

As used herein a "C-terminal fragment of SSAT refers to a polypeptide fragment comprising at least amino acids 160-171, at least amino acids 150-171, at least amino acids 140-171, or more preferably at least amino acids 136-171 of SEQ ID Nos. 1, 2 or 3.

As used herein, "operably linked" in reference to a gene and a regulatory sequence is meant that a gene and a regulatory sequence are connected in sense or antisense expression in such a way as to permit gene expression when the appropriate molecules (e.g. transcriptional activator proteins) are bound to the regulatory sequence. "Operably linked" with reference to two or more nucleotide coding sequences means that the coding sequences are linked such that the encoded polypeptide fragments are in-frame. "Operably linked" with reference to sequences encoding polypeptides (e.g., hybrid protein) means that the sequences are linked in-frame.

Conventional notation is used herein to portray polypeptide sequences: the left-hand end of a polypeptide sequence is the amino-terminus; the right-hand end of a polypeptide sequence is the carboxyl-terminus.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "cellular proliferative disorder or disease" means a disorder or disease wherein unwanted cell proliferation of one or more subsets of cells in a multicellular organism occurs. In some such disorders and diseases, cells are made by the organism at an atypically accelerated rate. A tumor is an example of a cellular proliferative disorder or disease. A tumor may be benign or malignant.

A disease or disorder is "alleviated" if the severity of a symptom of the disease or disorder, the frequency with which such a symptom is experienced by a patient, or both, are reduced.

It is understood that any and all whole or partial integers between any ranges set forth herein are included herein.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION

As envisioned in the present invention with respect to the disclosed methods and compositions of matter, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

Provided is an isolated nucleic acid encoding a spermidine/spermine acetyltransferase ("SSAT") that is modified such that the mRNA transcript transcribed from the polynucleotide sequence is less translationally repressed and therefore more readily translated and produces more SSAT protein, compared to an mRNA transcript transcribed from a nucleic acid sequence encoding SSAT not comprising the modification. The nucleic acid of the invention therefore has utility in an array of applications, including drug discovery and therapeutic methods. The polynucleotide sequence also may find use in gene therapy applications.

Polynucleotides

The invention includes a nucleic acid sequence encoding a spermidine/spermine acetyltransferase ("SSAT") that has a sequence modification such that the mRNA transcript transcribed from the nucleic acid sequence is less translationally repressed and therefore more readily translated, producing more SSAT protein, compared to an mRNA transcript transcribed from a polynucleotide sequence encoding SSAT not comprising the sequence modification. Specifically, nucleotides coding for the arginine residue at position 142 (Arg142) in the SSAT polypeptide (amino acid numbering with respect to SEQ ID NO. 1) are the nucleotides CGC. As demonstrated herein, an SSAT mRNA transcript having CGC encoding Arg142 is not translationally repressed to the same extent as an SSAT mRNA transcript having the wild-type codon AGA encoding Arg142, in the absence of polyamine or polyamine analog stimulation. In other words, the basal level of translation of an SSAT mRNA transcript having CGC encoding Arg142 according to the invention is significantly higher than the basal level of translation of an SSAT mRNA transcript having AGA encoding Arg142, when assayed under comparable conditions. Furthermore, translation of an SSAT mRNA transcript having CGC encoding Arg142 is stimulated by polyamine or polyamine analog to a much higher degree compared to polyamine- or polyamine-analog-stimulated translation of an SSAT mRNA transcript having AGA encoding Arg142, when assayed under comparable conditions. In addition, the stimulation of translation of an SSAT mRNA transcript having CGC encoding Arg142 is dose dependent. For instance, the stimulation of translation of an SSAT mRNA transcript having CGC encoding Arg142 by $N^1$-$N^{11}$ diethylnorspermine ("DENSPM") exhibits dose dependency over at least two orders of magnitude with respect to the amount of DEN-SPM.

In addition, a sequence in an untranslated region of an SSAT mRNA has been discovered to contribute constitutively to translation repression. Eukaryotic mRNA generally comprises untranslated regions. These regions include a 5' untranslated region (5' UTR), and a 3' untranslated region (3' UTR). A 5' cap is added post-transcriptionally. The 3'UTR generally comprises a polyadenylation signal for post-transcriptional addition of the polyadenylate (polyA) tail. The 5' UTR can contain regulatory elements for controlling translation. The 5' UTR begins at the transcription start site of a gene and ends one nucleotide (nt) before the start codon (usually AUG) of the coding region. As demonstrated herein, sequences in the 5' UTR of human SSAT mRNA have been discovered to constitutively repress translation of SSAT mRNA. Specifically, the 5' UTR of human SSAT contains two open reading frames upstream (uORFs) of the SSAT coding sequence. One uORF begins at position −117 (relative to the start codon) and codes for 4 amino acids. The other begins at −74 (relative to the start codong), overlaps the main ORF, and codes for 29 amino acids. Removing these two uORFs serves to remove their constitutive contribution to translational repression. The uORFs can be removed by mutating the initiation codon such that it is no longer AUG. Alternatively, a portion of the 5' UTR comprising the two uORFs can be deleted from the sequence encoding the SSAT mRNA.

Accordingly, the invention provides an isolated nucleic acid comprising a sequence encoding a spermidine/spermine acetyltransferase, wherein the nucleotides coding for the arginine residue at position 142 (Arg142) in the SSAT are CGC. In one embodiment, the nucleic acid of the invention is RNA, and is preferably mRNA. In this embodiment, the nucleic acid comprises the regulatory sequences in the 5' UTR necessary for translation initiation of the SSAT coding region. Such sequences can include the Kozak sequence. Preferably, the 5' UTR excludes uORF's. In another embodiment, the nucleic acid can be DNA that encodes the mRNA. In this embodiment, the polynucleotide comprises promoter sequence(s) necessary for transcription of the SSAT mRNA. Transcription promoter sequences and mRNA translation initiation sequences are well known in the art.

In an embodiment, the SSAT encoded by the nucleic acid of the invention can be any amino acid sequence that has spermidine/spermine acetyltransferase enzyme activity. There are many SSAT sequences known in the art. The gene encoding human SSAT is known (GenBank Accession No. NM_002970), as are numerous mammalian and non-mammalian homologs. Table 1 provides a non-limiting list of some known SSAT sequences. Other SSAT sequences include chimpanzee (GenBank Accession No. XP_520976.3) which is 100% identical to the human SSAT.

The crystal structure of human SSAT and a mutant SSAT have been solved. The secondary structure and the tertiary structure of human SSAT has been described and mapped to other homologs (Bewley et al., 2006, PNAS 103:2063-2068). Bewley et al. discuss the structure with respect to the function of SSAT. In addition, alignments of SSAT homologs reveal a high degree of homology. In view of this extensive knowledge in the art about the structure-function relationship for SSAT, the skilled artisan has abundant guidance for identifying residues in an SSAT polypeptide sequence that can tolerate mutation without eliminating the enzymatic activity of the SSAT polypeptide.

FIG. 1 depicts the amino acid sequences of the human SSAT protein (SEQ ID No. 3) and twelve vertebrate homologs (SEQ ID NOs. 4-14). A first consensus sequence (SEQ ID NO. 1) is also depicted. The consensus sequence consists of the invariant amino acid residues shared when the amino acid sequences for these twelve vertebrate homologs are aligned and compared. The percent identity to the consensus sequence is summarized in Table 1.

TABLE 1

| Organism | SwissProt Accession No. | SEQ ID No. | % identity to SEQ ID NO. 1 |
|---|---|---|---|
| Homo sapiens (Human) | P21673 | 3 | 68 |
| Sus scrofa (Pig) | Q28999 | 4 | 68 |
| Bos Taurus (Bovine) | Q3T0Q0 | 5 | 68 |
| Capra hircus (Goat) | A9YUB6 | 6 | 68 |
| Mus musculus (Mouse) | P48026 | 7 | 68 |
| Rattus norvegicus (Norway rat) | Q6P9U6 | 8 | 68 |
| Cricetulus griseus (Chinese hamster) | Q9JHW6 | 9 | 68 |
| Gallus gallus (Chicken) | Q8AXL1 | 10 | 70 |
| Xenopus laevis (African clawed frog) | Q68F31 | 11 | 71 |
| Pelophylax ridibundus (Marsh frog) | Q804J9 | 12 | 71 |
| Rana catesbeiana (American bullfrog) | C1C4T9 | 13 | 68 |
| Danio rerio (Zebrafish) | Q4V8U3 | 14 | 71 |

In view of the many species of SSAT homologs and the structure-function information in the art, the skilled artisan will recognize that conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Conservative substitutions may also be made based on types of amino acids: aliphatic (valine, isoleucine, leucine, and alanine); charged (aspartic acid, glutamic acid, lysine, arginine, and histidine); aromatic residues (phenylalanine, tyrosine and tryptophan); and sulfur-containing (methionine and cysteine).

FIG. 2 summarizes the general type of amino acid found at the variable residues ("X") of SEQ ID No. 1, and exemplary amino acids for each X residue.

Polypeptide sequences having at least about 68% identity, at least about 70% identity, or at least about 71% identity to SEQ ID No. 1 are reasonably expected to possess SSAT enzymatic activity (i.e., functional SSAT). Polypeptide sequences having at least about 73% identity, at least about 75%, at least about 78%, at least about 80%, at least about 82%, at least about 85%, at least about 88%, or more are also reasonably expected to possess SSAT activity. In particular, polypeptide sequences that are at least about 90%, at least 93%, at least 95%, at least 96%, at least 97%, at least 98%, or at least 99% identical to the specified residues in SEQ ID No. 1 are reasonably expect to possess SSAT enzymatic activity.

A second consensus amino acid sequence (SEQ ID NO. 2) is depicted in FIG. 3. The second consensus sequence consists of the invariant amino acid residues shared when the amino acid sequences for the mammalian homologs (SEQ ID Nos. 3-9) are aligned and compared. The percent identity of the mammalian homologs to the consensus sequence is summarized in Table 2. FIG. 4 summarizes the general type of amino acid found at the variable residues ("X") of SEQ ID No. 2, and exemplary amino acids for each X residue. Polypeptide sequences having at least about 71% identity, at least about 73% identity, or at least about 75% identity to SEQ ID No. 2 are reasonably expected to possess SSAT enzymatic activity (i.e., functional SSAT). Polypeptide sequences having at least about at least about 78%, at least about 80%, at least about 82%, at least about 85%, at least about 88%, at least about 90%, or more are also reasonably expected to possess SSAT activity. In particular, polypeptides having at least about 94% identity, or at least about 95% identity to SEQ ID No. 2 are reasonably expected to possess SSAT enzymatic activity.

TABLE 2

| Organism | SwissProt Accession No. | SEQ ID No. | % identity to SEQ ID NO. 2 |
| --- | --- | --- | --- |
| Homo sapiens (Human) | P21673 | 3 | 95 |
| Sus scrofa (Pig) | Q28999 | 4 | 95 |
| Bos Taurus (Bovine) | Q3T0Q0 | 5 | 94 |
| Capra hircus (Goat) | A9YUB6 | 6 | 94 |
| Mus musculus (Mouse) | P48026 | 7 | 95 |
| Rattus norvegicus (Norway rat) | Q6P9U6 | 8 | 95 |
| Cricetulus griseus (Chinese hamster) | Q9JHW6 | 9 | 95 |

The percent identity of each of the non-human homologs relative to the human homolog is summarized in Table 3.

TABLE 3

| Organism | SwissProt Accession No. | SEQ ID No. | % identity to SEQ ID NO. 3 |
| --- | --- | --- | --- |
| Homo sapiens (human) | P21673 | 3 | 100 |
| Sus scrofa (pig) | Q28999 | 4 | 98 |
| Bos Taurus (Bovine) | Q3T0Q0 | 5 | 97 |
| Capra hircus (Goat) | A9YUB6 | 6 | 96 |
| Mus musculus (mouse) | P48026 | 7 | 96 |
| Rattus norvegicus (Norway rat) | Q6P9U6 | 8 | 96 |
| Cricetulus griseus (Chinese hamster) | Q9JHW6 | 9 | 96 |
| Gallus gallus (Chicken) | Q8AXL1 | 10 | 87 |
| Xenopus laevis (African clawed frog) | Q68F31 | 11 | 82 |
| Pelophylax ridibundus (Marsh frog) | Q804J9 | 12 | 82 |
| Rana catesbeiana (American bullfrog) | C1C4T9 | 13 | 82 |
| Danio rerio (Zebrafish) | Q4V8U3 | 14 | 78 |

Polypeptide sequences having at least about 82% identity, at least about 87%, at least about 95%, at least about 96%, at least about 97%, or at least about 98% identity to SEQ ID No. 3 are reasonably expected to possess SSAT enzymatic activity.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator blast(dot)ncbi (dot)nlm(dot)nih(dot)gov/blast(dot)cgi. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See blast(dot)ncbi(dot)nlm(dot)nih(dot)gov/blast(dot)cgi. In calculating percent identity, exact matches are typically counted.

Accordingly, in an embodiment, the nucleic acid of the invention comprises a nucleotide sequence that encodes the polypeptide of SEQ ID No. 1, wherein the nucleotide sequence encoding Arg142 of SEQ ID No. 1 is CGC. In another embodiment, the nucleic acid of the invention comprises a nucleotide sequence that encodes the polypeptide of SEQ ID No. 2, wherein the nucleotide sequence encoding Arg142 of SEQ ID No. 1 is CGC. In yet another embodiment, the polypeptide of SEQ ID No. 2 is selected from: SEQ ID No. 3, SEQ ID No. 4, SEQ ID No. 5, SEQ ID No. 5, SEQ ID No. 6, SEQ ID No. 7, SEQ ID No. 8, and SEQ ID No. 9. In a preferred embodiment, the polypeptide of SEQ ID No. 1 or 2 is SEQ ID No. 3.

An mRNA nucleotide sequence for wild-type human SSAT (SEQ ID No. 15) is shown in FIG. 5 (as cDNA). The nucleotide sequence of the coding sequence (SEQ ID No. 16) and the corresponding amino acid sequence (SEQ ID No. 17) of human SSAT are shown in FIG. 6. The 5' UTR sequence of a human SSAT mRNA is depicted in FIG. 7 (SEQ ID No. 18).

As discussed elsewhere herein, a segment in an untranslated region of an SSAT mRNA has been discovered to contribute constitutively to translation repression of SSAT mRNA. Specifically, the 5' UTR of human SSAT contains two open reading frames upstream (uORFs) of the SSAT coding sequence. One uORF begins at −117 and codes for 4 amino acids. The other begins at −74, overlaps the main coding region, and codes for 29 amino acids. Removing these two uORFs serves to remove their constitutive contribution to translational repression. The uORFs can be removed by mutating the initiation codon such that it is no longer AUG. Alternatively, a segment of the 5' UTR comprising the two uORFs can be deleted from the nucleotide sequence encoding the SSAT mRNA. Accordingly, in an embodiment, a nucleic acid comprising a first sequence that encodes the polypeptide of SEQ ID No. 1, wherein the sequence encoding Arg142 of SEQ ID No. 1 is CGC may further comprise a 5' untranslated region (5' UTR) sequence of a mRNA encoding a spermidine/spermine acetyltransferase operably linked to the first sequence. The 5' UTR comprises translation initiation sequences, such as a Kozak sequence, operably linked to the coding region for SSAT but does not comprise an open reading frame upstream from the initiation codon of the SSAT coding region. In addition, the 5' UTR preferably comprises at least about 50 nucleotides in order to overcome translation repression arising from a stem-loop (nucleotides 2-76 of SEQ ID No. 17) at the 5' end of the coding region of the mRNA.

Exemplary polynucleotides of the invention are shown in FIGS. 8A, 8B and 8C. The polynucleotide in FIG. 8A is a coding sequence for human SSAT starting with the initiation codon, and lacking the termination codon. The codon encoding Arg142 is CGC. The polynucleotide in FIG. 8B contains the same nucleotide sequence as FIG. 8A, but further comprising 5' UTR nucleotides –66 to –1 of the human SSAT mRNA (see FIG. 7). The polynucleotide as FIG. 8C contains the same sequence as in FIG. 8A, but further comprising 5' UTR nucleotides –155 to –1 of the human SSAT mRNA, wherein the uORF initiation codons beginning at –117 and at –74 are mutated to eliminate translation initiation (see FIG. 7).

Table 4 lists accession numbers for exemplary mRNAs of various SSAT homologs. The nucleotide sequences are incorporated herein in their entirety by reference. The skilled artisan is capable of identifying in each of these sequences the pertinent sub-sequences for use in the present invention, including the coding sequence, the codon for Arg142, the transcription start site, the translation initiation sequence, the initiation codon of the coding sequence and the termination codon of the coding sequence. In view of the knowledge in the art, the skilled artisan is also readily able to identify uORF's in such sequences, and remove them by deletion or mutation (Ivanov et al., 2010, NAR 38:353-359).

TABLE 4

| Organism | SwissProt Accession No. | GenBank Accession No. | SEQ ID NO. |
|---|---|---|---|
| Homo sapiens (human) | P21673 | NM_002970 | 73 |
|  |  | BC002503 | 15 |
| Sus scrofa (pig) | Q28999 | U57333 | 74 |
| Bos Taurus (Bovine) | Q3T0Q0 | BC102304 | 75 |
| Capra hircus (Goat) | A9YUB6 | EU295698 | 76 |
| Mus musculus (mouse) | P48026 | AK002531 | 77 |
| Rattus norvegicus (Norway rat) | Q6P9U6 | BC060588 | 78 |
| Cricetulus griseus (Chinese hamster) | Q9JHW6 | AF281149 | 79 |
| Gallus gallus (Chicken) | Q8AXL1 | AF402003 | 80 |
| Xenopus laevis (African clawed frog) | Q68F31 | BC080014 | 81 |
| Pelophylax ridibundus (Marsh frog) | Q804J9 | AY157829 | 82 |
| Rana catesbeiana (American bullfrog) | C1C4T9 | BT081868 | 83 |
| Danio rerio (Zebrafish) | Q4V8U3 | BC097197 | 84 |

Also included in the invention are polynucleotides encoding hybrid proteins comprising an SSAT polypeptide or fragment thereof operatively fused directly or indirectly via peptide linker, to a second polypeptide sequence. Linker sequences are well known in the art. "SSAT fragment" in the practice of the invention refers to a fragment comprising at least amino acids 1-26 of SEQ ID No. 1, 2 or 3, or to a fragment comprising at least amino acids 134-171 of SEQ ID No. 1, 2 or 3. The SSAT polypeptide of the hybrid may comprise any of the previously described SSAT polypeptides. Hybrid polypeptides may comprise an N-terminal fragment of SSAT, a C-terminal fragment of SSAT, or both. In a preferred embodiment, a hybrid protein comprises an SSAT polypeptide or fragment thereof operatively fused to a reporter polypeptide, wherein the reporter polypeptide is fused to the C-terminal of the SSAT polypeptide, directly or indirectly. Exemplary reporter polypeptides include luciferase (LUC), green fluorescent protein (GFP), and GFP derivatives.

Hybrid proteins comprising an SSAT polypeptide or fragment thereof may be linked to other types of polypeptides, in addition to a reporter polypeptide, or in lieu of a reporter polypeptide. These additional polypeptides may be any amino acid sequence useful for the purification, identification and/or therapeutic or prophylactic application of the peptide. Non-limiting examples of such additional segments include LacZ, FLAG-tag, Myc, His$_6$ (SEQ ID NO: 72) and the like. The SSAT polypeptide portion may be fused directly to the second peptide or may be separated by a linker sequence.

It is not intended that the present invention be limited by the nature of the nucleic acid employed. The target nucleic acid may be native, synthesized nucleic acid, or a combination thereof. The nucleic acid may be partially or wholly from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as pGEM® T vector or SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH$_2$—S—CH$_2$), dimethylene-sulfoxide (—CH$_2$—SO—CH$_2$), dimethylene-sulfone (—CH$_2$—SO$_2$—CH$_2$), 2'-O-alkyl, and 2'-deoxy-2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic acids can be purified by reverse phase or ion exchange HPLC, size exclusion chromatography, or gel electrophoresis. Of course, the skilled artisan will recognize that the method of purification will depend in part on the size of the DNA to be purified.

The term "nucleic acid" also specifically includes nucleic acids composed of bases other than the five biologically occurring bases (adenine, guanine, thymine, cytosine and uracil).

Techniques for introducing changes in nucleotide sequences that are designed to alter the functional properties of the encoded proteins or polypeptides are well known in the art. Such modifications include the deletion, insertion, or substitution of bases, and thus, changes in the amino acid sequence. Changes may be made to increase the activity of a protein, to increase its biological stability or half-life, to change its glycosylation pattern, and the like. All such modifications to the nucleotide sequences encoding such proteins are encompassed by this invention, provided the codon for Arg142 is CGC.

In some applications, it is contemplated that the SSAT encoded does not need be functional. In such applications, the coding sequence for SSAT may comprise mutations in the amino acid sequence that reduce activity. Non-limiting examples of residues for mutation include those involved in binding acetyl Co-A, those involved in binding polyamines and/or those involved in the catalytic active site (see, for instance, Supporting FIG. 5, Bewley et al., 2006, PNAS 103:2063-2068; incorporated herein by reference). Such mutations should be selected such that the Mfold predicted secondary structure of the resulting mRNA encoding the mutated SSAT is substantially the same as the Mfold predicted secondary structure for SEQ ID No. 19. By "substantially the same" is here meant that at least the stem-loop predicted for nucleotides 2-76 (of SEQ ID No. 19) and the secondary structure predicted for nucleotides 400-513 (of SEQ ID No. 19), wherein the codon for Arg142 is CGC, are predicted to be present in the mutant mRNA. In another embodiment, a mutant polynucleotide may comprise an internal deletion of the wild-type SSAT sequence encoding the SSAT polypeptide. For instance, a segment comprising the stem-loop predicted for nucleotides 2-76 of SEQ ID No. 19 may be operably fused to a segment comprising nucleotides 400-513, wherein the codon for Arg142 is CGC (e.g., nucleotides 400-513 of SEQ ID No.19). Thus, in an embodiment, the nucleic acid of the invention comprises a sequence encoding amino acids 1-26 of SEQ ID No. 1, 2 or 3 operably linked to a sequence encoding amino acids 134-171 of SEQ ID Nos. 1, 2 or 3, wherein the codon for Arg142 (numbering as for SEQ ID No. 1) is CGC. An exemplary embodiment is a nucleic acid comprising nucleotides 1-78 of SEQ ID No. 19 operably linked to nucleotides 400-513 of SEQ ID No. 19. Another exemplary embodiment is a nucleic acid comprising nucleotides 1-222 of SEQ ID No. 19 operably linked to nucleotides 400-513 of SEQ ID No. 19.

The isolated nucleic acid of the invention can be used in any application that would benefit from increased translation of an SSAT mRNA. For instance, the isolated nucleic acid may be used to transfect a cell, transiently or stably, to produce an increased amount of SSAT protein in an expression system. This application may be useful for purification purposes. Other applications of the isolated nucleic acid are discussed in more detail below.

Assay for Candidate Agents

The invention also provides a method of drug discovery using the nucleic acid of the invention. Drug discovery includes screening candidate agents to identify those agents that de-repress translation of the SSAT mRNA transcript. Such a translation de-repression agent may possess therapeutic activity as an anti-proliferative agent and/or may serve as a lead compound in developing an anti-proliferative agent. The basal translation of the SSAT mRNA of the invention is substantially increased compared to translation of wild-type SSAT mRNA. The higher level of basal translation provides an improved dynamic range thus enabling the ability to detect a decrease in basal translation. Accordingly, drug discovery also includes screening candidate agents to identify those agents that repress translation of the SSAT transcript. Agents that repress translation may possess therapeutic activity in disorders or diseases characterized at least in part by increased SSAT activity. Exemplary diseases having such increased SSAT activity include ischemia-reperfusion injury, stroke and myocardial infarction. It is believed that the increased activity of SSAT in these diseases is partially responsible for the damage in the tissues upon an ischemia episode.

In an embodiment, the method comprises assessing translation of the SSAT mRNA of the invention in the presence or absence of a test compound. When the method is practiced to identify an agent that de-represses translation of the SSAT mRNA transcript, a higher level of translation in the presence of the test compound compared with the level of translation in the absence of the test compound, is an indication that the test compound can de-repress translation repression. The degree of translation in the presence of the test compound can also be compared to translation in the presence of a known de-repressor, such as DENSPM. When the method is practiced to identify an agent that represses translation of the SSAT mRNA transcript, a reduced level of translation in the presence of the test compound compared with the level of translation in the absence of the test compound, is an indication that the test compound can repress translation.

In an embodiment, the method comprises assessing translation of an RNA in the absence of a candidate agent to obtain a reference level of translation, wherein the RNA is a nucleic acid comprising a first sequence encoding the polypeptide of SEQ ID No. 1, wherein the nucleotide sequence encoding Arg142 of SEQ ID No. 1 is CGC. The RNA can be an isolated RNA. The RNA further comprises the regulatory sequences, such as the 5'UTR and 3'UTR, needed for translation. Such regulatory sequences are well known in the art. See, for instance, Pesole et al., 2000, Briefings in Bioinformatics, 1:236-249. Preferably, the 5'UTR is from a mammalian SSAT mRNA, and more preferably, is from human SSAT.

In an embodiment, the first sequence of the RNA encodes SEQ ID No. 2. In an embodiment, the RNA comprises SEQ ID No. 20 or SEQ ID No. 21.

The SSAT RNA used in the method preferably encodes a chimeric polypeptide comprising SSAT and a reporter polypeptide. The level of translation is assessed by measuring the reporter polypeptide signal, such as detection of light or fluorescence. For instance, where the reporter polypeptide is luciferase, luminescence can be measured using a luminometer or any suitable radiant energy-measuring device.

In embodiments using a reporter polypeptide, it is not necessary that the SSAT polypeptide portion of the chimeric polypeptide be functional. For instance, the SSAT polypeptide coding sequence could comprise an internal deletion, as discussed elsewhere herein. Alternatively, the coding sequence could comprise mutations that disrupt acetyl Co-A binding, provided the secondary structure for the mRNA is predicted to be substantially the same as that predicted for SEQ ID No. 19. Secondary structure prediction for RNA is conventional in the art. An exemplary method is Mfold (Zuker, 2003, NAR 31(13):3406-3415).

Any method known in the art can be used to assess translation. In a preferred embodiment, translation is assessed using mammalian cells transfected with an expression vector comprising a nucleic acid of the invention. The transfection may be transient or the cells may stably transformed with the expression vector. A cell-based assay such as described in Butcher et al., 2007, J Biol Chem. 282:2853-28539 may be used. Alternatively, an in vitro translation assay may be used.

In the context of an expression vector, the vector can be readily introduced into a host cell, e.g., mammalian, bacterial, yeast or insect cell, by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, photoporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, a preferred delivery vehicle is a liposome. The above-mentioned delivery systems and protocols therefore can be found in "Gene Targeting Protocols, 2ed.", Kmiec ed., Humana Press, Totowa, N.J., pp 1-35 (2002) and "Gene Transfer and Expression Protocols, Vol. 7, (Methods in Molecular Biology)," Murray ed., Humana Press, Totowa, N.J., pp 81-89 (1991).

The methods can be practiced with any test compounds as candidate agents. Test compounds useful in practicing the inventive method may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145).

Examples of methods for the synthesis of molecular libraries may be found in the art, for example, in: DeWitt et al., 1993, Proc. Natl. Acad. Sci. USA 90:6909-6913; Erb et al., 1994, Proc. Natl. Acad. Sci. USA 91:11422-11426; Zuckermann et al., 1994, J. Med. Chem. 37:2678-2685; Cho et al., 1992, Science 261:1303-1305; Carell et al., 1994, Angew. Chem. Int. Ed. Engl. 33:2059-2061; Carell et al., 1994, Angew. Chem. Int. Ed. Engl. 33:2061-2064; and Gallop et al., 1994, J. Med. Chem. 37:1233-1251.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223, 409), plasmids (Cull et al., 1992, Proc. Natl. Acad. Sci. USA 89:1865-1869), or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

Commercially available libraries that may be screened include, but are not limited to, the TimTec Natural Product Library (NPL), NPL-640, and TimTec NDL-3000 library. Libraries comprising compounds modeled on polyamines (i.e., polyamine analogs) may also be screened.

The method may be practiced iteratively using different concentrations of a test candidate and/or different testing conditions, such as duration of reaction time. Test candidates that are identified by the method can be further tested by conventional methods in the art to verify specificity, dose dependency, efficacy in vivo, and the like. Test candidates may serve as lead compounds for developing additional test candidates.

Therapeutic Applications

The invention also provides a method of increasing the amount of SSAT polypeptide in a cell. The cell may be in vivo, in vitro or ex vivo. The increase in SSAT is expected to increase SSAT activity, which has been demonstrated previously to have antiproliferative consequences. Accordingly, the method may find use in alleviating a cellular proliferative disease or disorder. In an embodiment, the method of alleviating a cellular proliferative disease or disorder comprises introducing a nucleic acid of the invention into a cell of the cellular proliferative disease or disorder in a subject diagnosed with a cellular proliferative disease or disorder. A "subject" of diagnosis or treatment is a mammal, including a human. Non-human animals subject to diagnosis or treatment include, for example, primates, mice, rats, cattle, sheep, goats, horses, canines, felines and the like.

In an embodiment, the method comprises administering a vector comprising an expression cassette having the nucleic acid of the invention to a cell, such as a cell of a cellular proliferative disease or disorder. Expression vectors and methods for the introduction of exogenous DNA into cells with concomitant expression of the exogenous DNA in the cells are described, for example, in Sambrook et al. (2001, Molecular Cloning: A Laboratory Manual, Cold Spring Harbor Laboratory Press, Cold Spring Harbor, N.Y.), and in Ausubel et al. (eds, 1997, Current Protocols in Molecular Biology, John Wiley & Sons, New York, N.Y.). Any expression vector compatible with the expression of SSAT in a mammalian cell is suitable for use in the instant invention, and can be selected from a plasmid DNA, a viral vector, or a mammalian vector. The expression vector, or a vector that is co-introduced with the expression vector, can further comprise a marker gene. Marker genes are useful, for instance, to monitor transfection efficiencies. Marker genes include: genes for selectable markers, including but not limited to, G418, hygromycin, and methotrexate, and genes for detectable markers, including, but not limited to, luciferase and GFP. The expression vector can further comprise an integration signal sequence, which facilitates integration of the isolated polynucleotide into the genome of a mammalian cell.

Given the increased basal translation of the SSAT mRNA of the invention, it is envisioned that the resulting increase in SSAT activity will result in improved growth inhibition and optionally polyamine depletion, compared to SSAT mRNA not having Arg142 encoded by CGC.

Cellular proliferative disorders and diseases are well known in the art and include but are not limited to cancer, malignant and benign tumors, blood vessel proliferative disorders, autoimmune disorders, and fibrotic disorders.

Tumors include but are not limited to: ovarian cancer; cervical cancer; breast cancer; prostate cancer; testicular cancer, lung cancer, renal cancer; colorectal cancer; skin cancer; brain cancer; leukemia, including acute myeloid leukemia, chronic myeloid leukemia, acute lymphoid leukemia, and chronic lymphoid leukemia.

More particularly, cancers that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders or diseases.

The methods and compositions of the invention are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate.

The method of the present invention is preferably practiced with any tumor cell for which there are tissue or tumor specific gene promoters. The invention is intended to cover all of these possibilities. The ability to achieve tumor or organ selectivity with tissue-specific gene promoters can be advantageously used to target the desired site. Different tumors can be targeted by using tissue specific promoters. For example, a tissue-specific promoter such as tyrosinase is appropriate for targeting melanoma while prostate-specific antigen (PSA), probasin, prostate-specific membrane antigen (PSMA) or various other prostate-specific proteins are suitable for targeting prostate carcinoma. For tumors of the nervous system, promoters that can be used include, but are not limited to, the glial fibrillary acidic protein (GFAP) promoter, the neuron specific enolase (NSE) promoter, neurotransmitter promoters (e.g., tyrosine hydroxylase, choline acetyltransferase), and promoters for neurotrophic factors (e.g., nerve growth factor, NT-3, brain derived growth factor and the like). It is preferable to use both the core promoter and enhancer regions in order to obtain maximal gene expression.

In a preferred embodiment, the SSAT gene therapy is used to alleviate prostate carcinoma. In addition to the clinical importance of this pathological condition, several well characterized gene promoter/enhancer systems with high selectivity towards prostate tissue and prostate carcinoma are available (Brookes et al., 1998, The Prostate 35:18-26). Further, organ and primary tumors are accessible for brachytherapy via transperineal delivery (Blasko et al., 1994, Semin. Rad. Oncol. 3:240-249). In addition to the above rationale, the prospects for selectivity towards prostate carcinoma by polyamine-directed strategies, is enhanced by the fact that the gland represents the richest source of polyamine biosynthesis in the body and is the only tissue to synthesize polyamines for export (into semen).

Another example of a tumor that can be targeted using the method of the present invention is melanoma. The tissue/tumor specific promoter/enhancer can be tyrosinase, a key enzyme in the synthesis of melanin pigment. An advantage of using the method of the present invention for this disease is the ease of direct intratumoral injection of the gene therapy system. Other tumors that can be targeted using the method of the invention include colorectal cancer, ovarian cancer, and lung carcinoma such as small cell, A viral vector can be used to introduce cDNA comprising the nucleic acid of the invention into a tumor. The SSAT cDNA is inserted into the viral genome. Regulatory elements to direct the expression of the gene product can be included with the SSAT cDNA. The regulatory elements may include tissue-specific promoters as described above. Viral vectors which can be used for the purposes of introducing the SSAT cDNA into tumor cells include, but are not limited to, adenoviruses, adeno-associated viruses, herpes viruses, and replication-defective retroviruses. Viral systems may be utilized which are only capable of replicating in tumor cells which are defective in critical proteins required for regulation of cell cycle, such as p53 and others (Bischoff et al., 1996, Science 274:373-376). In addition to viral vectors, other transfer methods based on mechanisms used by mammalian cells for cellular uptake of macromolecules can be utilized. Such methods include liposomal derived systems, poly-lysine conjugates, and the like.

A particular advantage of the contemplated gene therapy is that the nucleic acid of the invention has a significantly higher level of basal translation than the corresponding wild-type nucleic acid. As such, it may not be necessary to administer an SSAT de-repressor such as DENSPM. However, the basal level of translation of the nucleic acid of the invention can be potently amplified by the administration of as SSAT translation de-repressor such as DENSPM.

In another embodiment, a conditionally regulated system can be used to alter the expression of SSAT encoded by the nucleic acid of the invention. An example is the tetracycline dependent gene expression system (Clonetech). This provides regulated and reversible control of gene expression. Other conditionally-regulated systems known in the art of gene therapy may also be used.

The present invention provides compounds and methods for preventing or attenuating ischemia-reperfusion injury (IRI) in mammals, which occurs when the blood supply to an organ or tissue is interrupted and then restored. The organs are preserved on ice for up to several hours before being transplanted. During this period the organ is anoxic. An SSAT translation inhibitor is used according to the present invention is used to treat organs and tissues for transplantation. A composition comprising an SSAT inhibitor is used to prevent or attenuate IRI and protect organs in organs transplanted from cadaver and live donors. The composition may be utilized, for example, for preventing or attenuating cold ischemia-warm reperfusion injury in mammals.

The present invention is thus directed to methods for preserving organs and tissues comprising contacting the organ or tissue with a composition comprising an SSAT translation inhibitor. Typically, the composition will comprise an organ preservative solution, such as those described hereinafter. The invention also relates to reducing, inhibiting or preventing reperfusion injury or damage in an organ or tissue that has been removed from its host comprising contacting the organ or tissue with an SSAT translation inhibitor. Preservative solutions comprising an SSAT translation inhibitor can be used to preserve and/or protect organ tissue, or whole organs, when the organs or tissue are brought into contact with the solution.

According to typical procedures, organs to be used for transplantation are recovered from cadaver donors and perfused with appropriate organ preservation solution. Such solutions comprise, for example, the Wisconsin-Cold Storage Solution (UW-CSS) (Belzer et al., *Transplantation* 1988; 45:673; and (Belzer, et al., U.S. Pat. No. 4,798,824).

In one embodiment, to protect organ transplants, an SSAT translation inhibitor is added to the preservation fluid used for in situ organ perfusion and cooling in the donor, or for cold storage or perfusion after the organ is harvested. The organ or tissue transplants can be perfused or flushed with a solution containing an SSAT translation inhibitor. In this manner, IRI is prevented and functional recovery of the organ after transplantation is promoted.

The SSAT translation inhibitor may be added to the perfusion, preservation or flush solution in a concentration effective to inhibit SSAT translation. A range of concentration of inhibitor in the solution can include, for example, from about 0.01 to about 1 mg/L, more typically from about 0.1 to about 1 mg/L. The expression "organ preservation solution" is understood to mean any such solution that is utilized to perfuse, to flush or to preserve organs for transplantation following removal from a donor individual.

Organs or tissue may be perfused with a solution containing, in addition to the SSAT translation inhibitor, typical components such as electrolytes and cell-protecting agents that are utilized in typical organ preservation solutions.

As described in US Pat. App. Pub. 20070054855, organ preservation solutions typically contain electrolytes (such as $Na^+$, $K^+$, $Mg^{++}$, $Cl^-$; $SO_4^{2-}$; $HPO_{42-}$; $Ca^{2+}$ and $HCO^{3-}$;) and may contain various other agents protecting the cells during cold storage. The University of Wisconsin Belzer solution, for example, comprises 50 g/L hydroxyethyl starch, 35.83 g/L lactobionic acid, 3.4 g/L potassium phosphate monobasic, 1.23 g/L magnesium sulfate heptahydrate, 17.83 g/L raffinose pentahydrate, 1.34 g/L adenosine, 0.136 g/L allopurinol, 0.922 g/L glutathionine, 5.61 g/L potassium hydroxide and sodium hydroxide for adjustment of pH to pH 7.4. Belzer UW solutions are sold under the trademark VIASPAN® (Du Pont Chemical Company), and described in U.S. Pat. Nos. 4,798,824, 4,873,230, 4,879,283.

Another example of an organ preservation solution is the Euro-Collins solution (Fresenius AG of Germany), which contains 2.05 g/L mono-potassium phosphate, 7.4 g/L dipotassium phosphate, 1.12 g/L potassium chloride, 0.84 g/L sodium bicarbonate and 35 g/L glucose. In use, these intracellular type preservation solutions are rinsed away from the donor organ before completion of transplantation into the recipient by using a physiological infusion solution, such as Ringer's solution. SSAT translation inhibitor can be also added to a rinse solution.

Other organ preservations solutions that must be flushed away include extracellular type preservation solutions such as PEFADEX (Vitrolife, Sweden), which contains 50 g/L dextran, 8 g/L sodium chloride, 400 mg/L potassium chloride, 98 mg/L magnesium sulfate, 46 mg/L disodium phosphate, 63 mg/L potassium phosphate and 910 mg/L glucose include. The SSAT translation inhibitor can be added to such preservation solutions.

Other organ preservation solutions include the Stanford University solution (see, e.g., Swanson, et al., *Journal of Heart Transplantation*, (1988), 7(6):456-467 and a modified Collins solution (see, e.g., Maurer, et al., *Transplantation Proceedings*, (1990), 22(2):548-550).

Other solutions for organ preservation include those described by Berdyaev et al., U.S. Pat. No. 5,432,053; Belzer et al., U.S. Pat. Nos. 4,798,824, 4,879,283, and 4,873,230; Taylor, U.S. Pat. No. 5,405,742; Dohi et al., U.S. Pat. No. 5,565,317; Stern et al., U.S. Pat. Nos. 5,370,989 and 5,552,267, the contents of which are incorporated herein by reference in their entirety.

Further representative organ preservation solutions are described in Cicardie et al. U.S. Pat. No. 7,718,617, particular Tables 2-6 thereof.

One or more SSAT translation inhibitors may be added to any of the aforementioned commercial available organ preservation or rinsing solution for organs or tissues used for transplant. The preservation solutions described above are intended to be exemplary and not intended to be limiting. Furthermore, a suitable preservation or rinsing solution may comprise a variant of commercially available solution such as UW-CSS, Euro-Collins or PEFADEX where concentrations of components are varied from the concentrations recited above.

The solutions of the invention can be used to maintain viability of the organ or tissue during storage, transplantation or other surgery. The invention includes a method of storing tissue or organs comprising contacting said tissue, organ or part thereof, with the solution of the invention, such that the in vivo and/or in vitro viability is prolonged. The solutions permit maintenance of viability of heart or lung tissue for up to 24 hours or more. Use of the solutions of the invention results in improved organ viability.

In another embodiment, one or more SSAT translation inhibitors are added to flush-storage solutions used to flush organs prior to transplantation to prepare the graft for transplantation. Flush-storage solutions comprise sterile aqueous solutions with a pH, osmolarity and ionic composition compatible with the organ and take into consideration the metabolic activity and adenine nucleotide content of the organ during storage. Representative flush-storage solutions include the "Euro-Collins" solution described above, VIAS- PAN® (Du Pont Chemical Company) and SOLTRAN kidney perfusion solution (Baxter Healthcare Ltd, UK.). The SOLTRAN solution contains, per 1 liter of solution: Potassium citrate 8.6 g; sodium citrate 8.2 g; mannitol 33.8 g; and magnesium sulphate 10.0 g. The solution has a pH of 7.1 and an osmolarity of 486 mOsm/L.

Another suitable flush-storage solution is saline solution, preferable a solution close to isotonic (0.145M).

It may be appreciated that some solutions that are flush-storage solutions may also comprise organ preservation solutions.

Alternatively or in addition, the SSAT translation inhibitors is administered to the transplant recipient just prior to, or concomitant with, transplantation. The inhibitor also can be administered directly to the tissue at risk, as by injection to the tissue, or it may be provided systemically, either by oral or parenteral administration.

The organs and tissues that may be contacted with one or more SSAT translation inhibitors include, by way of example and not limitation whole organs such as heart, liver, kidney, lung, and pancreas, or parts or tissues thereof. Further included are tissues such as intestinal tracts, intestinal tissues, endothelial tissue, bone marrow, eyeball, cornea, bone, skin, vascular tissue (e.g. an aorta graft), and heart valve.

EXAMPLES

The products, compositions, and methods are further described in detail by reference to the following experimental example. The example is provided for purposes of illustration only, and is not intended to be limiting unless otherwise specified. Thus, the products, compositions, and methods should in no way be construed as being limited to the following example, but rather, should be construed to encompass any and all variations which become evident as a result of the teaching provided herein.

Materials and methods used in the examples are described.

Gene Templates Used for PCR Reactions:

The plasmid containing the human SSAT cDNA was obtained from Open Biosystems (Clone ID: 3051095; Huntsville, Ala.). The sequence of containing the complete CDS of the human SSAT cDNA in the clone is: CTGGT-GTTTATCCGTCACTCGCCGAGGTTCCTTGGGT-CATGGTGCCAGCCTGACTGA GAAGAGGACGCTC-CCGGGAGACGAATGAGGAACCACCTCCTCCTACT-GTTCAAGTA CAGGGGCCTGGTCCG-CAAAGGGAAGAAAAGCAAAAGACGAAAATG-GCTAAATTCG TGATCCGCCCAGCCACTGCCGC-CGACTGCAGTGACATACTGCGGCTGATCAAGGAG CTGGCTAAATATGAATACATGGAAGAACAAG-TAATCTTAACTGAAAAAGATCTGCT AGAAGATG-GTTTTGGAGAGCACCCCTTTTACCACTGCCTGGTT-GCAGAAGTGCCGAA AGAGCACTGGACTCCGGAAGGACACAGCATTGT-TGGTTTTGCCATGTACTATTTTAC CTATGACCCGTG-GATTGGCAAGTTATTGTATCTTGAGGACTTCTTCGT-GATGAGTGA TTATAGAGGCTTTGGCATAGGATCAGAAATTCT-GAAGAATCTAAGCCAGGTTGCAAT GAGGT-GTCGCTGCAGCAGCATGCACTTCTTGGTAGCA-GAATGGAATGAACCATCCAT CAACTTCTATAAAAGAAGAGGTGCTTCTGATCT-GTCCAGTGAAGAGGGTTGGAGACT GTTCAAGATC-GACAAGGAGTACTTGCTAAAAATGGCAACAGAG-GAGTGAGGAGTGC TGCTGTAGATGACAACCTCCATTCTATTTTA-GAATAAATTCCCAACTTCTCTTGCTTT CTATGCT-GTTTGTAGTGAAATAATAGAATGAGCACCCATTC-CAAAGCTTTATTACCA GTGGCGTTGTTGCATGTTTGAAATGAGGTCTGTT-TAAAGTGGCAATCTCAGATGCAG TTTGGA-GAGTCAGATCTTTCTCCTTGAATATCTTTCGA-TAAACAACAAGGTGGTGTG ATCTTAATATATTTGAAAAAAACTTCATTCTCGT-GAGTCATTTAAATGTGTACAATGT ACACACTGG-TACTTAGAGTTTCTGTTTGATTCTTTTTTAATAAAC-TACTCTTTGATTTA AAAAAAAAAAAAAAAAA (SEQ ID No. 15). Nucleotides 156-671 of SEQ ID No. 15 (SEQ ID NO. 16), which includes the termination codon, comprise the coding region encoding the SSAT polypeptide amino acid sequence (SEQ ID No. 17).

The cDNA of nucleolin was prepared using Superscript III one-step RT-PCR (Invitrogen) and 500 nanogram (ng) of HEK 293T cells total RNA. Primers used to prepare the cDNA were: Forward: 5' ATG GTG AAG CTC GCG AAG GC 3' (SEQ ID NO. 70) and Reverse: 5' GGG AAA GCA GAG GGA CAG AAG C 3' (SEQ ID No. 71). The PCR product was gel purified, cloned in pGEM® T vector (Promega, Madison, Wis.), and was verified by sequencing.

Cell Culture and Plasmids for Protein Expression:

HEK 293T cells (ATCC) were grown in DMEM supplemented with 10% Fetal Bovine Serum (FBS). The pLEX-MCS plasmid (Open Biosystems, Huntsville, Ala.) was used for the expression of recombinant proteins. The plasmid was modified to include a C-term purification tag containing a strep tag sequence and His-6 (SEQ ID NO: 72) sequence (Giannone et al., 2007, Biotechniques 43(3):296, 298, 300). All DNA oligos were from Integrated DNA Technologies (IDT).

Lipofectamine 2000 (Invitrogen) was used for plasmid transfection following the manufacturer recommendations. A HEK 293T stable cell line having the ORF SSAT was selected using Puromycin following manufacturer recommendations (Open Biosystems, Huntsville, Ala.).

Cytoplasmic Extracts:

Cytoplasmic fractions of HEK 293T were obtained following a cellular lysis in a hypotonic buffer (0.1×PBS, 0.001% Triton X-100, Protease inhibitors cocktail (Thermofisher)). Briefly, hypotonic lysis buffer (200 μL) was added to the HEK293T cell pellet. The resulting suspension was agitated by pipetting and was placed in ice for 15 min. Following incubation, the suspension was vortexed for 1 minute and centrifuged at 16,000 g for 30 min. The supernatant was collected and the protein quantified by the Bradford method (Biorad). This cytoplasmic fraction was used as the source of protein for the RNA-protein interaction studies.

SSAT Recombinant Constructs:

The following twelve SSAT constructs were created: ORF SSAT; Δ4-30; Δ4-45; Δ4-75; Δ52-117; Δ31-75; 5UTR+SSAT; 5UTR+Δ4-30SSAT; 5UTR+Δ49-114SSAT; 5UTR (ΔuORFs)+SSAT; 5UTR(ΔuORFs)+Δ4-30SSAT; and 5UTR (ΔuORFs)+Δ49-114SSAT. The first 6 constructs were generated by performing PCR with a common reverse primer: 5' TCC CAC CGG TCT CCT CTG TTG CCA TTT TTA GC 3' (SEQ ID No. 22) containing a restriction site for AgeI (italicized) and which anneals to the 3' end of the SSAT coding sequence, excluding the termination codon. The 6 forward primers contain a BamHI (italicized) restriction site and the Kozak sequence (lowercase), shown in 5' to 3' orientation in Table 5

TABLE 5

| SSAT construct | Forward primer sequence | SEQ ID No. |
|---|---|---|
| WT_ORFSSAT | CGG GAT CCg ccg cca cca tgG CTA AAT TCG TGA TCC G | 23 |
| Δ 4-30_ORFSSAT | CGG GAT CCg ccg cca cca tgG CCG CCG ACT GCA GTG AC | 24 |
| Δ 4-45_ORFSSAT | CGG GAT CCg ccg cca cca tgG ACA TAC TGC GGC TGA TCA AG | 25 |
| Δ 4-75_ORFSSAT | CGG GAT CCg ccg cca cca tgA AAT ATG AAT ACA TGG AAG AAC AAG | 26 |
| Δ 31-75_ORFSSAT | CGG GAT CCg ccg cca cca tgG CTA AAT TCG TGA TCC GCC CAG CCA CTA AAT ATG AAT ACA TGG AAG AAC AAG | 27 |
| Δ 52-117_ORFSSAT | CGG GAT CCg ccg cca cca tgG CTA AAT TCG TGA TCC GCC CAG CCA CTG CCG CCG ACT GCA GTG ACA TAG ATC TGC TAG AAG ATG GTT TTG G | 28 |

The PCR products obtained with these oligo pairs were purified with PCR clean-up kit (Promega), digested with BamHI and AgeI (Fermentas) and ligated in the pLEX-MCS plasmid. The composition of all the clones was confirmed by sequencing.

Three additional different versions of SSAT were produced as follows. The construct "5'UTR(–155 bp)+ORF_SSAT" was created with the forward primer: 5' CGG GAT CCC TGG TGT TTA TCC GTC ACT CG 3' (SEQ ID No. 29) containing the BamHI restriction site (italicized) and the common reverse primer above (SEQ ID No. 22).

The construct "5'UTR(–155 bp)+ORF Δ4-33_SSAT" was created by ligating two PCR products (segment 1A and segment 2) after digestion with BglII. The first PCR product "segment 1A" was created with forward primer: 5' CGG GAT CCC TGG TGT TTA TCC GTC ACT CG 3' (SEQ ID No. 30) containing BamHI restriction site (italicized) and reverse primer: 5' TAG CAG ATC TTT TTC AGT TAA GAT TAC TTG TTC TTC CAT GTA TTC ATA TTT AGC CAG CTC CTT GAT CAG CCG CAG TAT GTC ACT GCA GTC GGC CAT TTT CGT CTT TTG CTT TTC TT 3' (SEQ ID No. 31) containing a BglII site (italicized).

The second PCR product "segment 2" was generated with forward primer: 5' GAA AAA GAT CTG CTA GAA GAT GGT T 3' (SEQ ID NO. 32) containing a BglII site and reverse primer: 5' TCC CAC CGG TCT CCT CTG TTG CCA TTT TTA GC 3' (SEQ ID NO. 33) containing a restriction site for AgeI (italicized). Segment 1A and segment 2 PCR products were cleaned-up, digested with BglII, and ligated with T4 DNA Ligase (Invitrogen). A third PCR reaction was setup using this ligation product as template, the forward primer of segment 1A, and the reverse primer of segment 2. The resulting PCR product was digested with BamHI and AgeI, and ligated in the expression plasmid.

The construct "5'UTR(–155 bp)+ORF Δ 49-114_SSAT" was generated using the same technique. A PCR product "segment 1B" was created with the same forward primer for segment 1A and the reverse primer: 5' TAG CAG ATC TTT GTC ACT GCA GTC GGC GGC 3' (SEQ ID NO. 34). The resulting PCR product was cleaned-up, digested with BglII, and ligated with segment 2. A third PCR reaction was setup using the forward primer of segment 1A, the reverse primer of segment 2 and the ligation reaction product between segment 1B and segment 2 as template. The resulting PCR product was digested with BamHI and AgeI, and ligated in the expression plasmid.

Three additional variants of SSAT with shorter versions of the 5' UTR lacking the AUG codons of the two uORFs were created using the forward primer: 5'CGG GAT CCC CAC CTC CTC CTA CTG TTC AAG TA 3' (SEQ ID No. 35) containing BamHI (italicized) and reverse primer: 5' TCC CAC CGG TCT CCT CTG TTG CCA TTT TTA GC 3' (SEQ ID NO. 36) containing AgeI (italicized). Previously described constructs "5'UTR(–155 bp)+ORF_SSAT"; "5'UTR(–155 bp)+ORF Δ 4-33_SSAT"; and "5'UTR(–155 bp)+ORF Δ 49-114_SSAT" were each used as templates to generate PCR products "5'UTR(–66 bp)+ORF_SSAT"; "5'UTR(–66 bp)+ORF Δ 4-33_SSAT"; and "5'UTR(–66 bp)+ORF Δ 49-114_SSAT", respectively.

Nucleolin Recombinant Constructs:

Five recombinant fragments of nucleolin, "N-term"; "R1234"; "R1234GAR"; "R1-2"; and "R3-4", were expressed using the modified pLEX-MCS (Open Biosystems) vector. The segments were amplified by PCR, digested with both BamHI and AgeI, and ligated into the pLEX-MCS expression plasmid. The integrity of all the constructs was verified by sequencing. The oligos used to amplify each nucleolin fragment are shown in Table 6. In all of the forward (F) primers, the restriction site for BamHI is italicized and the Kozak sequence is in lowercase. In all the reverse (R) primers, the restriction site for AgeI is italicized.

TABLE 6

| Nucleolin fragment | | Primer in 5' to 3' orientation | SEQ ID No. |
| --- | --- | --- | --- |
| N-term | F | CGG GAT CCg ccg cca cca tgG TGA AGC TCG CGA AGG | 37 |
| N-term | R | TCC CAC CGG TAG TCG GTT CTG TGC CTT CCA | 38 |
| R1234GAR | F | CGG GAT CCg ccg cca cca tgA CGG CTT TCA ATC TCT TTG TTG | 39 |
| R1234GAR | R | TCC CAC CGG TTT CAA ACT TCG TCT TCT TTC CTT G | 40 |
| R1234 | F | CGG GAT CCg ccg cca cca tgA CGG CTT TCA ATC TCT TTG TTG | 41 |
| R1234 | R | TCC CAC CGG TTT CAC CCT TAG GTT TGG CCC | 42 |
| R12 | F | CGG GAT CCg ccg cca cca tgA CGG CTT TCA ATC TCT TTG TTG | 43 |
| R12 | R | TCC CAC CGG TTT GAC CTT TCT CTC CAG TAT AGT ACA G | 44 |
| R34 | F | CGG GAT CCg ccg cca cca tgG AAT CAA AAA CTC TGG TTT TAA GC | 45 |
| R34 | R | TCC CAC CGG TTT CAC CCT TAG GTT TGG CCC | 46 |

Stem Loop-GFP Recombinant Constructs:

Two constructs having the eGFP gene were prepared, called "eGFP" and "Loop eGFP." Plasmid pLVTHM (AddGene, Cambridge, Mass., Addgene(dot)org, clone number 12247) was used as template to amplify the eGFP gene by PCR. The PCR products were digested with BamHI and AgeI, and cloned in the pLEX-MCS vector described above. The construct called "eGFP" was created with the following primers: Forward primer 5' cgG GAT CCg ccg cca cca tgG TGA GCA AGG GCG AG 3' (SEQ ID No. 47) and Reverse primer 5' TCC CAC CGG TTC GAG ATC TGA GTC CGG ACT T 3' (SEQ ID No. 48). The construct called "Loop eGFP" was created with the Forward primer 5' cgG GAT CCg ccg cca cca tgG CTA AAT TCG TGA TCC GCC AGG CCA CTG CCG CCG ACT GCA GTG ACA TAC TGC GGC TGA TCA AGG AGC TGG CTA TGG TGA GCA AGG GCG AG 3' (SEQ ID NO. 49) and the reverse primer (SEQ ID No. 48) used for "eGFP." In the forward primers, the restriction site for BamHI is italicized and the Kozak sequence is in lowercase. In the reverse primer, the restriction site for AgeI is italicized.

SSAT RNA Chimera to Identify RNA-Interacting Proteins:

In order to isolate proteins interacting with the SSAT RNA, a chimeric RNA was designed and produced by an in vitro transcription (IVT). A DNA template for IVT was created by linking the first 170 and the last 180 nucleotides of the open reading frame of SSAT with the RNA aptamer sequence specific for streptomycin binding. This aptamer contained an internal recognition site for the restriction enzyme BanI.

To generate the DNA template for IVT, a set of primers were designed to amplify the first 170 bp of the SSAT ORF: forward: 5'TAATACGACTCACTATAGGGA TGG CTA AAT TCG TGA TCC G 3' (SEQ ID No. 50); and reverse: 5' CCG TGG TGC CCT TGC GGG CAG AAG TCC AAA TGC GAT CCT TCG CAA CCA GGC AGT GGT AAA AG 3' (SEQ ID No. 51). The forward primer contains the T7 promoter region (underlined), and the reverse primer contains part of the sequence of the RNA aptamer including the BanI recognition site (italicized). The resulting amplicon is called "section 1."

The last 180 bp of the ORF of SSAT were amplified using the following primers: forward: 5' CAA GGG CAC CAC GGT CGG ATC CTC TAA GCC AGG TTG CAA TGA G3' (SEQ ID No. 52); and reverse: 5' TCA CTC CTC TGT TGC CAT TTT T 3' (SEQ ID No. 53). The forward oligo contains the rest of the sequence of the streptomycin binding aptamer starting with the BanI sequence (italicized). The resulting amplicon is called "section 2."

Both section 1 and section 2 were digested with BanI, purified and ligated with T4 DNA ligase (Invitrogen). The ligated product was used as template in a PCR reaction comprising the forward primer used to create section 1 and the reverse primer used to create section 2. The product of this reaction was gel-purified, cloned in pGEM® T vector (Promega, Madison, Wis.), and verified by sequencing. Using the forward primer from section 1 and the reverse primer for section 2, PCR using the resulting pGEM-derived plasmid containing the chimera design as template was performed. The PCR product was purified using a PCR clean-up kit (Promega) and 200 ng of the product were used per each IVT reaction. TranscriptAid™ T7 High Yield Transcription Kit (Fermentas, Glen Burnie, Md.) was used, as directed by the manufacturer, for the IVT reaction. The resulting molecule is termed "1-516".

Identification of RNA-Interacting Proteins:

RNA-interacting proteins were isolated using a recently reported method (Windbichler et al., 2006, Nat Protocols 1(2):637-640). Briefly, 150 microgram of the previously described chimeric SSAT RNA molecule was obtained using a high yield T7 in vitro transcription system following the manufacturer instructions (Fermentas). The chimera was purified using Megaclear (Ambion) and eluted with 100 μl of the provided elution buffer. The chimera was renatured in a thermocycler using the following cycle: 5 minutes at 56° C. and 10 minutes 37° C. A volume of 900 μl of column buffer (50 mM Tris HCL, pH 7.5, 5 mM MgCl2, 250 mM NaCl) was added to the RNA chimera and kept on ice. A Sepharose-streptomycin purification column was prepared as previously described (Duan et al, 2010, Proteomics 10(11):2165-2174). To prevent non-specific binding, the column was blocked with 20 μg yeast tRNA (Ssigma) per 1 ml column buffer. The chimeric SSAT RNA was added to the column and was left to interact for 10 minutes. After washing the column, 1 mg of a cytoplasmic protein fraction resuspended in 1 ml of the column buffer, was added to the column. The lysate was left to interact for 10 minutes with the RNA chimera. The column was washed 8 times with 1 ml of column buffer, and the bound proteins were eluted with 2 ml of 10 μM streptomycin in column buffer. The eluants were concentrated to 50 μL using a Nanosep 3000 (Pall Corp) and separated with SDS-PAGE. The gel was stained with Sypro ruby (Invitrogen). The bands were cut and identified by GeLCMS technology using a Bruker HCT ultra ion trap mass spectrometer as previously described (Duan et al., 2010).

Six truncated RNA-chimera molecules were prepared to identify the segment of SSAT mRNA recognized by nucleolin. The six RNA truncated constructs were generated using the same procedure described above for the chimeric RNA construct having the first 170 and the last 180 nucleotides of the open reading frame of SSAT. The oligonucleotides (oligos) used to prepare the 6 additional truncated molecules are depicted in 5' to 3' orientation in Table 7, where F denotes the forward primer and R denotes the reverse primer. The T7 promoter sequence is underlined in each forward primer.

TABLE 7

| RNA bait | | SEQ ID No. | Primer Sequence |
|---|---|---|---|
| 1-516 | F | 54 | TAATACGACTCACTATAGGGATGGCTAAATTCGTGATCCG |
| 1-516 | R | 55 | TCACTCCTCTGTTGCCATTTTT |
| 50-516 | F | 56 | TAATACGACTCACTATAGGGTACTGCGGCTGATCAAGGAG |
| 50-516 | R | 57 | TCACTCCTCTGTTGCCATTTTT |
| 1-486 | F | 58 | TAATACGACTCACTATAGGGATGGCTAAATTCGTGATCCG |
| 1-486 | R | 59 | CTCCTTGTCGATCTTGAACAGTC |
| 50-486 | F | 60 | TAATACGACTCACTATAGGGTACTGCGGCTGATCAAGGAG |
| 50-486 | R | 61 | CTCCTTGTCGATCTTGAACAGTC |
| 118-486 | F | 62 | TAATACGACTCACTATAGGGGATCTGCTAGAAGATGGTTTTGG |

TABLE 7 -continued

| RNA bait | | SEQ ID No. | Primer Sequence |
|---|---|---|---|
| 118-486 | R | 63 | CTCCTTGTCGATCTTGAACAGTC |
| 50-417 | F | 64 | TAATACGACTCACTATAGGGTACTGCGGCTGATCAAGGAG |
| 50-417 | R | 65 | GAAGTTGATGGATGGTTCATTCC |
| 118-417 | F | 66 | TAATACGACTCACTATAGGGGATCTGCTAGAAGATGGTTTTGG |
| 118-417 | R | 67 | GAAGTTGATGGATGGTTCATTCC |

RNA-Protein Interaction with Nucleolin Fragments:

The five different fragments of nucleolin "N-term", "R1234GAR," "R1234," "R12," and "R34" were overexpressed by transient transfection as follows. The plasmids the constructs were obtained using high yield plasmid Maxiprep (Promega) and were transiently transfected into 5×10$^6$ HEK293T cells each using Lipofectamine 2000. The cells were allowed to express the recombinant proteins for 48 hours and were then washed 3 times in cold PBS. A cytoplasmic fraction was obtained as above and quantified by the Bradford method (Biorad).

To determine the nucleolin segment interacting with the SSAT mRNA, the following a RNA-protein interaction assay was performed. Five columns of Sepharose-streptomycin were prepared as above and the RNA bait molecule "1-516" (150 μg) was allowed to interact with each of the columns for 10 minutes. After washing the column, 1 mg of a cytoplasmic protein fraction from cells overexpressing each of the recombinant fragments of nucleolin were resuspended in 1 ml of the column buffer and were added to the column. The lysate was left to interact for 10 minutes with the RNA chimera. The column was washed 8 times with 1 ml of column buffer, and the bound proteins were eluted with 2 ml of 10 μM streptomycin in column buffer. The eluents were concentrated to 50 μL using a Nanosep 3000 (Pall Corp), separated with SDS-PAGE and transferred to a nitrocellulose membrane for Western blotting using the anti His-C term-HRP monoclonal antibody.

siRNA Knockdown Experiments:

Six genes (ENO1, SSB, CSDA, YBX1, DHX9, NCL) were targeted by siRNA using one molecule per target of Silencer® Select RNAi (Applied Biosystem, Austin, Tex.). The siRNA ID number provided by the manufacturer is listed in parenthesis: ENO1 (siRNA ID: s 4682), SSB (siRNA ID: s13468), CSDA (siRNA ID: s224989), YBX1 (siRNA ID: s9732), DXH9 (siRNA ID: s4019) and NCL (siRNA ID: s9312) were provided. The transfection of the siRNA into the HEK293T cells was performed according to the manufacturer instructions. Briefly, 600,000 HEK 293T cells stably expressing SSAT WT_ORF were seeded in 6-well plates and transfected with Lipofectamine 2000 (Invitrogen) in Optimem with an siRNA (10 nM). The cells were incubated for 60 hours, and the cytoplasmic fraction was collected as above. The proteins were quantified and analyzed by Western blotting.

Two-Dimensional Gel Electrophoresis and 2D Western Blotting:

Cytoplasmic lysates (40 microgram) from HEK293T cells, and lysates from cells treated for 12 h with 1.5 mM spermine, were subjected to 2DE separation (pI 3-6) as previously described (Boden et al., 2008, Diabetes 57(9): 2438-2444). In addition, a sample of RNA-interacting proteins obtained from a Sepharose-streptomycin-chimeric RNA column described above was subjected to the same 2DE separation. The sample was initially concentrated to 30 µL using a Nanosep 3000 (Pall Corp) and dialyzed with 0.1×PBS for 12 h using a Slide-A-Lyzer 7K mini unit (Pierce Biotech). After separation by 2DE, the proteins were transferred to a nitrocellulose membrane using a Mini Trans Blot System (Biorad) and were Western blotted using anti-nucleolin monoclonal antibody.

Western Blotting and Chemicals:

For Western blots, recombinant proteins were detected with the monoclonal antibody Anti-His(C-term)-HRP (Invitrogen). The following antibodies were from Santa Cruz Biotechnologies: Nucleolin (SC-8031); SSB (SC-80655); CSDA (SC-21318); YBX1 (SC-18057); ENO1 (SC-15343); and β-actin (SC-47778). Spermine was obtained from Sigma, and $N^1$-$N^{11}$ diethylnorspermine ("DENSPM") was kindly provided by Dr. Carl Potter (Roswell Park Cancer Institute, Buffalo, N.Y.).

Luciferase Constructs and Activity Assay:

A chimeric construct (FIG. 15A) comprising a fragment of the 5' UTR of SSAT lacking the uORF's (see FIG. 7), the SSAT coding sequence (see FIG. 8B), and the luciferase coding sequence was prepared. The SSAT coding sequence is linked in-frame to the luciferase coding sequence. The construct was prepared using appropriate primers and template nucleic acid, and conventional PCR methods. The construct was cloned into pLEX-MCS. To evaluate the effect of small molecules on translation of the chimeric construct, the chimeric construct was transiently transfected into HEK293T cells. The small molecule to be tested was added 24 hours after transfection of the vector. Luciferase activity was evaluated 16 hours after the addition of the small molecule using the ONE-Glo™ Luciferase Assay System (Promega, Madison, Wis.). The luminescence intensity was determined using a GloMax® luminometer (Promega).

Dose Response Curve:

The chimeric construct to be tested was transiently transfected into HEK293T cells. Twenty-four hours after transfection of the vector, DENSPM was added to the desired final concentration (ranged from 0.08 micromolar to 40 micromolar). Luciferase activity was evaluated 16 hours after the addition of DENSPM using the ONE-Glo™ Luciferase Assay System. The luminescence intensity was determined using a GloMax® luminometer (Promega). The experiment was run in triplicates to obtain error bars and evaluate reproducibility.

Example 1

Isolation and Characterization of SSAT RNA Binding Protein Repressing Translation A: SSAT RNA Binding Proteins Evidence indicates an unknown protein represses translation by interacting with the coding region of the SSAT transcript (Butcher et al., 2007, J Biol Chem. 282:28530-28539). To identify the unknown protein, repressor candidates were pursued based on the ability to bind to SSAT mRNA. A chimeric RNA containing the first 170 bp and last 181 bp of the human SSAT open reading frame linked to a streptomycin-binding RNA aptamer was prepared (Windbichler et al., 2006, Nature Protocols 1(2):638-U634) (FIG. 9A). The chimeric RNA was immobilized to a column of Sepharose-streptomycin. After incubating HEK293T cell lysate on the column, unbound proteins were washed from the column, RNA binding proteins were eluted then identified by gel electrophoresis liquid chromatography mass spectroscopy (GeLC-MS). A control column containing aptamer-linked GFP RNA did not bind proteins (FIG. 9B).

Six proteins were isolated by the SSAT RNA column: enolase 1 (ENO1), Y box protein 1 (YBX1), DNA-binding protein A (CSDA), La protein (SSB), ATP dependent RNA helicase A (DHX9) and nucleolin (NCL) (FIG. 9B).

Figure 9C:
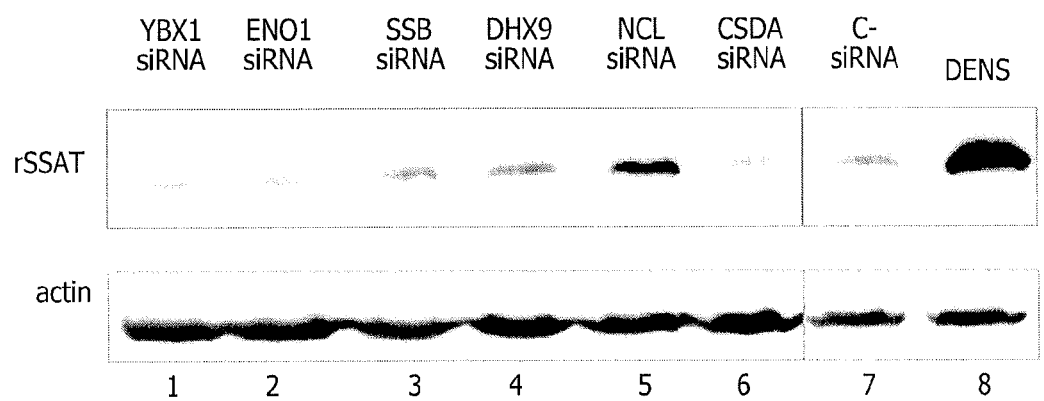

To assess whether candidate proteins repress SSAT translation, each was selectively knocked down using RNA interference (siRNA) in HEK293T cells 6 overexpressing SSAT mRNA. Knockdown efficiency was demonstrated by Western blot for all but DHX9 (antibodies available for DHX9 did not produce useful blots). Only nucleolin knockdown enhanced SSAT expression (FIG. 9C, lane 5). This results suggests that nucleolin is the SSAT translation repressor.

B: Nucleolin SSAT Binding Domain

Figure 10A:
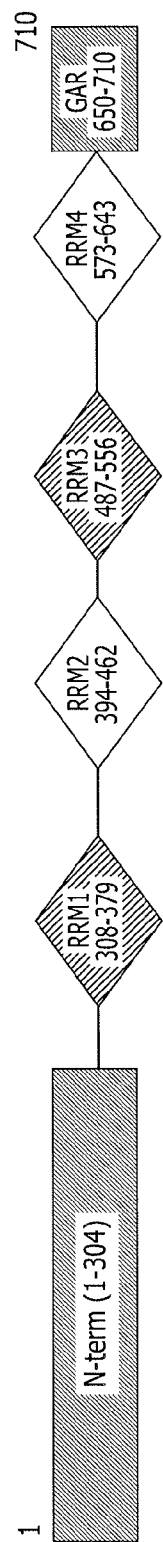
FIGS. 10A-10D relate to data characterizing nucleolin binding to SSAT mRNA.
Figure 10D:
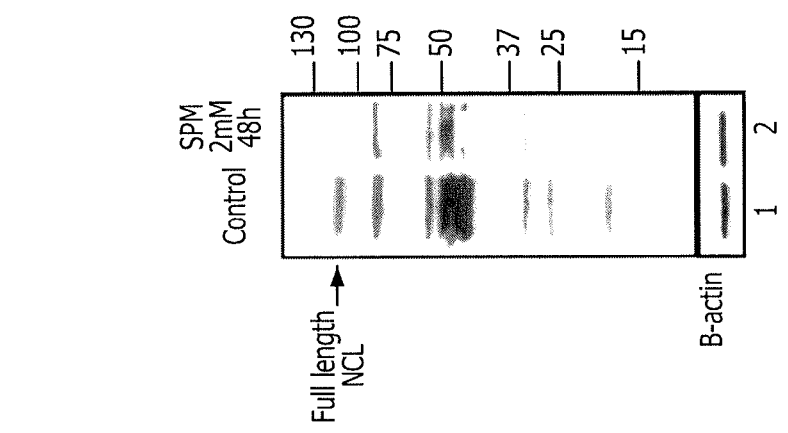
Figure 10C:
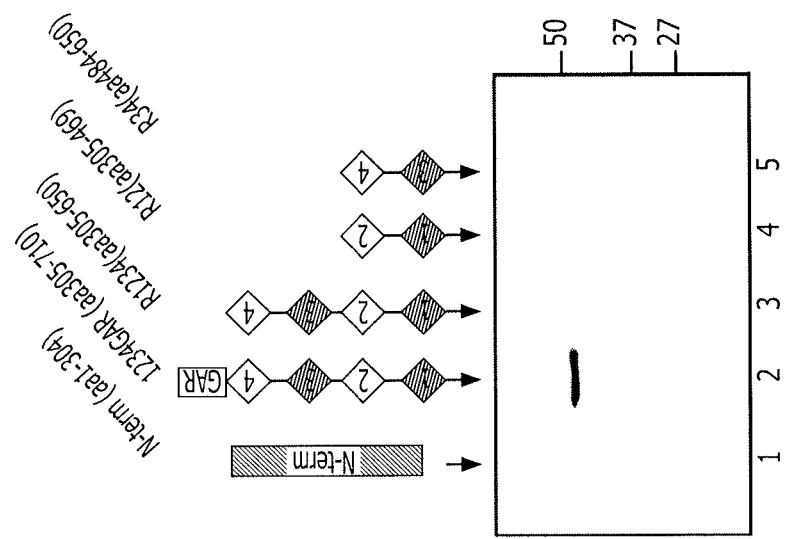
Figure 10B:
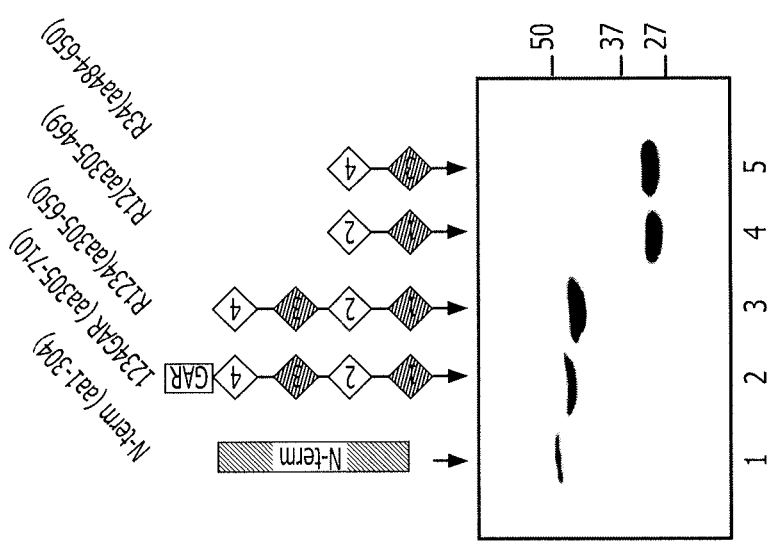

Nucleolin contains 6 domains (FIG. 10A): N-terminal (N-Term), RNA-binding motifs (RRM1, RRM2, RRM3, RRM4), and C-terminal glycine/arginine-rich (GAR) domain (Tuteja et al., 1998, Critical Reviews in Biochemistry and Molecular Biology 33(6):407-436). To determine which domain binds to SSAT mRNA, HEK293T cells were transiently transfected to produce recombinant nucleolin fragments. To increase binding stringency, lysates rather than isolated protein fragments were incubated with individual chimeric SSAT RNA columns that were processed as above (FIG. 10B). The composite Western blot of eluted proteins demonstrates that the GAR domain of nucleolin is necessary for binding (FIG. 10C).

To examine the possibility that increased polyamines cause degradation of nucleolin, the effect of spermine added to HEK293T cells was examined. FIG. 10D depict Western blots of lysates of HEK293T that were exposed to 2 mM spermine for 48 hours and untreated controls. The multiple reacting bands result from ongoing nucleolin autocatalysis. The 105 KDa band in the control lane is intact nucleolin, and the lower bands reflect regular ongoing degradation (Fang et al., 1993, Experimental Cell Res. 208(1):48-53). Nucleolin appears at a higher MW than its theoretical size due to the presence of a high content of negatively charged residues at the N-terminal. The 105 Kda band is missing in the experimental lane, and there is an overall reduction of material reacting with the anti-nucleolin monoclonal antibody. These data indicate the presence of a negative feedback system to control excess polyamines that involves nucleolin and SSAT.

Figure 11A:
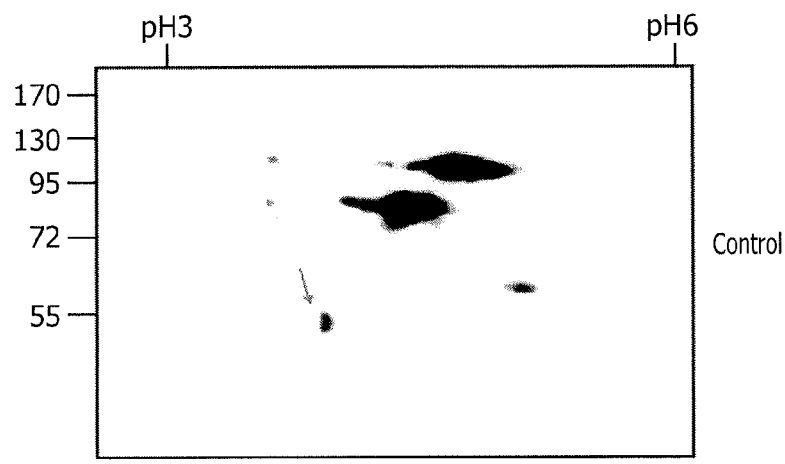
FIGS. 11A-11C depicts 2D-PAGE Western blots prepared from HEK293T cells exposed to 2 mM spermine for 12 hours (FIG. 11B), controls not exposed to spermine (FIG. 11A), and control cell proteins eluted from a chimeric SSAT RNA column (FIG. 11C). The arrows indicate the nucleolin isoform that binds to SSAT-RNA.
Figure 11B:
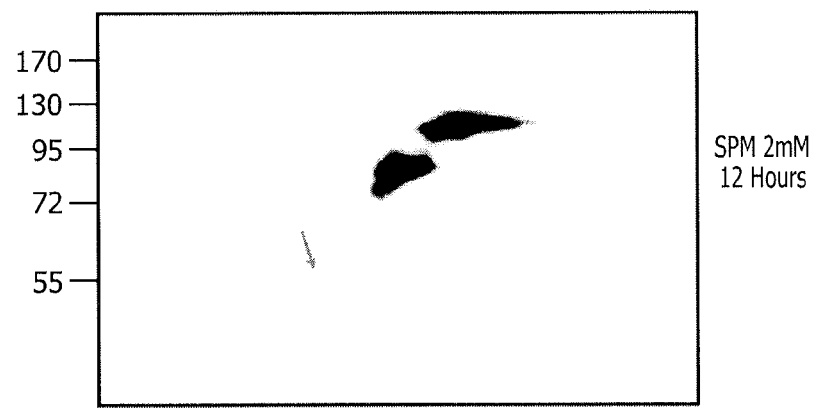
Figure 11C:
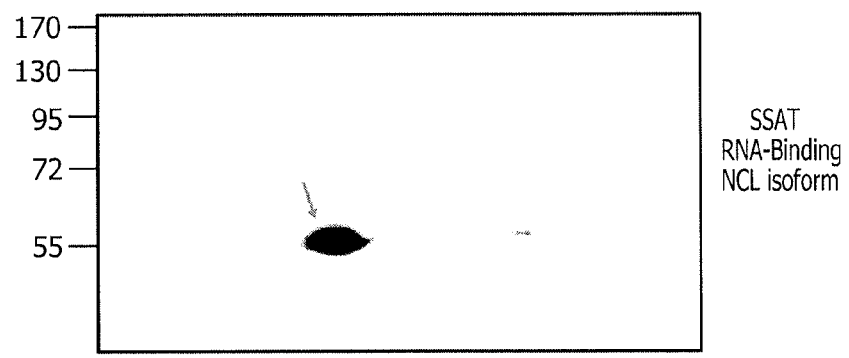

Nucleolin exists in cells as multiple isoforms due to ongoing autocatalysis. Experiments were designed to determine whether spermine-induced degradation and SSAT RNA binding are isoform-specific. FIGS. 11A-11C depict 2D-PAGE Western blots prepared from HEK293T cells exposed to 2 mM spermine for 12 hours, controls not exposed to spermine, and control cell proteins eluted from a chimeric SSAT RNA column. A 55 KDa nucleolin isoform present in the control cells is absent in cells exposed to spermine and is enriched in the material eluted from the column. Mass spectroscopic analysis of material from the column identified partial sequences for four peptides, all of which are contained within in the C terminal of nucleolin and span across all four RNA binding domains. Thus the repressor likely contains both the GAR and RNA-binding regions of nucleolin. Because the cells were incubated with spermine for 12 hr as compared to the 48 hr in the SDS-PAGE (FIG. 10D), the intact nucleolin (105 Kda) is not entirely degraded.

Figure 12A:
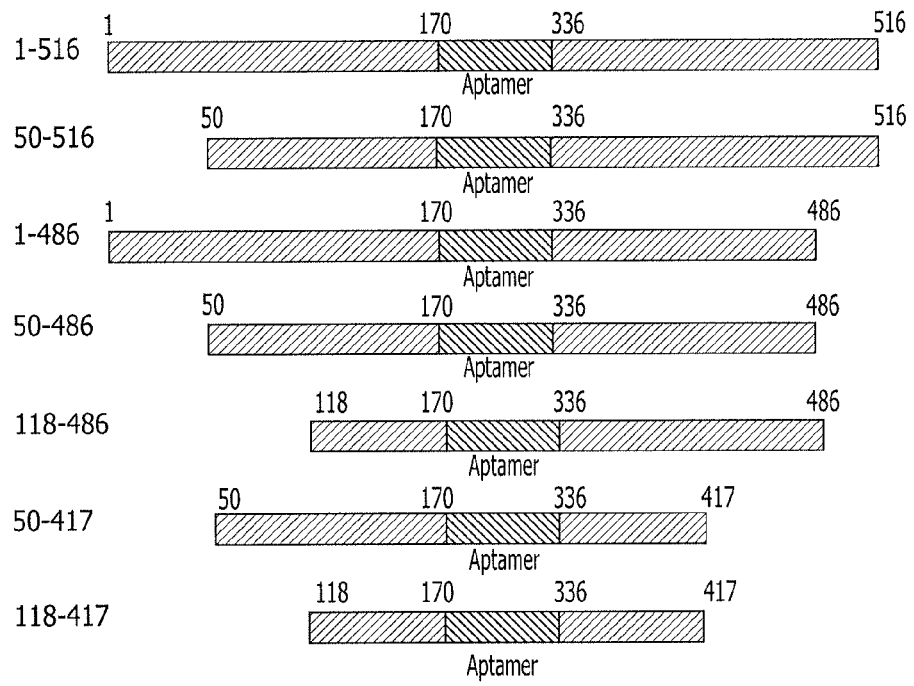
FIGS. 12A-12C relate to data identifying SSAT mRNA bases essential for nucleolin binding and translation repression.
Figure 12B:
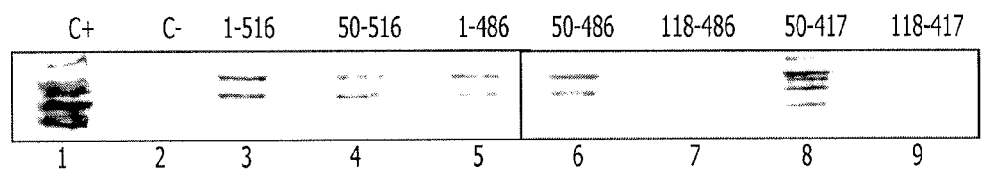

Further information on control of SSAT translation was gained by determining the region of SSAT mRNA to which nucleolin binds. In addition to the Sepharose-streptomycin-chimeric SSAT RNA column described above, six additional columns were made using truncated constructs of the chimeric RNA (FIG. 12A). Western blots of material bound to, then eluted from, the set of seven Sepharose-streptomycin-chimeric RNA columns shows that all of the chimera columns bound nucleolin except those lacking nucleotides 50-118 (FIG. 12B). These data indicate that that nucleolin binding to SSAT mRNA depends on nucleotides within nucleotides 50-118.

C: Stem Loop in 5' End of SSAT ORF

Figure 12C:
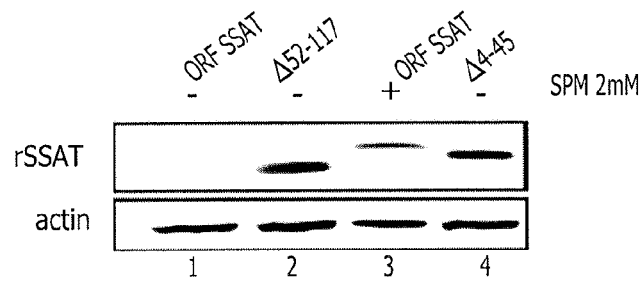
Figure 13A:
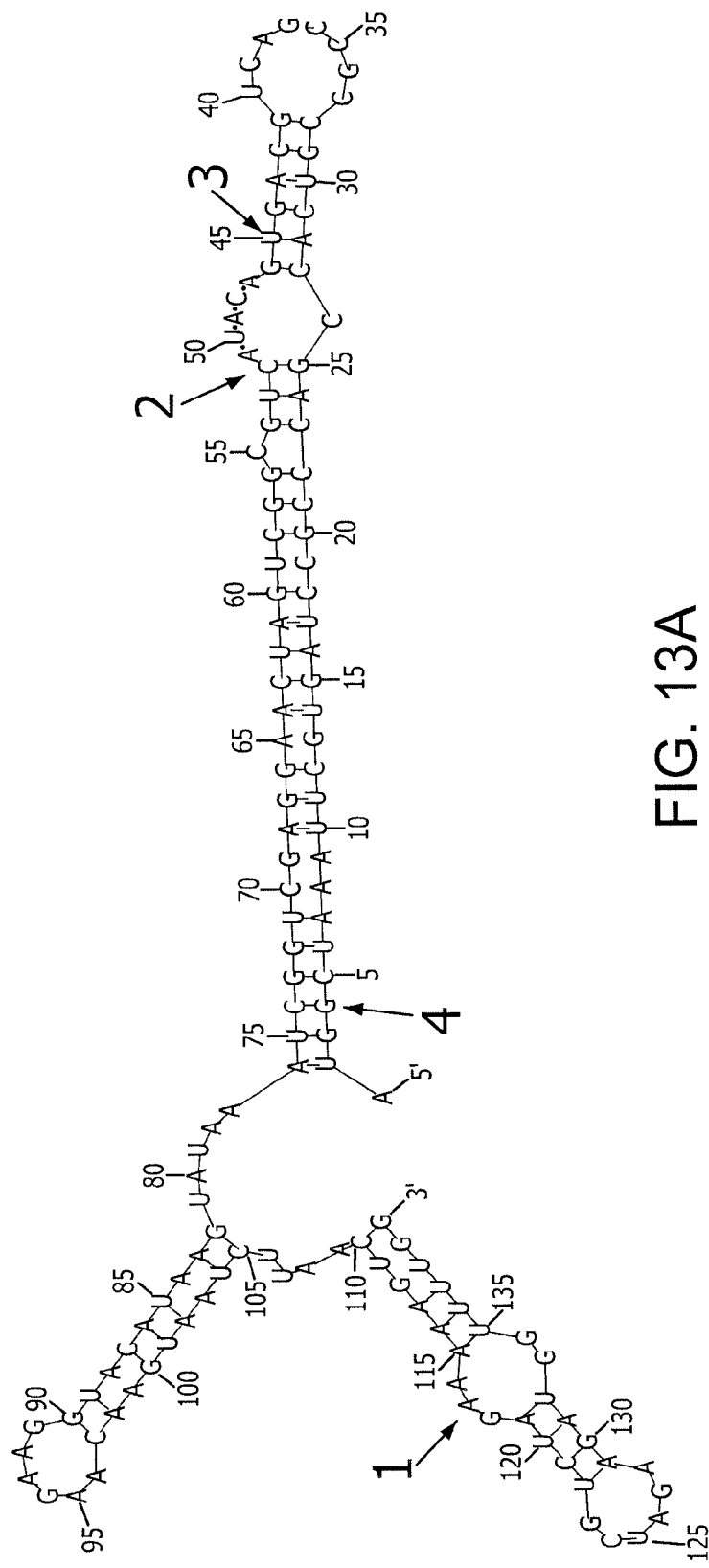

SSAT expression by a mutant lacking nucleotides 52-117 (reading frame maintained) was assessed and compared to cells expressing unmodified SSAT ORF. The mutant lacked repression control (FIG. 12C, lane 2). A Δ4-45 mutant was also prepared and SSAT expression assessed. Repression was also released for this mutant (FIG. 12C, lane 4). Mfold (Zuker, 2003, NAR 31(13):3406-3415) was used to search for secondary structure in the SSAT ORF mRNA sequence. A 75 basepair stem loop at the 5' end of the ORF (nucleotides 2-76) with a free energy of −30.8 kcal/mol was predicted (FIG. 13A). The predicted step loop is not an artifact created by analysis of ORF only because the loop was also predicted when the full cDNA sequence was used in the MFold program.

A stem loop structure very close to the 5' cap end with a free energy of −30 kcal/mol can block mRNA translation (Kozak, 1989, Mol Cell Biol. 9(11):5134-5142). RNA secondary structure prediction of both the Δ4-45 and Δ52-117 mutants indicates the impairment to form this stem loop. Three additional mutants lacking the stem loop were constructed (Δ4-75, Δ4-30, Δ31-75) and expressions by these mutants were compared to that of the ORF of SSAT. The results are depicted in FIG. 13B. Elimination of the stem loop in the three mutants allowed greater SSAT expression (lanes 2-4) compared to cells having the complete SSAT ORF upon exposure to exogenous spermine (lane 5).

To investigate whether this loop could repress translation of other proteins, the first 75 bp of the SSAT ORF was spliced onto the 5' end of a reporter gene ORF (eGFP). The presence of the SSAT stem loop diminished GFP expression (compare lanes 1 and 2, FIG. 13C). The repression effect could be partially reversed by exogenous spermine. (FIG. 13C, lane 3).

The mRNA of human SSAT contain a long 5' UTR. This long 5' UTR situates the SSAT stem loop formed by nucleotides 2-76 of the coding region downstream from the 5' cap of the mRNA by 242 nucleotides. The capacity of a loop to stop translation depends on its proximity to the 5' cap. Loops displaced by 50 bp downstream lose capacity to stop translation (Kozak, 1989, Mol Cell Biol. 9(11):5134-5142). The following experiment was performed to study whether the stem loop of nucleotides 2-76 is important to maintain translational repression in the position where it naturally occurs in the mRNA transcript.

The expression of two mutants unable to form the stem loop and containing the complete 5' UTR was evaluated. The first mutant (5' UTR+Δ4-30 SSAT) lacks the first half of the loop but can bind nucleolin. The second mutant (5' UTR++ Δ49-114 SSAT) lacks both the stem loop and the nucleolin binding region. Both mutants were able to over-express SSAT compared to the 5' UTR+SSAT clone. The expression of SSAT in 5' UTR Δ49-114 SSAT was higher upon the addition of spermine (FIG. 13D). These data indicate that the presence of the long 5' UTR does not block the ability of the stem loop to maintain translational repression and that nucleolin is probably stabilizing this structure.

Example 2

Translation Control of SSAT by Upstream ORFs

Upstream ORFs (uORFs) can modulate translation (Calvo et al., 2009, PNAS 106(18):7507-7512). The ribosomal scanning model of translation initiation indicates that translation usually starts once the 43S ribosomal subunit finds the first AUG codon. The presence of uORFs in certain transcripts deludes the ribosome machinery so translation starts upstream of the genuine initiation codon, thus dramatically reducing the translation of the intended protein (Jackson et al., 2010, Nature Reviews Molecular Cell Biology 11(2): 113-127; Kozak, 2005, Gene 361:13-37; Sachs et al., 2006, Genes & Development 20(8):915-921, 32, 33).

SSAT contains two upstream ORFs (uORFs). One uORF begins at −117 and codes for 4 amino acids. The other begins at −74, overlaps the main ORF, and codes for 29 amino acids. The prior art suggests the 5' UTR of SSAT does not play a role in translation repression (Parry et al., 1995, The Biochemical Journal 305 (Pt 2):451-458; Butcher et al., 2007, J Biol Chem. 282:28530-28539).

Despite the prior art results, the effect of these two uORFs on translation repression was examined by constructing mutants similar to the ones described in FIG. 13D but with the uORF initiation codons eliminated by replacing G's with A's. Unexpectedly, uORF elimination increased expression upon the addition of spermine compared to the 5' UTR+ SSAT clone (FIG. 14A). The highest expression was observed for the mutant lacking both the uORFs and the stem loop nucleolin binding region, which indicates that these repression systems are independent.

Figure 14B:
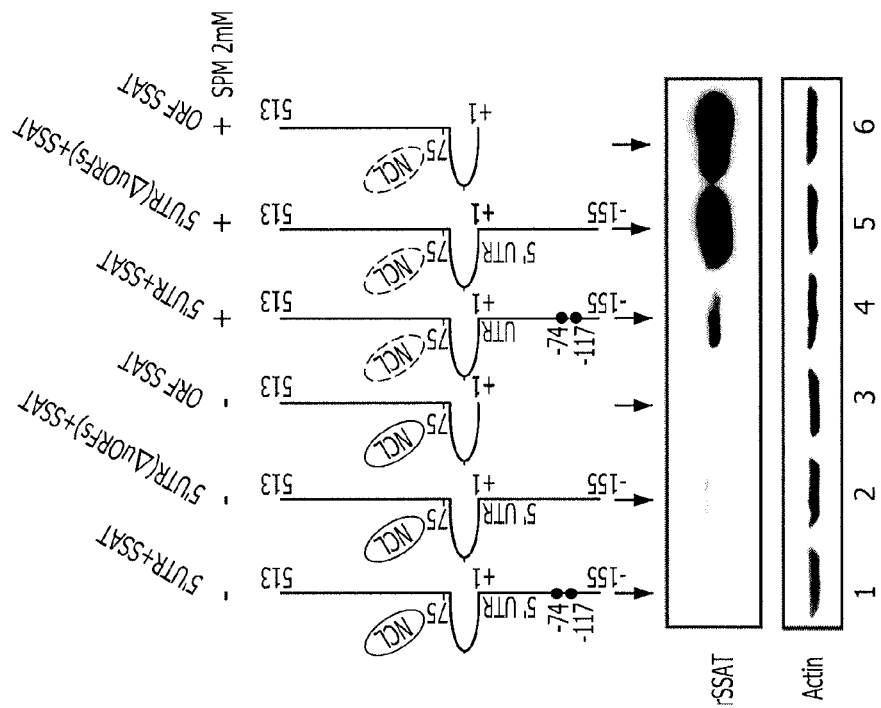
FIGS. 14A and 14B relate to studies of translation control of SSAT by upstream open reading frames (uORFs).
Figure 14A:
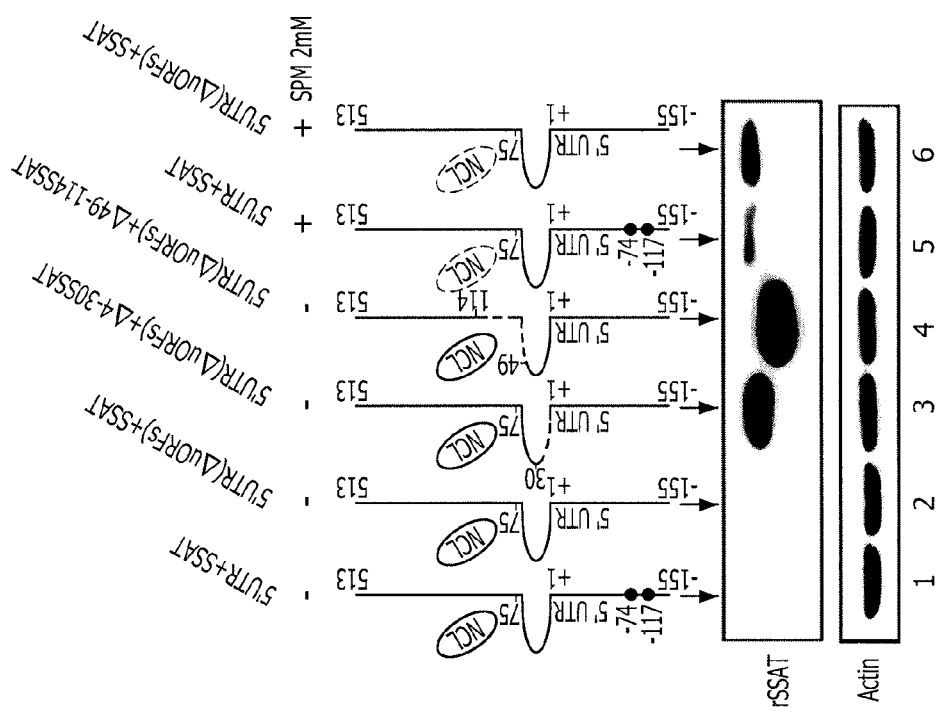

Spermine stimulated expression in mutant with or without uORFs, however the expression levels are dramatically higher in the absence of the uORFs (FIG. 14B). Thus, an increase in spermine level does not allow the translation machinery to bypass the uORFs. Collectively these results indicate that the uORFs act as a polyamine-independent constitutive barrier for ribosome read-through. Removal of the uORFs by either mutation or deletion overcomes this contribution to translational repression of the native SSAT mRNA.

Example 3

Reporter System to Detect Pharmacophores

In view of the discovery of the contribution of uORF's on translational repression of SSAT mRNA, a reporter system was developed to detect pharmacophores that can modulate SSAT translation. The reporter system is a chimeric construct comprising a 5' UTR lacking the uORF's and the SSAT coding sequence linked in-frame to the luciferase coding sequence. (FIG. 15A). The 5' UTR comprises 66 nucleotides of the native 5'UTR immediately upstream of the starting AUG codon.

Release of translational repression of the chimeric construct was tested in the presence of several small molecules. Release of translational repression was assessed by detection of luciferase activity. The small molecules tested were: DENSPM and three uncharacterized polyamine analogs designated polyamine analog 1; polyamine analog 2; and polyamine analog 3. Cisplatin and 5-FU were tested as negative controls.

The data are depicted in FIG. 15B. The chimeric construct alone has substantially no luciferase activity (compare untreated to blank), indicating that it is fully translationally repressed. The translational repression of the chimeric construct is relieved by DENSPM and by one of the polyamine analogs. Translation of the chimeric construct in the presence of the other two polyamine analogs, cisplatin, or 5-FU, is about the same as in the absence of a small molecule (untreated). These data indicate that release by DENSPM and polyamine analog 2 of translational repression of the chimeric construct is specific. Accordingly, the chimeric construct is useful as a reporter system to test candidate agents for efficacy in relieving translational repression of SSAT mRNA.

Example 4

Control of SSAT Translation by 3' End of ORF

Several constructs were prepared to examine the possible role of the 3' end of the SSAT ORF on translational repression. A first construct "Loop GFP" comprises the stem loop nucleotides of the 5' SSAT coding region (nucleotides 2-76) linked in-frame to the coding sequence for green fluorescent protein. A second construct "Loop GFP-SAT1 400-513" was prepared comprising the stem loop nucleotides of the 5' SSAT coding region (nucleotides 2-76) linked in-frame to the coding sequence for GFP, which is linked in frame to nucleotides 400-513 of the SSAT ORF. A third construct "Loop GFP-SAT1 454-513" was prepared comprising the stem loop nucleotides of the 5' SSAT coding region (nucleotides 2-76) linked in-frame to the coding sequence for GFP, which is linked in-frame to nucleotides 454-513 of the SSAT ORF. The constructs were cloned into plasmid pLEX-MCS.

Translation was assessed by detecting the presence of GFP in Western blots. Constructs were transiently transfected into HEK293T cells. Forty-eight (48) hours later, the cells were collected and protein lysates were prepared. The protein in the lysates were separated using SDS-PAGE and the transferred into a nitrocellulose membrane for Western blotting.

Figures 16A, 16B:
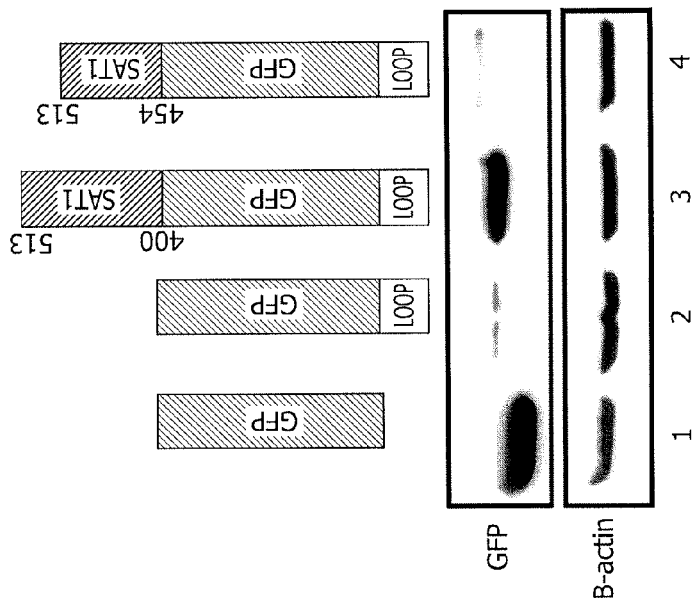
FIGS. 16A and 16B relate to studies of the effect of the 3' end of the SSAT coding region on translation repression.

The translation data for these three chimeric constructs, as well as GFP alone, are depicted in FIG. 16A.

The 5' ORF stem loop was able to translationally repress GFP (compare lanes 1 and 2 in FIG. 16A). Unexpectedly, the addition of nucleotides 400-513 to the 3' end of GFP relieved the translational repression, resulting in activated translation (compare lanes 2 and 3 in FIG. 16A). In contrast, addition of nucleotides 454-513 to the 3' end of GFP did not relieve the translational repression (lane 4 of FIG. 16A). These data suggest the existence of a regulatory sequence within or comprising nucleotides 400-453 (shown in the box in the sequence depicted in FIG. 16B) that participates in activation of SSAT translation.

Figure 17A:
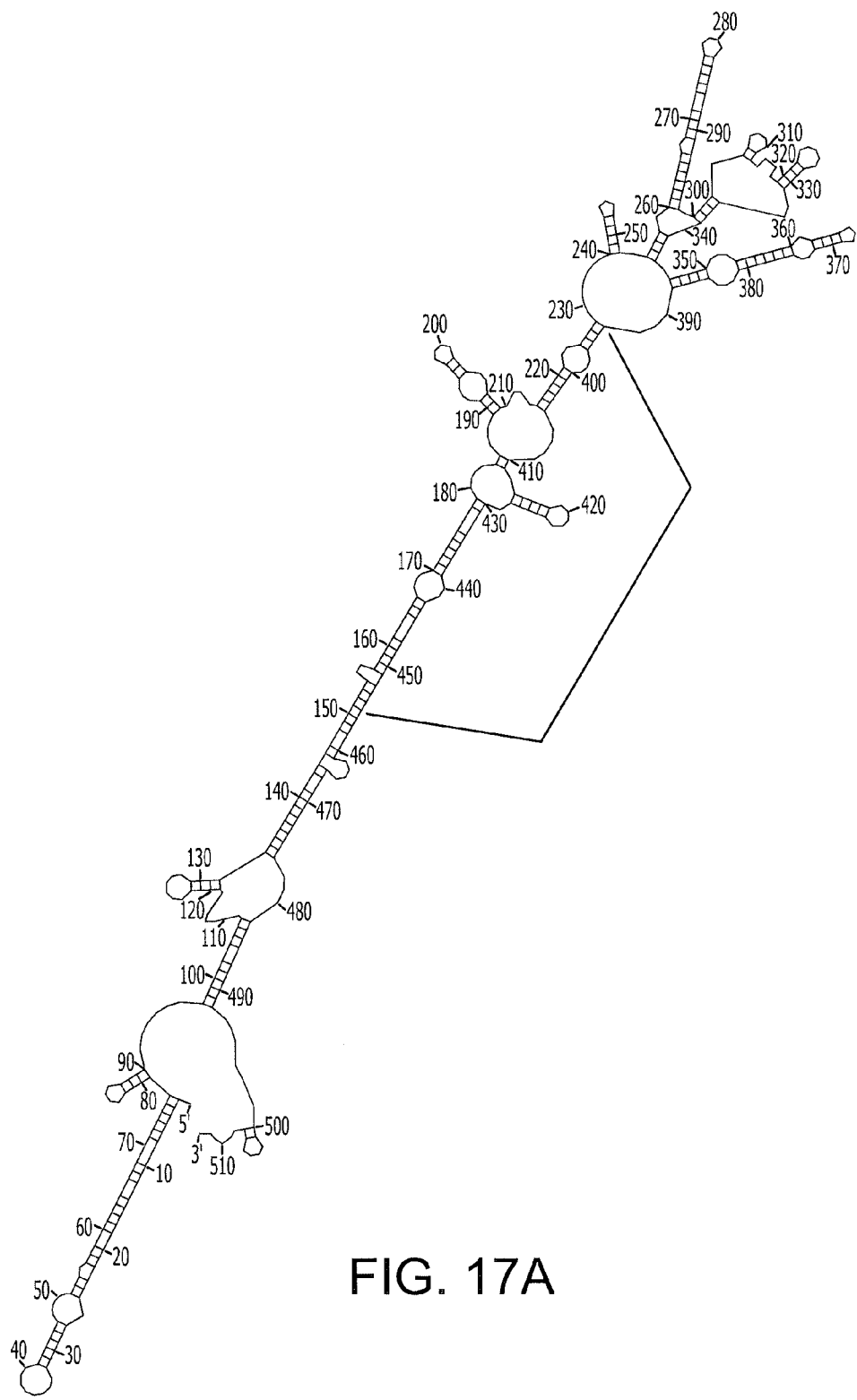
FIGS. 17A and 17B comprise a schematic depiction of the Mfold-predicted RNA secondary structure of the SSAT coding region RNA (FIG. 17A) and an enlarged image of the secondary structure predicted for nucleotides 151-453 (FIG. 17B). The bracket in FIG. 17A identifies the region depicted in FIG. 17B, which includes nucleotides 151-227 and 393-454 of SEQ ID No. 69. Arrows 1 and 2 indicate nucleotides 400 and 453, respectively. The bracket in FIG. 17B indicates the step loop in nucleotides 414-428.
Figure 17B:
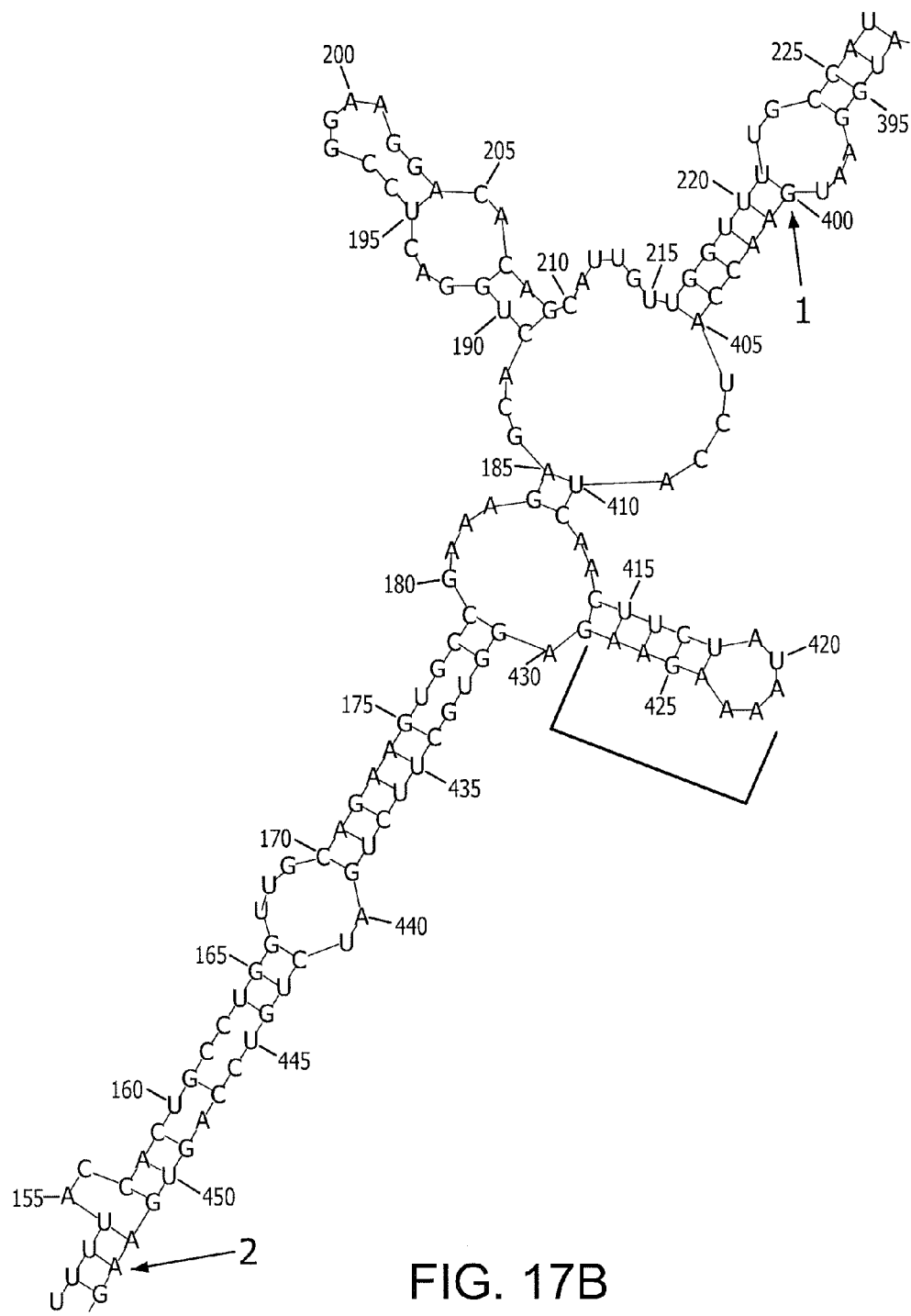

Mfold software was used to predict the secondary structure of the entire SSAT ORF. The region between nucleotides 400-453 contained a stem loop consisting of nucleotides 414-428 (FIG. 17).

Figure 19A:
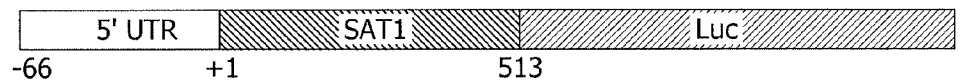
FIGS. 19A, 19B and 19C comprise a schematic structure of a chimeric construct for assaying translation repression and two bar graphs of translation data.

To test the possible contribution of this stem loop to the activation of translation of SSAT mRNA, a series of silent mutations were made to nucleotides in this region. The silent mutations changed the predicted RNA secondary structure but do not change the encoded primary amino acid sequence. Ten mutant chimeric constructs were prepared using appropriate reverse primers containing the desired mutation and a common forward primer, and conventional PCT methods. The integrity of each of the mutants prepared was confirmed by sequencing. Each mutant has one or two silent mutations. The chimeric construct comprised the 66 nucleotides of the 5'UTR, nucleotides 1-513 encoding SSAT linked in-frame with the coding sequence for luciferase (FIG. 19A).

Figure 18A:
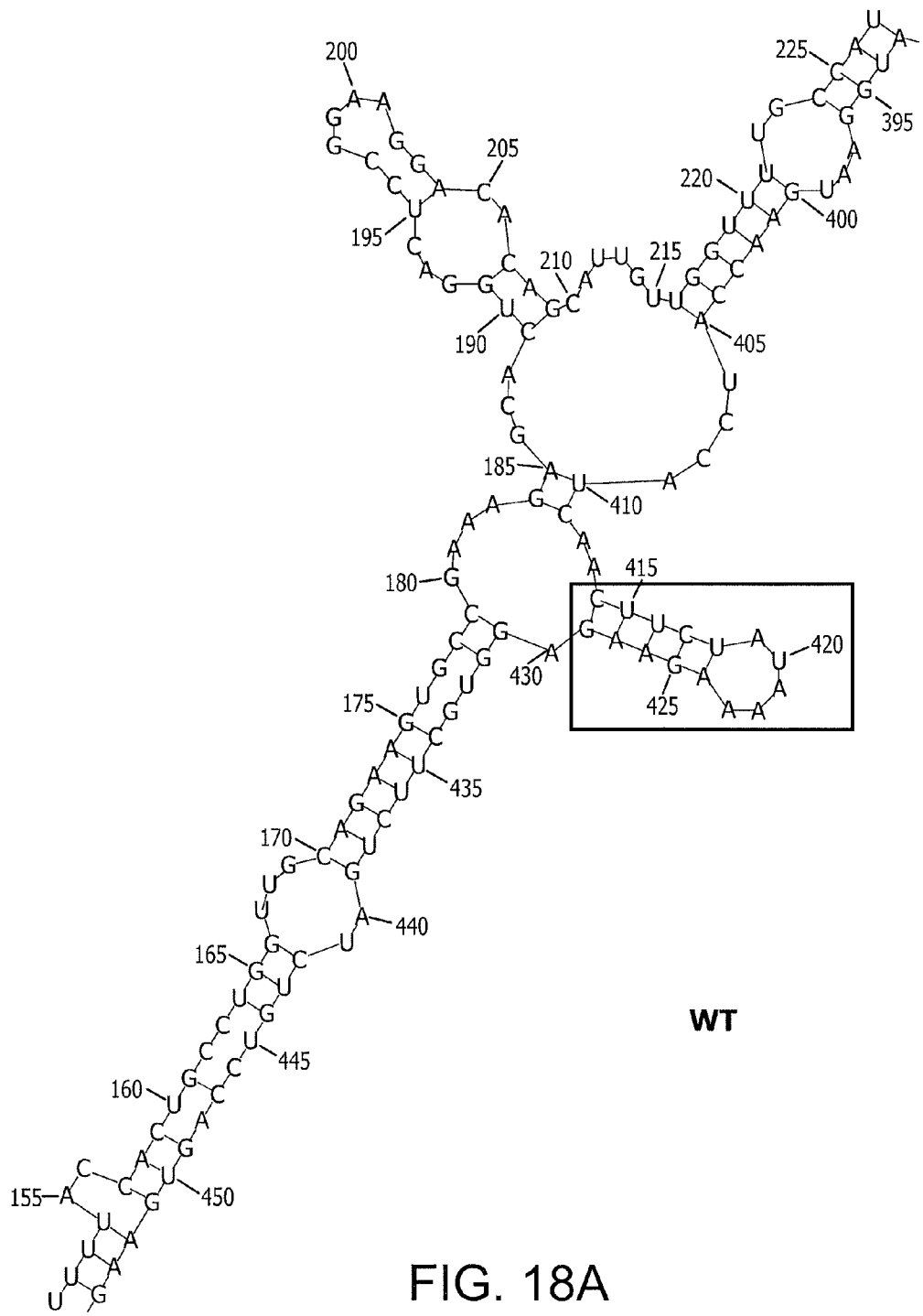
FIGS. 18A-18N depict schematically the RNA secondary structure predicted by Mfold software for various mutants of the SSAT ORF. In some of FIGS. 18A-18N, segments of the sequence are not depicted.

The predicted secondary structure of the wild-type SSAT mRNA sequence is shown in FIG. 18A. The predicted secondary structure for each mutant is shown in FIGS. 18B-18N. In each structure, nucleotides 414-428 are enclosed by a shape. Each mutation is designated by the wild-type nucleotide, the nucleotide number (with respect to SEQ ID NO. 16) and the mutated nucleotide in Table 8. For instance, the designation "C414T" indicates that the cytosine at nucleotide position 414 of SEQ ID NO. 16 is changed to a thymine. The table also lists the amino acid residue(s) whose codon comprises the mutated nucleotide. The amino acid encoded was not changed by any of the mutations.

TABLE 8

Figure 18B:
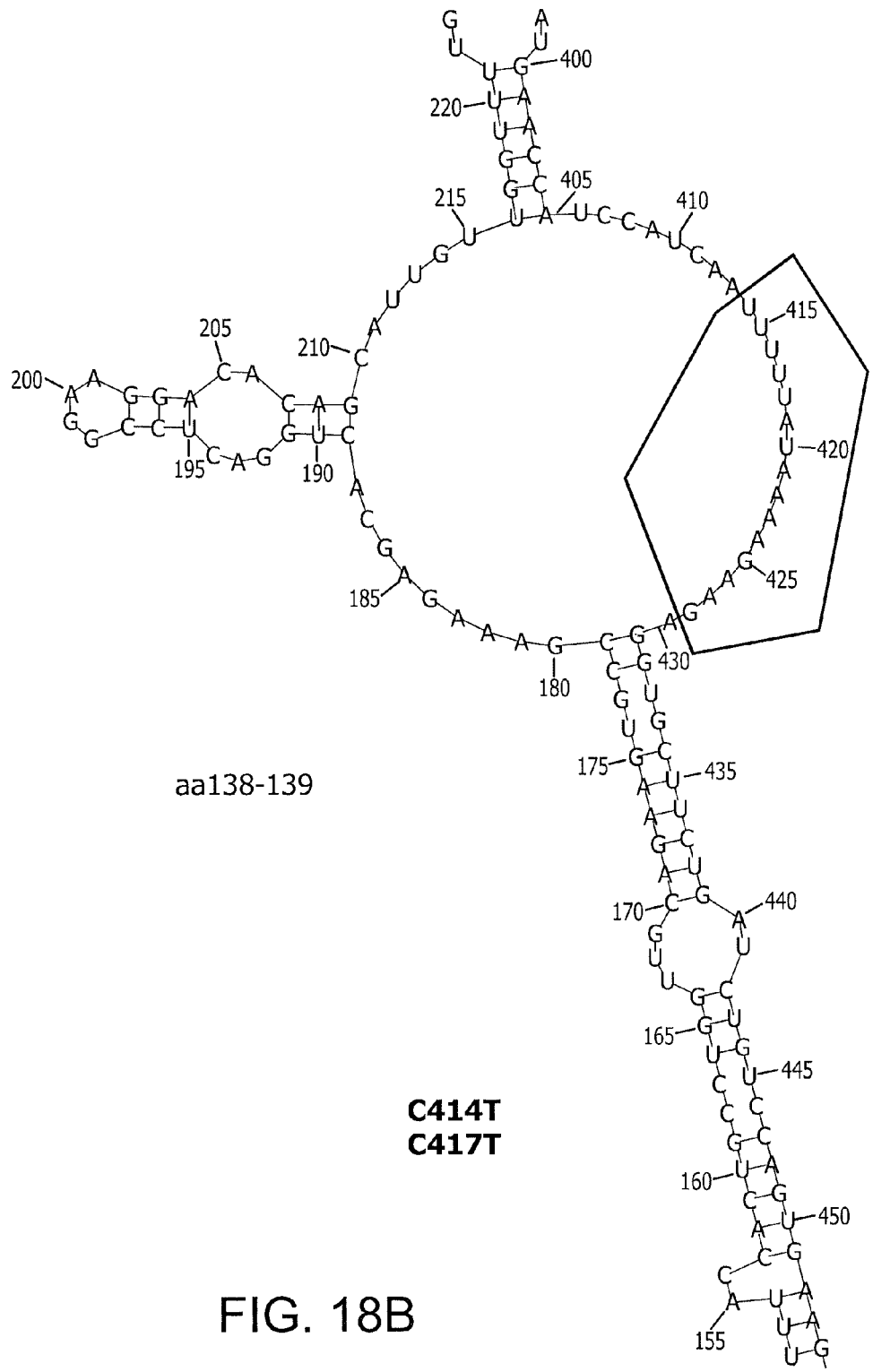
FIG. 18B is the predicted secondary structure for mutant 1 RNA, having the double mutation C414T and C417T. Nucleotides 152-223 and 398-454 of SEQ ID No. 69 are depicted, where nucleotide 414 is changed to T and nucleotide 417 is changed to T.
Figure 18C:
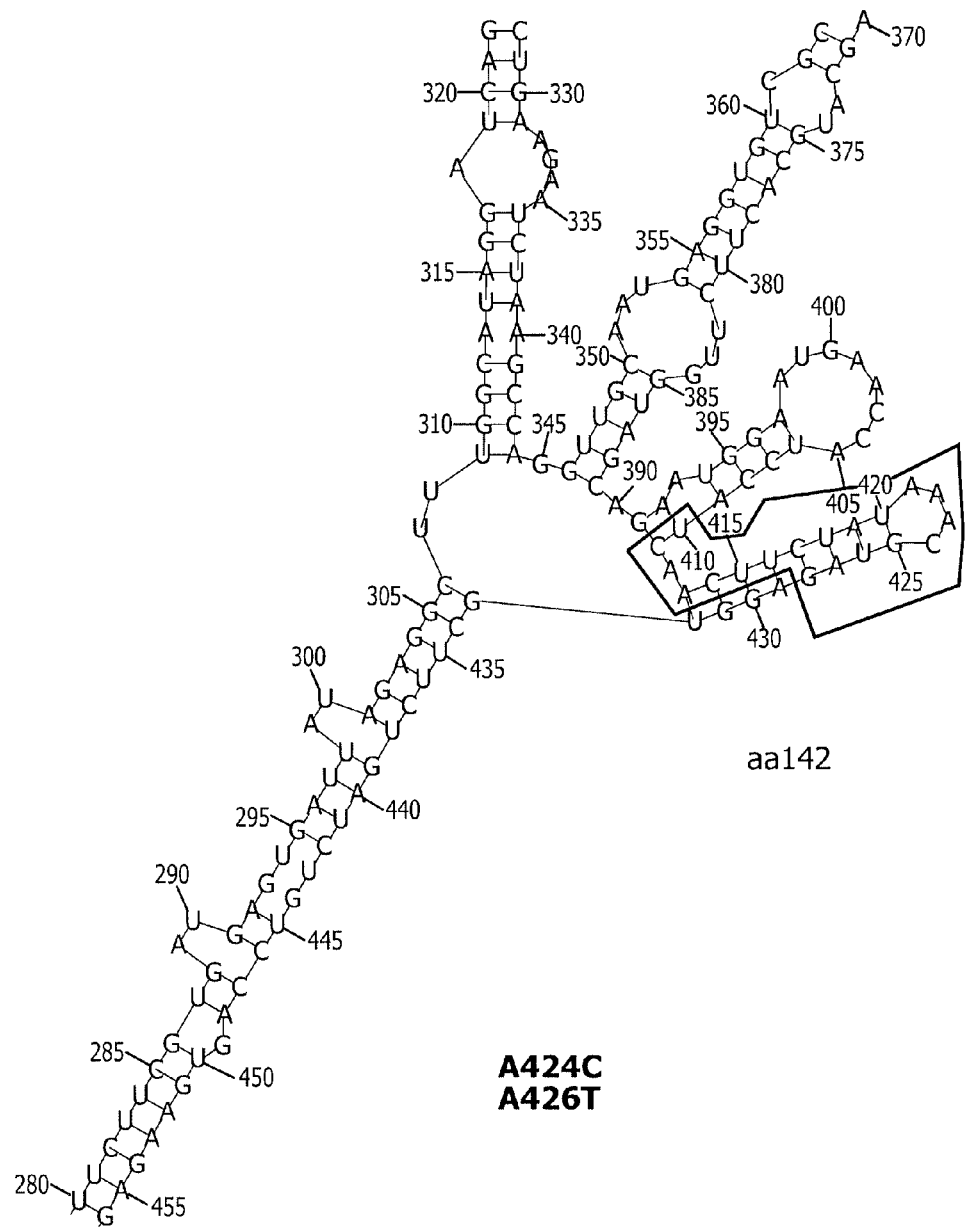
FIG. 18C is the predicted secondary structure for mutant 2 RNA, having the double mutation A424C and A426T. Nucleotides 280-322, 328-363, and 370-456 of SEQ ID No. 69 are depicted, where nucleotide 424 is changed to C and nucleotide 426 is changed to T.
Figure 18D:
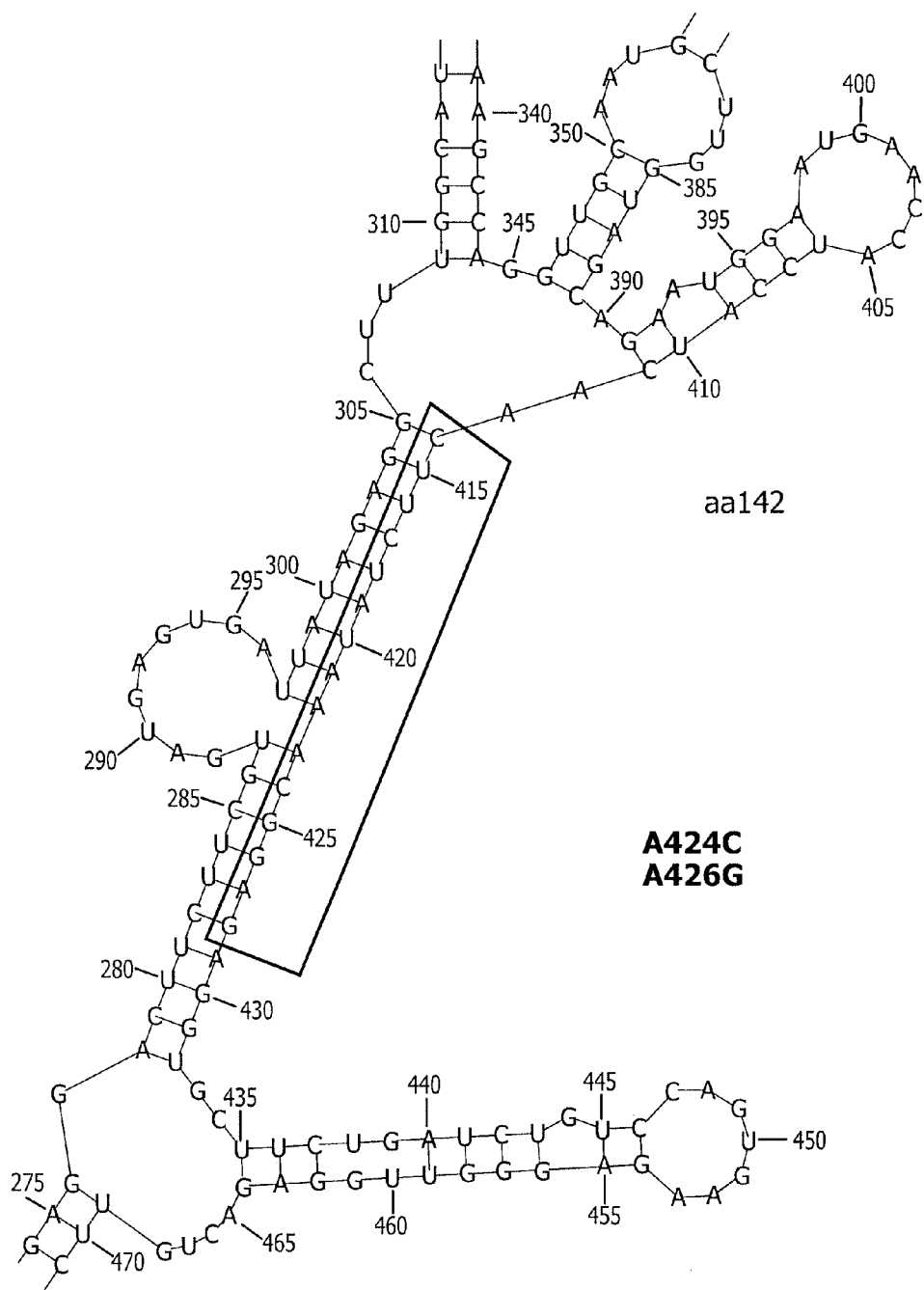
FIG. 18D is the predicted secondary structure for mutant 3 RNA, having the double mutation A424C and A426G. Nucleotides 274-314, 339-354, and 381-471 of SEQ ID No. 69 are depicted, where nucleotide 424 is changed to C and nucleotide 426 is changed to G.
Figure 18E:
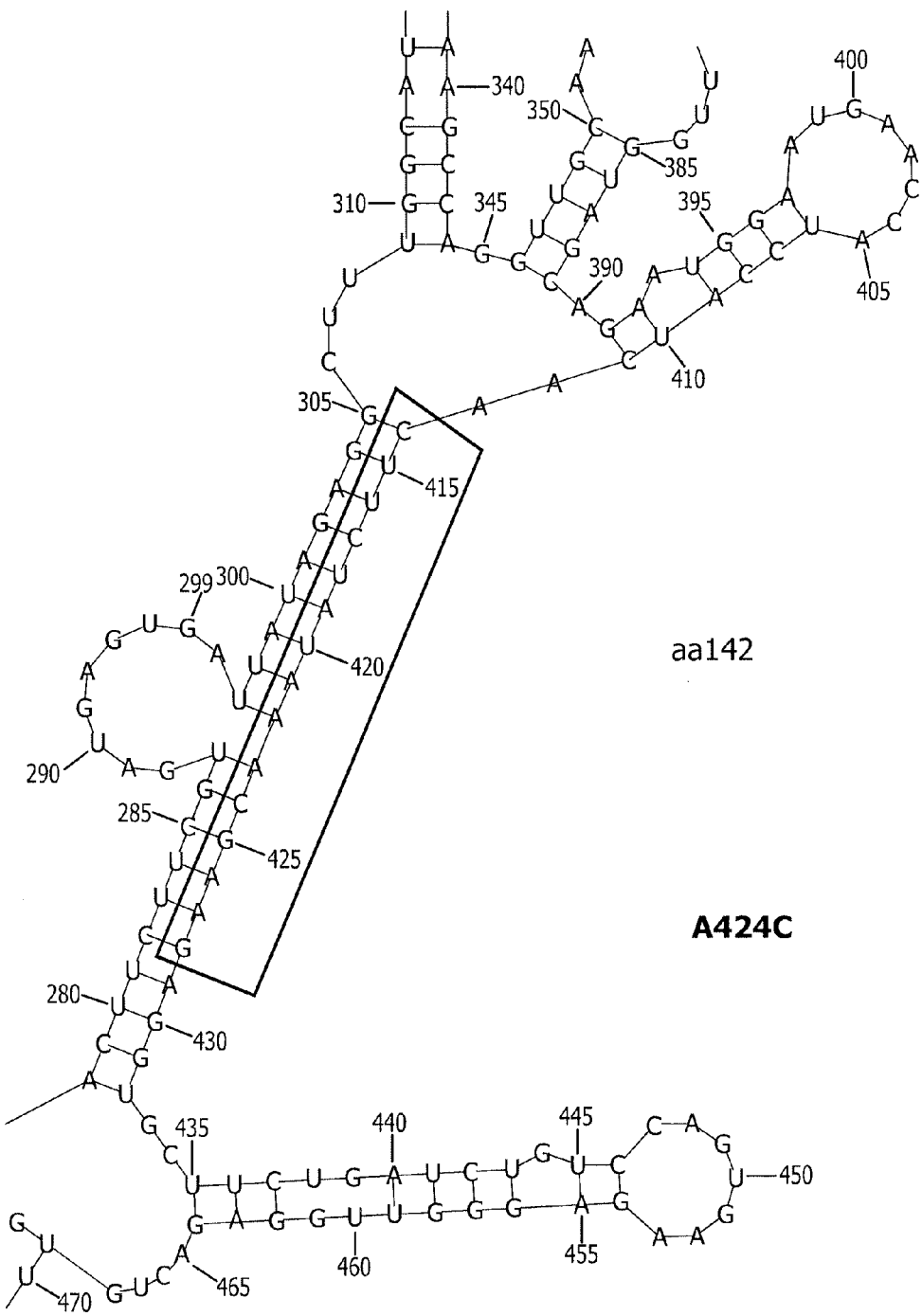
FIG. 18E is the predicted secondary structure for mutant 4 RNA, having the single mutation A424C. Nucleotides 278-314, 339-352, and 382-470 of SEQ ID No. 69 are depicted, where nucleotide 424 is changed to C.
Figure 18F:
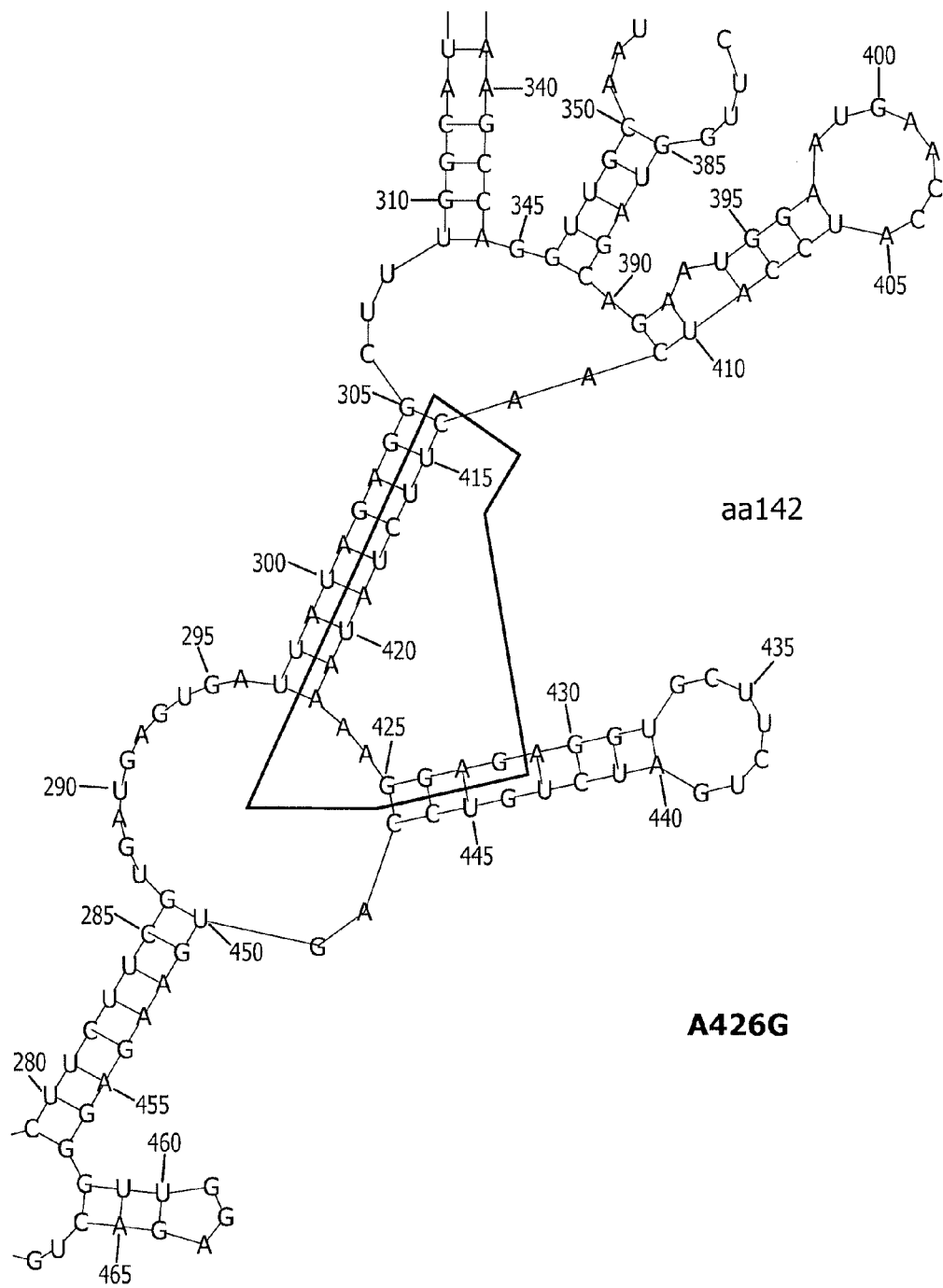
FIG. 18F is the predicted secondary structure for mutant 5 RNA, having the single mutation A426G. Nucleotides 279-314, 339-353, and 381-468 of SEQ ID No. 69 are depicted, where nucleotide 426 is changed to G.
Figure 18G:
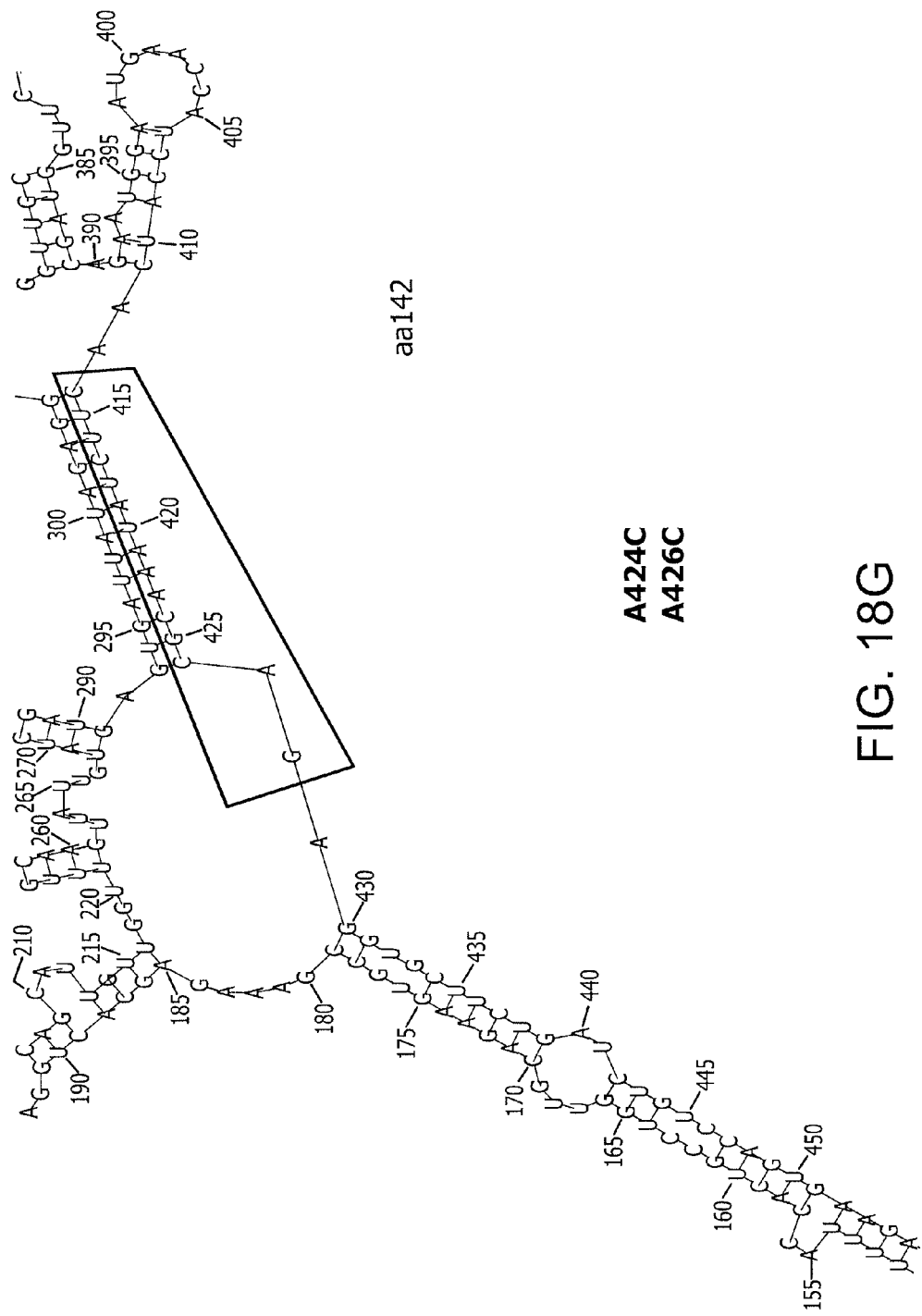
FIG. 18G is the predicted secondary structure for mutant 6 RNA, having the double mutation A424C and A426C. Nucleotides 151-193, 207-224, 258-271, 288-305, 345-350, and 382-453 of SEQ ID No. 69 are depicted, where nucleotide 424 is changed to C and nucleotide 426 is changed to C.
Figure 18H:
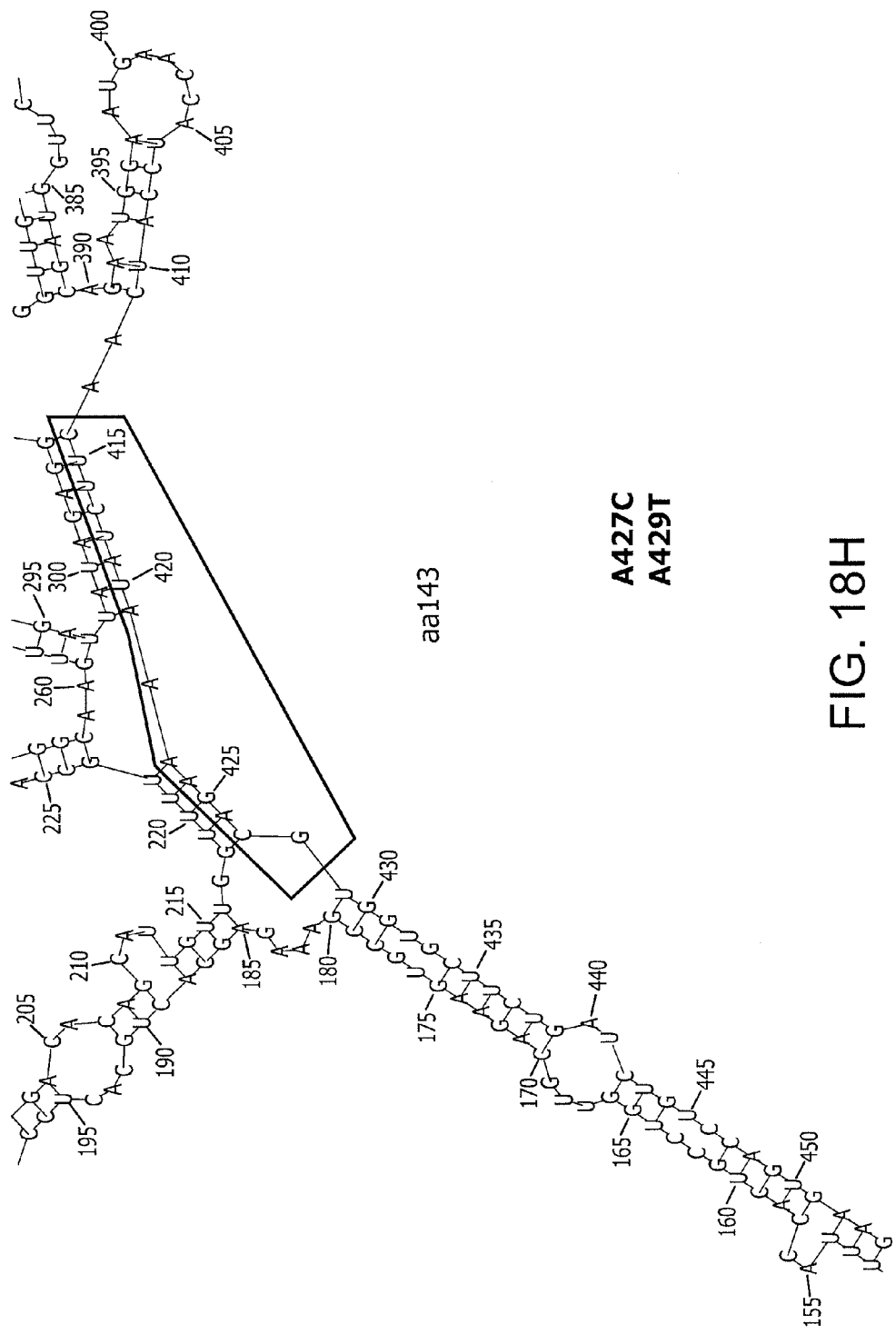
FIG. 18H is the predicted secondary structure for mutant 7 RNA, having the double mutation A427C and A429T. Nucleotides 152-197, 203-226, 256-263, 295-305, 345-349, and 381-454 of SEQ ID No. 69 are depicted, where nucleotide 427 is changed to C and nucleotide 429 is changed to T.
Figure 18I:
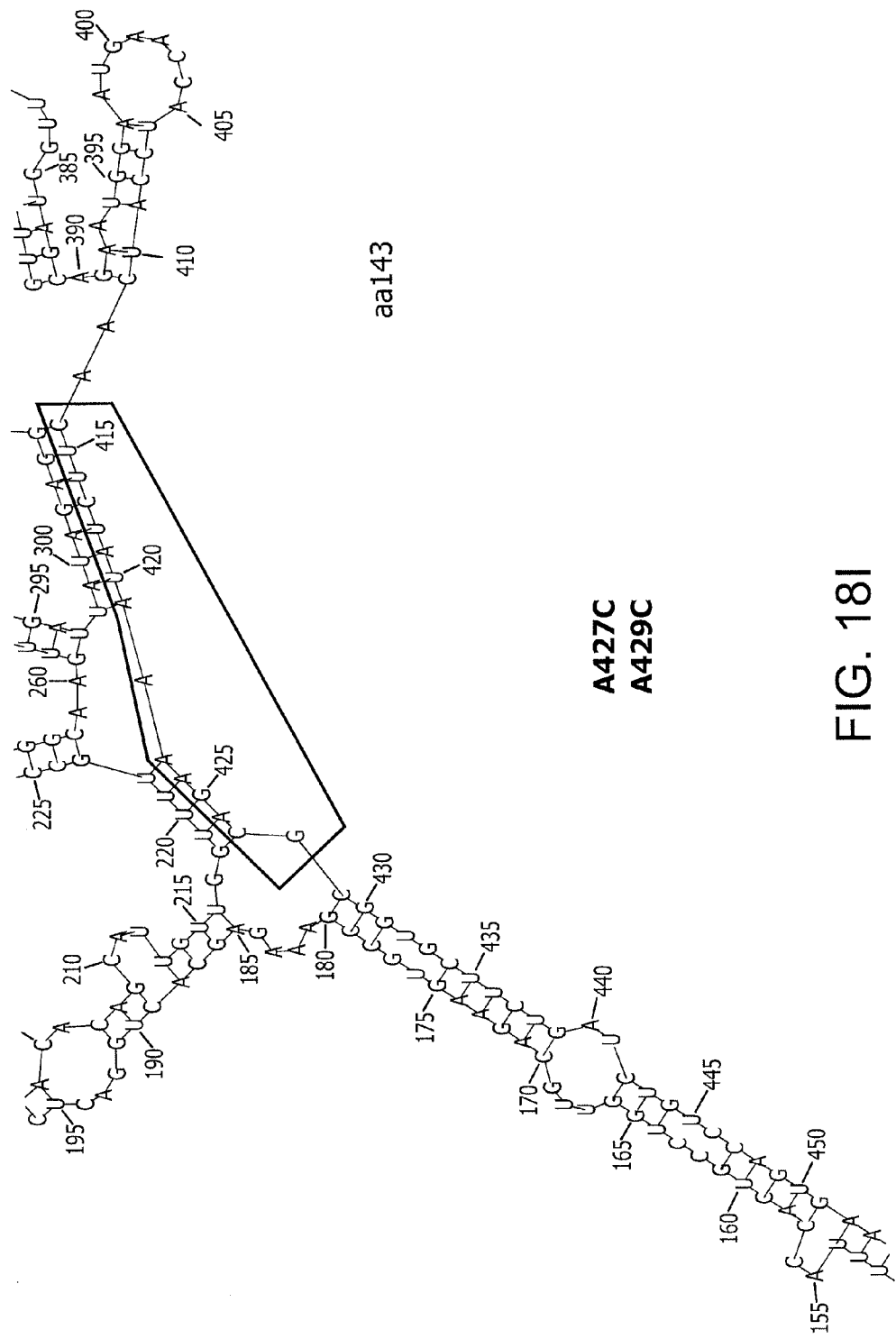
FIG. 18I is the predicted secondary structure for mutant 8 RNA, having the double mutation A427C and A429C. Nucleotides 152-196, 204-225, 256-263, 295-305, 346-348, and 382-453 of SEQ ID No. 69 are depicted, where nucleotide 427 is changed to C and nucleotide 429 is changed to C.
Figure 18J:
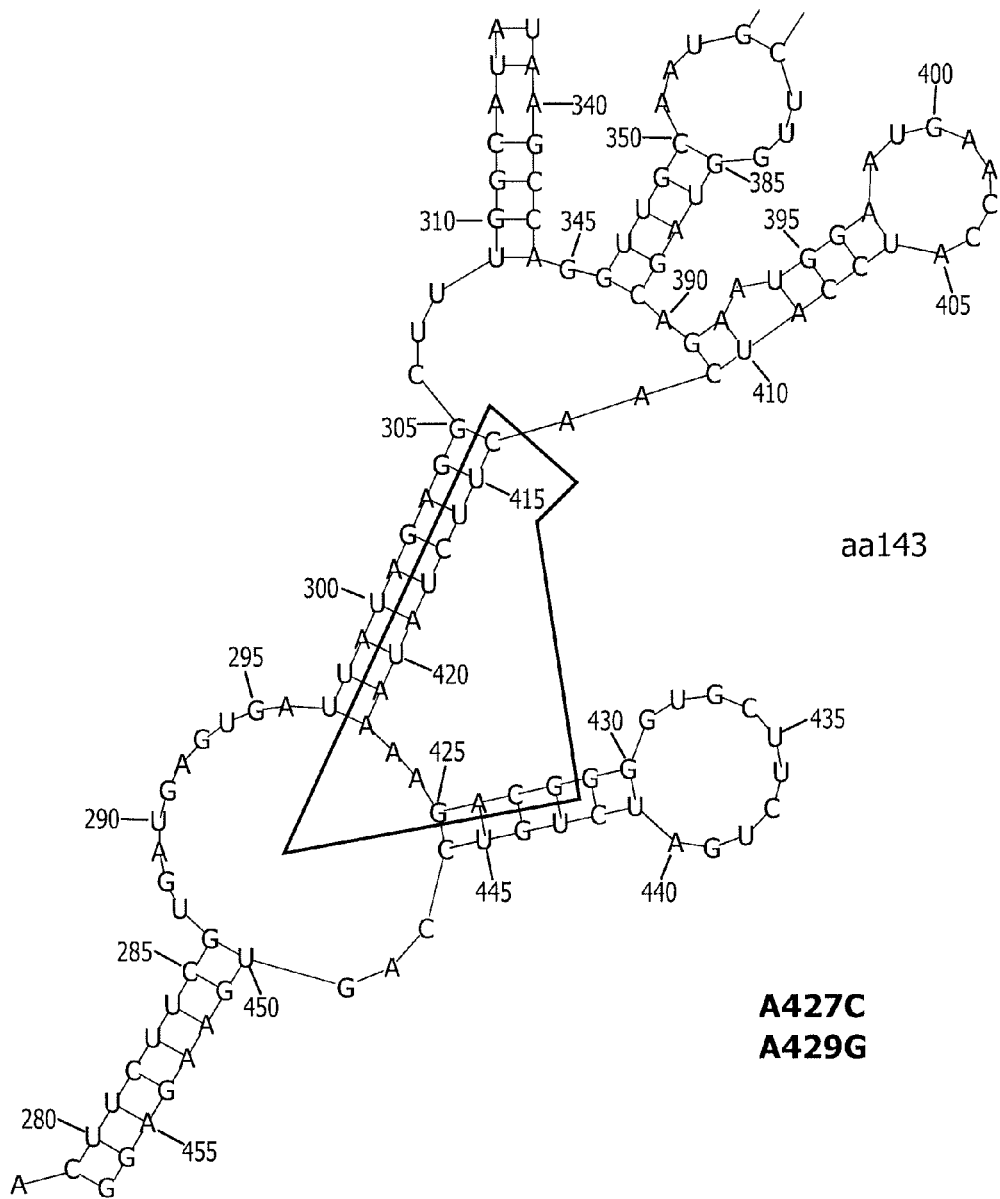
FIG. 18J is the predicted secondary structure for mutant 9 RNA, having the double mutation A427C and A429G. Nucleotides 278-315, 338-354, and 381-457 of SEQ ID No. 69 are depicted, where nucleotide 427 is changed to C and nucleotide 429 is changed to G.
Figure 18K:
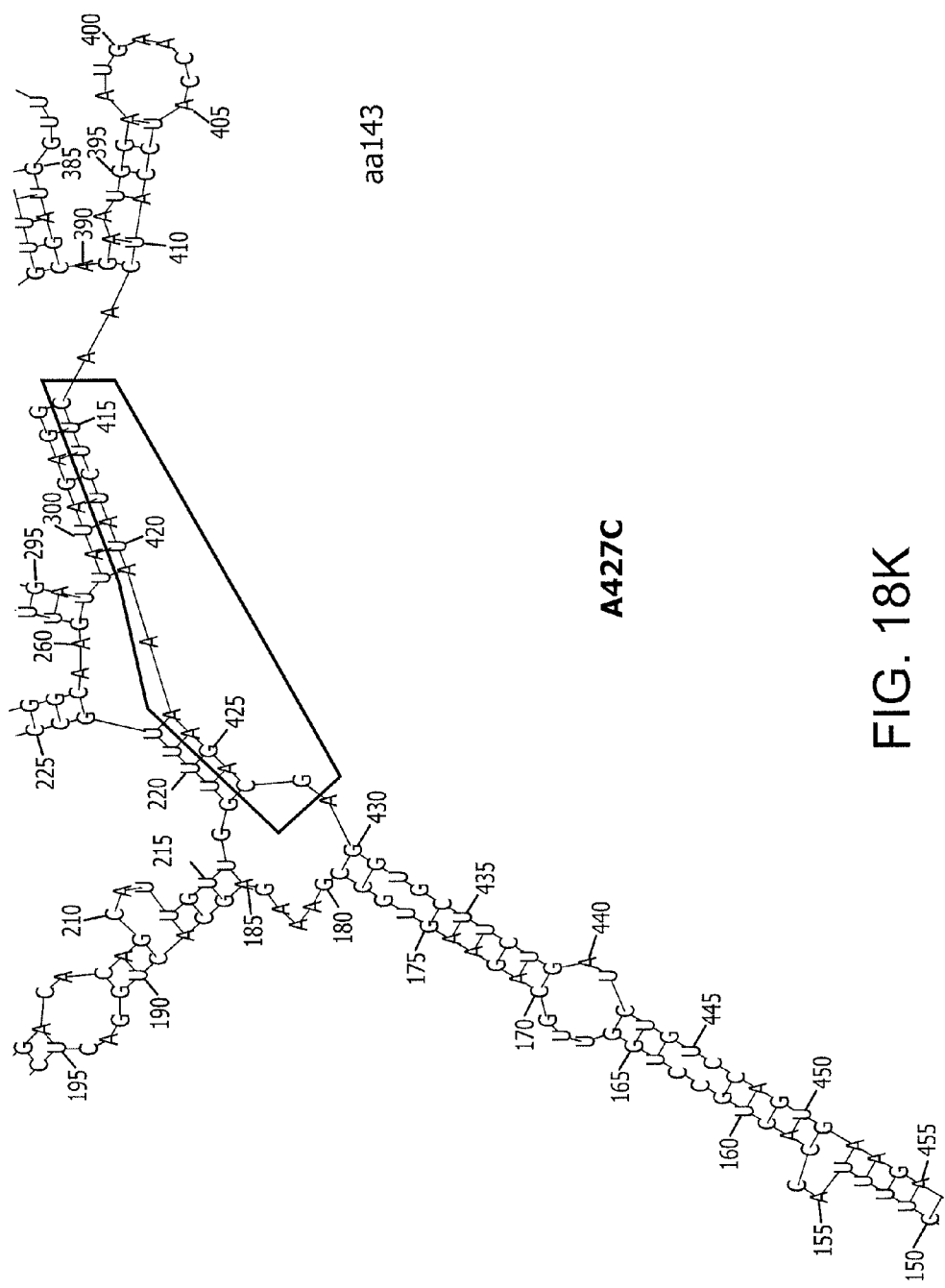
FIG. 18K is the predicted secondary structure for mutant 10 RNA, having the single mutation A427C. Nucleotides 150-196, 203-225, 256-263, 295-305, 346-348, and 382-455 of SEQ ID No. 69 are depicted, where nucleotide 427 is changed to C.

| Mutant | Mutation(s) | Amino acid(s) encoded | Predicted structure |
|---|---|---|---|
| 1 | C414T, C417T | 138 and 139 | FIG. 18B |
| 2 | A424C, A426T | 142 | FIG. 18C |
| 3 | A424C, A426G | 142 | FIG. 18D |
| 4 | A424C | 142 | FIG. 18E |
| 5 | A426G | 142 | FIG. 18F |
| 6 | A424C, A426C | 142 | FIG. 18G |
| 7 | A427C, A429T | 143 | FIG. 18H |
| 8 | A427C, A429C | 142 | FIG. 18I |
| 9 | A427C, A429G | 143 | FIG. 18J |
| 10 | A427C | 142 | FIG. 18K |

Three additional chimeric mutant constructs were prepared (Table 9). These mutants contained silent mutations distant from the stem loop in nucleotides 414-428 that were also predicted to change the secondary structure at nucleotides 414-428.

TABLE 9

Figure 18L:
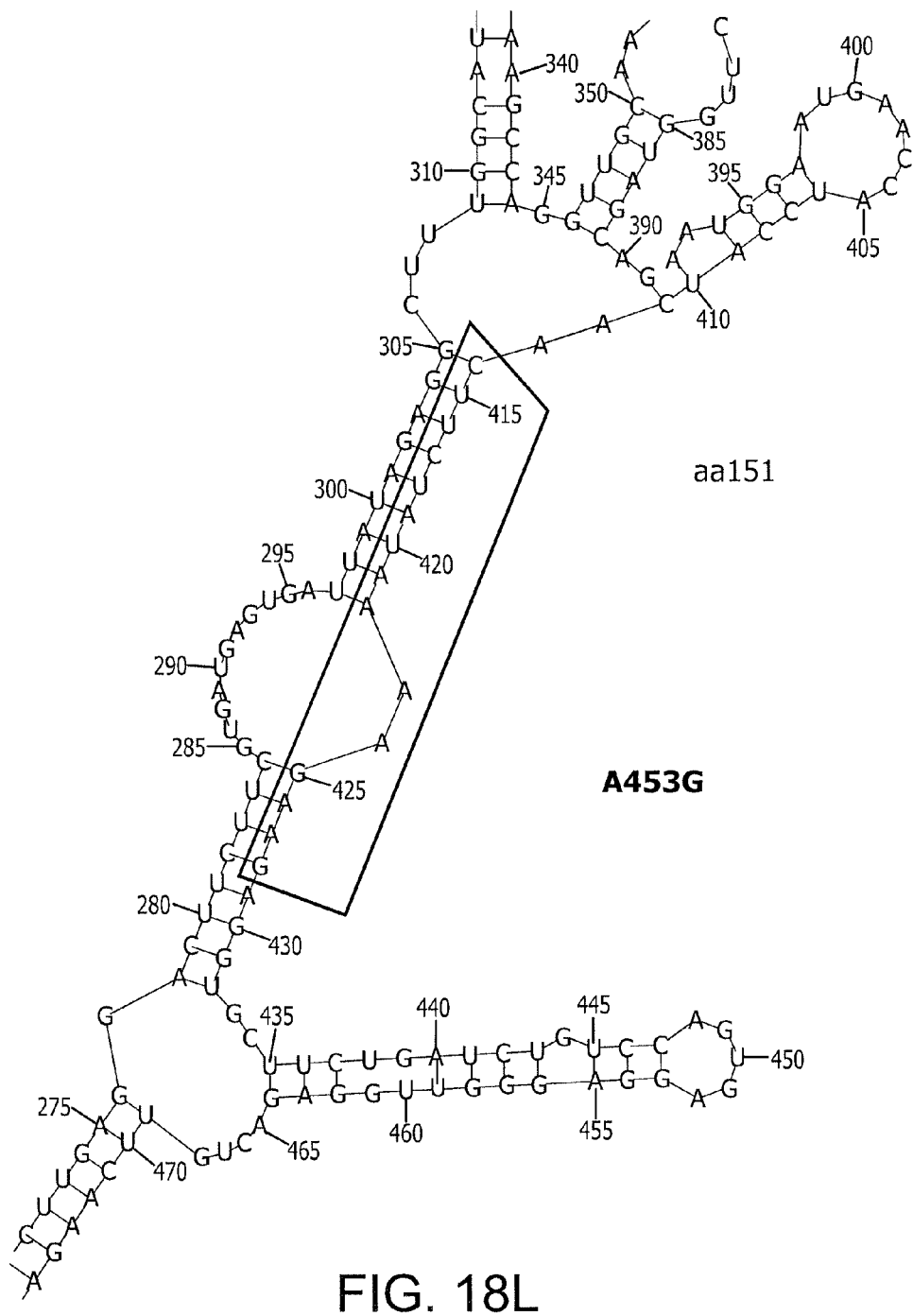
FIG. 18L is the predicted secondary structure for mutant 11 RNA, having the single mutation A453G. Nucleotides 271-314, 339-352, and 381-475 of SEQ ID No. 69 are depicted, where nucleotide 453 is changed to G.
Figure 18M:
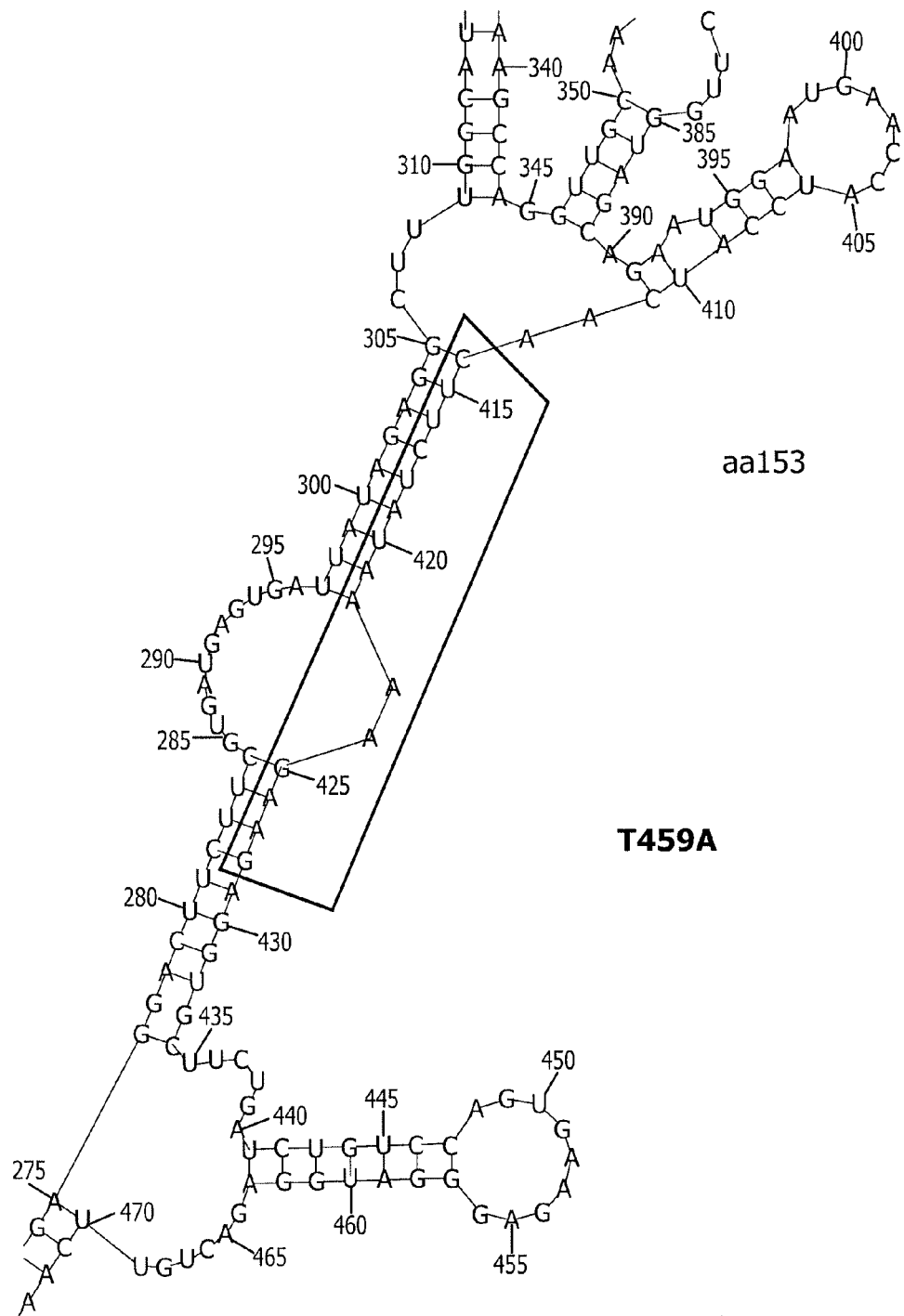
FIG. 18M is the predicted secondary structure for mutant 12 RNA, having the single mutation T459A. Nucleotides 274-314, 339-352, and 381-473 of SEQ ID No. 69 are depicted, where nucleotide 459 is changed to A.
Figure 18N:
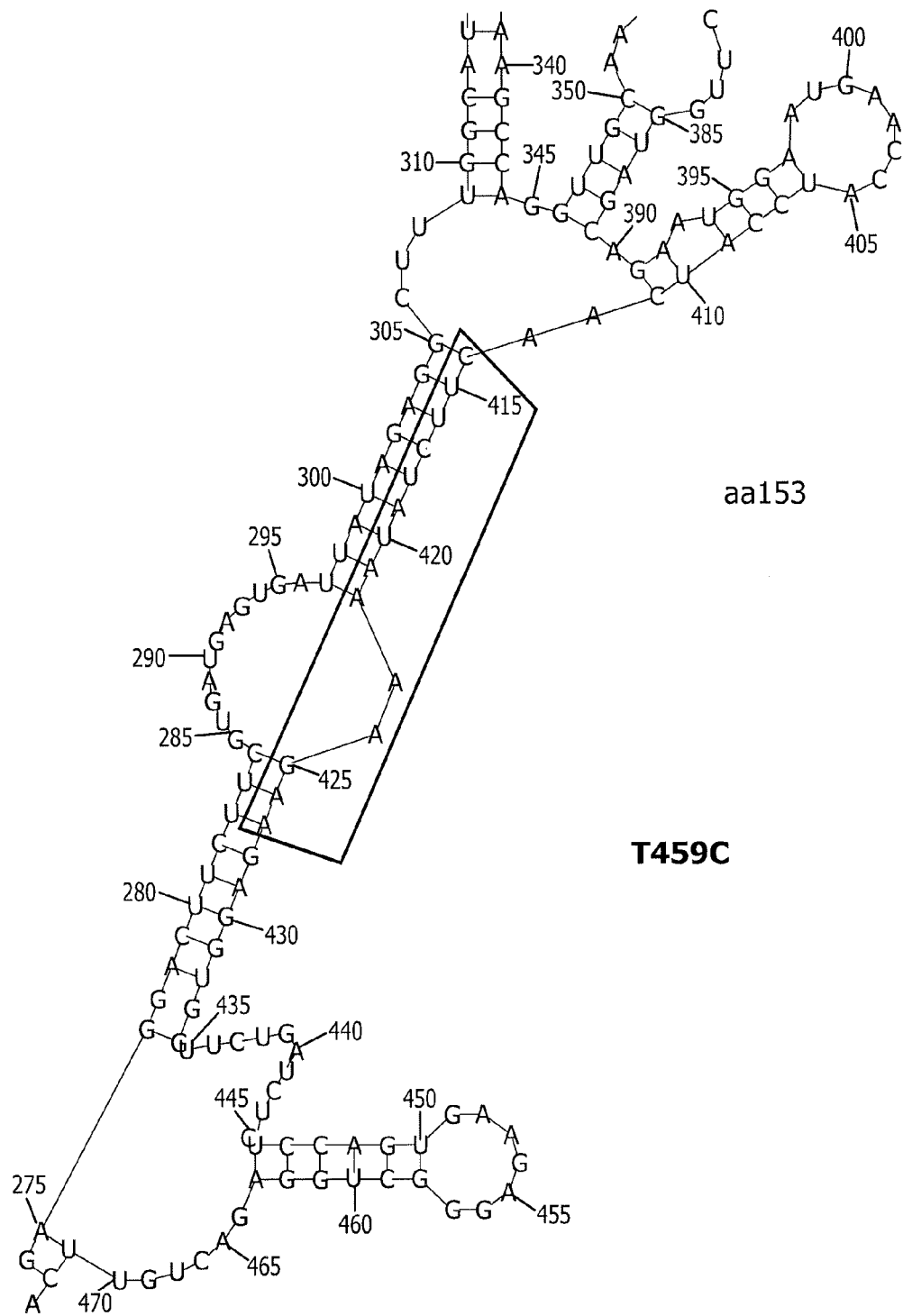

| Mutant | Mutation | Amino acid encoded | Predicted structure |
|---|---|---|---|
| 11 | A453G | 151 | FIG. 18L |
| 12 | T459A | 153 | FIG. 18M |
| 13 | T459C | 153 | FIG. 18N |

Figure 19B:
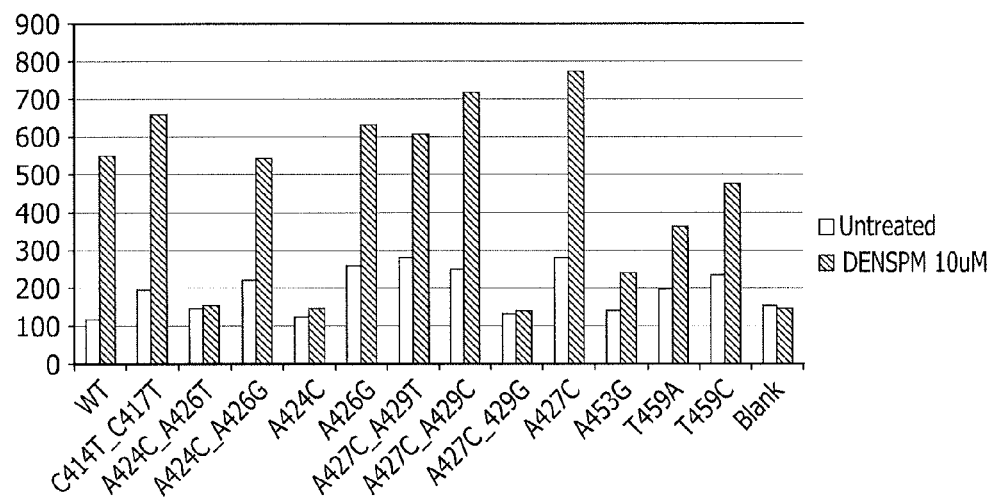
Figure 19C:
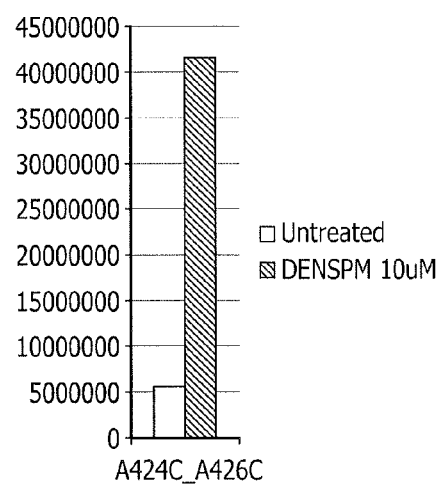

The thirteen chimeric constructs were tested for their capacity to respond to DENSPM stimulation of translation. Specifically, translation of the thirteen chimeric constructs was tested in the absence and presence of DENSPM and measured by detection of luciferase activity. The luciferase data for twelve of the thirteen constructs (mutants 1-5 and 7-13) are depicted in FIG. 19B. The data for mutant 6 are depicted in FIG. 19C.

Mutants 1, 3, 5, 7, 8, and 10 show substantially the same extent of translation stimulation in response to DENSPM as the wild type construct. For mutants 11, 12 and 13, the mutation rendered the chimeric construct less responsive to translation stimulation by DENSPM, when compared to the wild type construct. For mutants 2, 4 and 9, the mutation rendered the chimeric construct non-responsive to translation stimulation by DENSPM.

Mutant 6 was markedly different from all other mutants prepared. The order of magnitude increase in translation by mutant 6, compared to wild type and the other mutants, necessitated plotting the data in a different graph (compare scale of y-axis in FIG. 19C to scale in FIG. 19B). Specifically, in the absence of DENSPM, the mutant construct exhibited a substantially greater degree of SSAT translation compared to the wild-type construct. This result indicates that the double mutation of mutant 6 relieves partially translational repression in the absence of polyamine stimulation. Remarkably, mutant 6 also exhibited a dramatic increase in translation in response to DENSPM stimulation.

These data indicate that the stem-loop structure between nucleotides 414-428 in the wild-type mRNA does not contribute to translation repression. Moreover, these data suggest that the dramatic improvement in dynamic range of mutant 6 (A424C, A426C) is not structure dependent. These data are consistent therefore with the conclusion that the change in dynamic range observed for mutant 6 is sequence-specific.

Example 5

Reporter System with Improved Dynamic Range to Detect Pharmacophores

A dose response experiment was performed using the mutant 6 chimeric construct. Specifically, the stimulation of mutant 6 translation by ten different concentrations of DENSPM was assayed. The DENSPM concentrations ranged from 0.08 micromolar (µM) to 40 µM. The dose response curve is depicted in FIG. 20.

Figure 20:
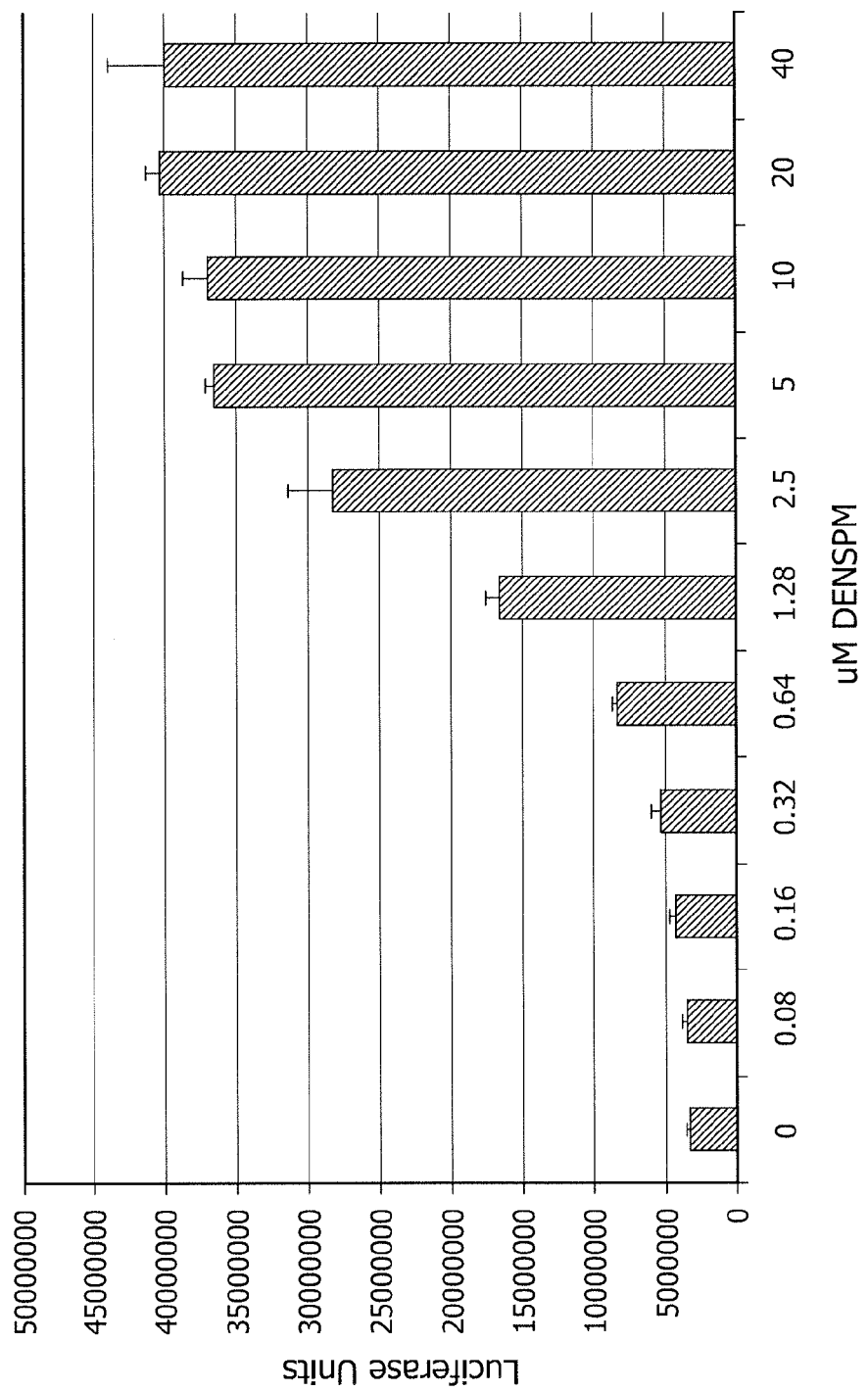
FIG. 20 is a response curve for mutant 6 over a range of DENSPM doses.

FIG. 20 demonstrates the dose response of mutant 6 construct over two orders of magnitude. The improved dynamic range of the mutant 6 chimeric construct and its dose response curve indicate that this mutant is highly suitable as a reporter construct for identifying candidate agents for efficacy in relieving translational repression of SSAT mRNA.

Example 6

Drug Screening with Reporter System and Identification of Compounds Inhibiting SSAT Translation The mutant 6 chimeric construct of Example 4 (A424C; A426C; FIG. 18G) cloned into pLEX MCS plasmid was utilized in drug screening as follows. HEK 293T cells (ATCC) were grown in DMEM supplemented with 10% fetal bovine serum and antibiotics. The HEK 293T cells were transfected with the mutant 6/pLEX MCS plasmid using HTS-Jetpei transfection reagent (Polyplus Transfection, Illkirch, France). Transfected HEK293T cells were incubated overnight at 37° C. After 24 hours, cells transfected cells in 96-well plates used for screening were treated with 10 µM of test compound from a compound library in DMSO. Untreated cells were used as the negative control, and cells treated with 10 µM DENSPM comprised a positive control. The luciferase signaling in each plate was independently analyzed using a Glomax Luminometer (Promega Corp.) by comparing the signals against the controls twelve hours after treatment.

Table 10 contains the screening results for eighteen compounds displaying 85% or greater inhibition of SSAT translation.

TABLE 10

| Compound | % Inhibition SSAT Translation | Systematic name | Structure |
| --- | --- | --- | --- |
| Astemizole | 86.22 | 1-[(4-fluorophenyl)methyl]-N-[1-[2-(4-methoxyphenyl)ethyl]-4-piperidyl]benzoimidazol-2-amine | 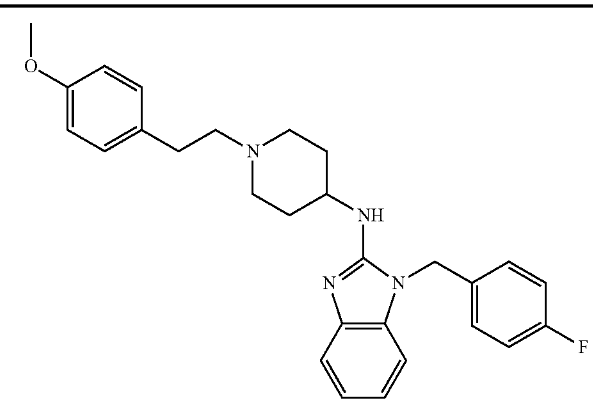 |
| Terfenadine | 99.97 | (RS)-1-(4-tert-butylphenyl)-4-{4-[hydroxy(diphenyl)methyl]piperidin-1-yl}-butan-1-ol | 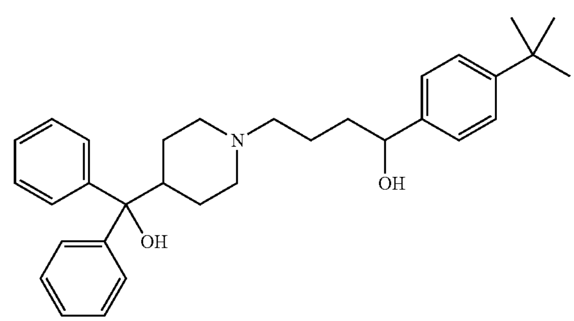 [SMILES: CC(C)(C)c1ccc(C(O)CCCN2CCC(C(O)(c3ccccc3)c3ccccc3)CC2)cc1] |

TABLE 10-continued

| Compound | % Inhibition SSAT Translation | Systematic name | Structure |
|---|---|---|---|
| Vanoxerine dihydrochloride | 96.91 | 1-[2-[bis(4-fluorophenyl)methoxy]ethyl]-4-(3-phenylpropyl)piperazine•(HCl)$_2$ | 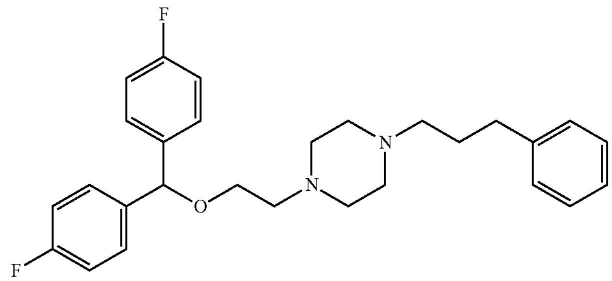 |
| Suloctidil | 99.91 | (R*,S*)-4-((1-methylethyl)thio)-alpha-(1-(octylamino)ethyl)benzene-methanol | 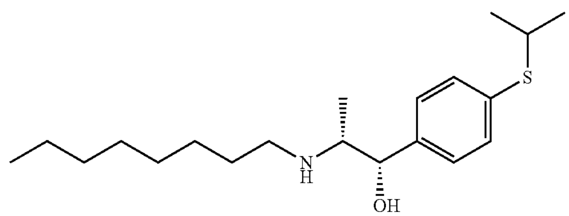 [SMILES: CCCCCCCCN[C@H](C)[C@@H](O)c1ccc(SC(C)C)cc1] |
| Digitoxigenin | 93.40 | 3-β,14-dihydroxy-5-β,14-β-card-20(22)-enolide | 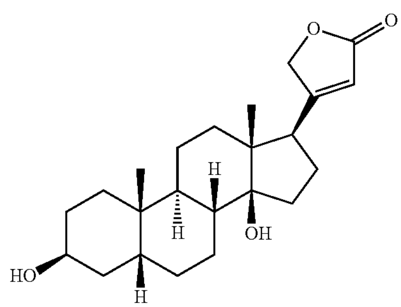 |
| Digoxin | 93.89 | 4-[(3S,5R,8R,9S,10S,12R,13S,14S)-3-[(2S,4S,5R,6R)-5-[(2S,4S,5R,6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10,13-dimethyl-1,2,3,4,5,6,7,8,9,11,12,15,16,17-tetradecahydrocyclopenta[a]phenanthren-17-yl]-5H-furan-2-one | 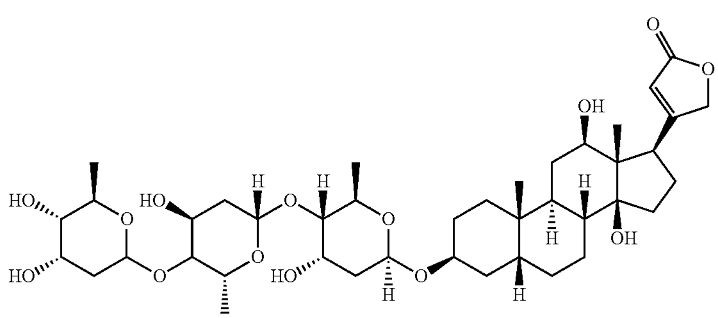 |
| Parthenolide | 99.23 | (1aR,7aS,10aS,10bS)-1a,5-dimethyl-8-methylene-2,3,6,7,7a,8,10a,10b-octahydrooxireno[9,10]cyclodeca[1,2-b]furan-9(1aH)-one | 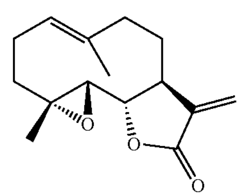 [SMILES: C=C1C(=O)O[C@H]2[C@H]1CC/C(C)=C/CC[C@@]1(C)O[C@@H]21] |

TABLE 10-continued

| Compound | % Inhibition SSAT Translation | Systematic name | Structure |
|---|---|---|---|
| Chrysene-1,4-quinone | 97.35 | chrysene-1,4-dione | 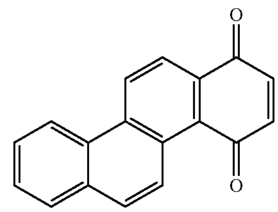 [SMILES: O=C1C=CC(=O)c2c1ccc1c2ccc2ccccc21] |
| Sertindole | 99.77 | 1-[2-[4-[5-chloro-1-(4-fluorophenyl)-indol-3-yl]-1-piperidyl]ethyl]-imidazolidin-2-one | 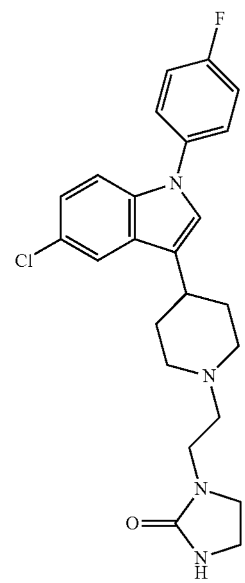 [SMILES: O=C1NCCN1CCN1CCC(c2cn(-c3ccc(F)cc3)c3ccc(Cl)cc23)CC1] |
| Lanatoside C | 91.83 | (3β,5β,12β)-3-{[β-D-glucopyranosyl-(1→4)-3-O-acetyl-2,6-dideoxy-β-D-ribo-hexopyranosyl-(1→4)-2,6-dideoxy-β-D-ribo-hexopyranosyl-(1→4)-2,6-dideoxy-β-D-ribo-hexopyranosyl]oxy}-12,14-dihydroxycard-20(22)-enolide | 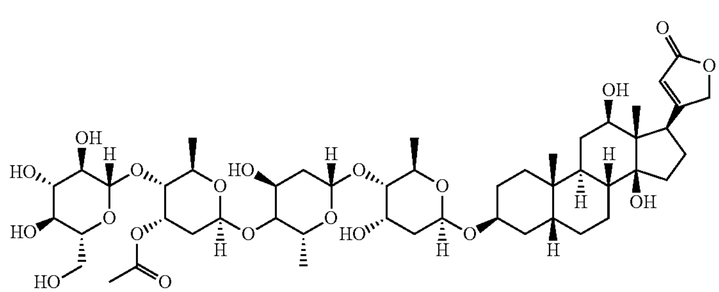 |

TABLE 10-continued

| Compound | % Inhibition SSAT Translation | Systematic name | Structure |
|---|---|---|---|
| Beta-Escin | 88.70 | (3α,5β,14β,16α,21α,22α)-22-acetoxy-16,23,28-trihydroxy-1-{[(2Z)-2-methylbut-2-enoyl]oxy}olean-12-en-3-yl-α-D-gulopyranosyl-(1→2)-[a-L-mannopyranosyl-(1→4)]-β-D-allopyranosiduronic acid | 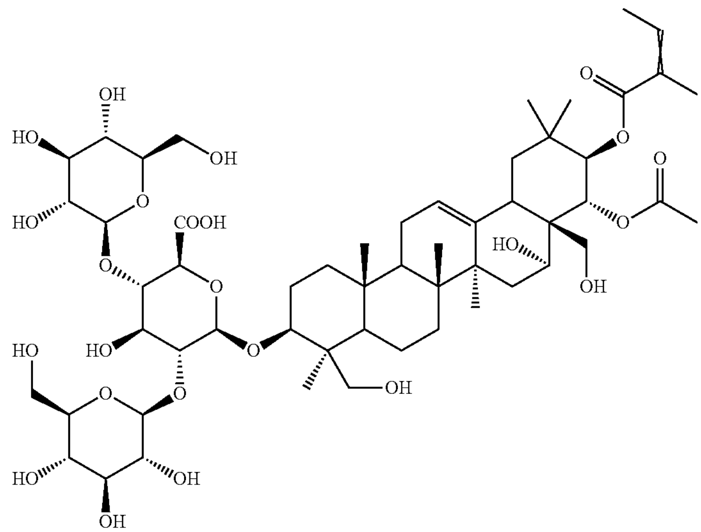 |
| Alexidine dihydrochloride | 99.63 | 1,1'-Hexamethylene-bis[5-(2-ethylhexyl)biguanide] dihydrochloride | 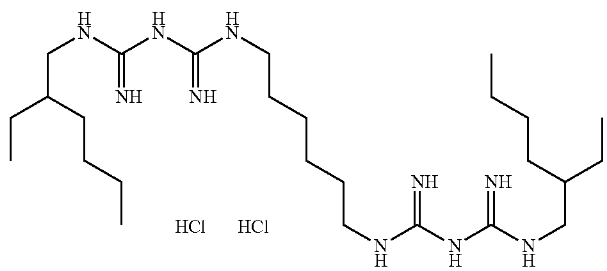 [SMILES: CCCCC(CC)CNC(=N)NC(=N)NCCCCCCNC(=N)NC(=N)NCC(CC)CCCC ; Cl ; Cl] |
| Fluspirilen | 94.68 | 8-[4,4-Bis(4-fluorphenyl)butyl]-1-phenyl-1,3,8-triazaspiro[4,5]decan-4-on | 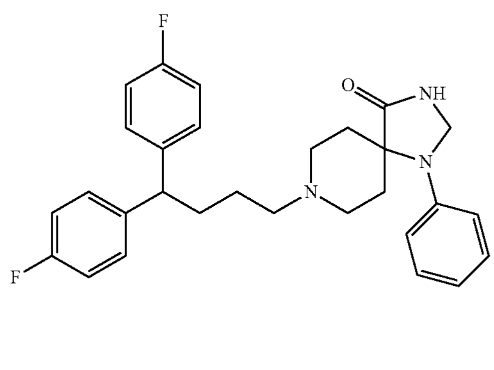 [SMILES: O=C1NCN(c2ccccc2)C12CCN(CCCC(c1ccc(F)cc1)c1ccc(F)cc1)CC2] |
| Thonzonium bromide | 99.00 | N-{2-[(4-Methoxybenzyl)(pyrimidin-2-yl)amino]ethyl}-N,N-dimethylhexadecan-1-aminium bromide | 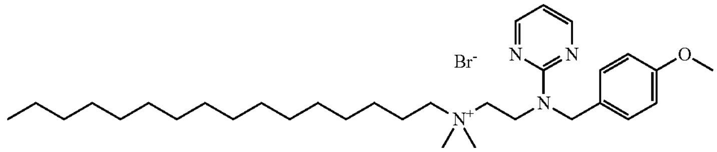 [SMILES: CCCCCCCCCCCCCCCC[N+](C)(C)CCN(Cc1ccc(OC)cc1)c1ncccn1 ; [Br-]] |

TABLE 10-continued

| Compound | % Inhibition SSAT Translation | Systematic name | Structure |
|---|---|---|---|
| Toremifene | 86.33 | 2-{4-[(1Z)-4-chloro-1,2-diphenyl-but-1-en-1-yl]phenoxy}-N,N-dimethylethanamine | 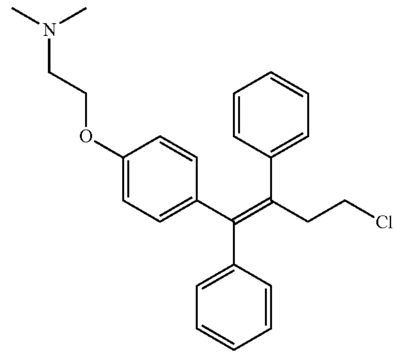 [SMILES: CN(C)CCOc1ccc(/C(=C(/CCCl)c2ccccc2)c2ccccc2)cc1] |
| Proscillaridin A | 93.97 | (3β)-3-[(6-deoxy-α-L-mannopyranosyl)oxy]-14-hydroxybufa-4,20,22-trienolide | |
| Pyrvinium pamoate | 92.48 | 2-[(E)-2-(2,5-dimethyl-1-phenylpyrrol-3-yl)ethenyl]-N,N,1-trimethylquinolin-1-ium-6-amine | 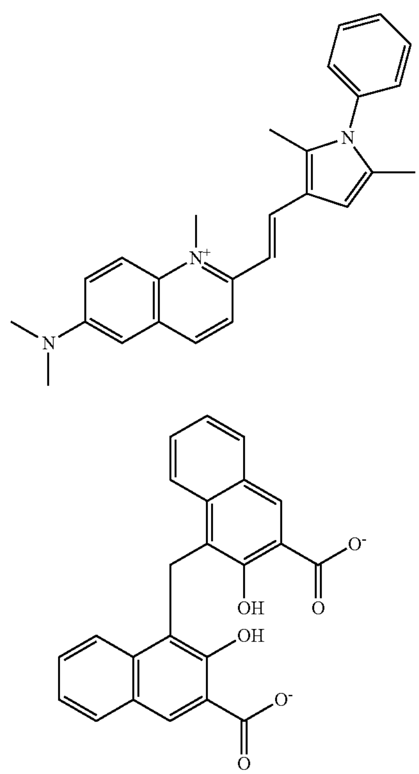 |

TABLE 10-continued

| Compound | % Inhibition SSAT Translation | Systematic name | Structure |
|---|---|---|---|
| Aripiprazole | 92.68 | 7-{4-[4-(2,3-dichlorophenyl)piperazin-1-yl]butoxy}-3,4-dihydroquinolin-2(1H)-one | 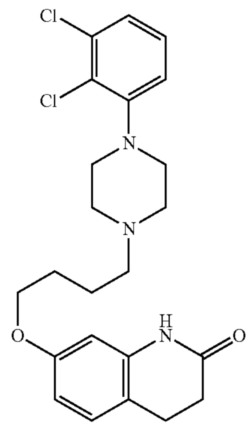 [SMILES: O=C1CCc2ccc(OCCCCN3CCN(c4cccc(Cl)c4Cl)CC3)cc2N1] |

Example 7

Identification of Compounds Increasing SSAT Translation

The procedure of Example 6 was followed, screening for compounds that increase SSAT translation. The agents listed in Table 11 were identified as increasing SSAT translation by at least 35% over basal SSAT translation.

TABLE 11

| Compound | % Increase in SSAT Translation |
|---|---|
| Pioglitazone | 50 |
| Tiabendazole | 39 |
| Pentamidine isethionate | 36 |
| Tetracaine hydrochloride | 40 |
| Tetraethylenepentamine pentahydrochloride | 60 |
| Phenazopyridine hydrochloride | 41 |
| Deflazacort | 37 |
| Equilin | 36 |
| Abacavir Sulfate | 36 |
| Nabumetone | 59 |
| Flucytosine | 35 |
| Doxylamine succinate | 62 |
| Antipyrine, 4-hydroxy | 41 |

The disclosures of each and every patent, patent application, and publication cited herein are hereby incorporated herein by reference in their entirety.

While the methods have been disclosed with reference to specific embodiments, it is apparent that other embodiments and variations may be devised by others skilled in the art without departing from the true spirit and scope of the described method. The appended claims are intended to be construed to include all such embodiments and equivalent variations.

What is claimed is:

1. An isolated nucleic acid comprising a first nucleotide sequence encoding the polypeptide of SEQ ID No. 2, wherein the nucleotide sequence encoding Arg142 of SEQ ID No. 2 is CGC.

2. The isolated nucleic acid of claim 1, wherein the first nucleotide sequence encodes a polypeptide selected from the group consisting of: SEQ ID No. 3, SEQ ID No. 4, SEQ ID No. 5, SEQ ID No. 6, SEQ ID No. 7, SEQ ID No. 8, and SEQ ID No. 9.

3. The isolated nucleic acid according to claim 2, wherein the first nucleotide sequence encodes the polypeptide SEQ ID NO: 3.

4. The isolated nucleic acid according to claim 3, wherein the first nucleotide sequence consists of SEQ ID NO: 19.

5. The isolated nucleic acid of claim 1, further comprising a second nucleotide sequence encoding a reporter polypeptide, wherein the first nucleotide sequence is operably linked to the second nucleotide sequence.

6. The isolated nucleic acid of claim 1, further comprising a nucleotide sequence encoding a 5' untranslated region of a mRNA encoding a spermidine/spermine acetyltransferase operably linked 5' to the first nucleotide sequence, wherein the 5' untranslated region comprises a Kozak sequence and does not comprise an open reading frame.

7. The isolated nucleic acid of claim 6, wherein the nucleotide sequence encoding the 5' untranslated region comprises nucleotides 1 to 66 of SEQ ID No. 20 or nucleotides 1 to 155 of SEQ ID No. 21.

8. The isolated nucleic acid of claim 1, wherein the nucleic acid is RNA.

9. The isolated nucleic acid of claim 5, wherein the nucleic acid is RNA.

10. An isolated nucleic acid comprising a first nucleotide sequence encoding the amino acids 1-26 of SEQ ID No. 2 operably linked to a second nucleotide sequence encoding amino acids 134-171 of SEQ ID No. 2, wherein the nucleotide sequence encoding Arg142 of SEQ ID No. 2 is CGC.

11. A vector comprising an expression cassette wherein said expression cassette comprises the nucleic acid of claim 1.

12. The vector according to claim 11, wherein the first nucleic acid sequence encodes the polypeptide SEQ ID NO: 3.

13. The vector according to claim 12, wherein the first nucleic acid sequence consists of SEQ ID NO: 19.

14. A kit for testing candidate agents, the kit comprising an isolated nucleic acid of claim 1 or claim 10.

15. The kit according to claim 14, wherein the isolated nucleic acid comprises a first nucleotide sequence encoding the polypeptide SEQ ID NO: 3.

16. The kit according to claim 15, wherein the isolated nucleic acid comprises a first nucleotide sequence of the isolated nucleic acid consists of SEQ ID NO: 19.

17. A method for identifying an agent that increases translation of an mRNA encoding spermidine/spermine acetyltransferase comprising the steps of:
    translating an RNA in the absence of a candidate agent to provide a reference level of translation, wherein the RNA is a nucleic acid comprising a first nucleotide sequence encoding the polypeptide of SEQ ID No. 2, wherein the nucleotide sequence encoding Arg142 of SEQ ID No. 2 is CGC,
    translating the RNA in the presence of the candidate agent to obtain a test level of translation,
    comparing the test level of translation with the reference level of translation, wherein the candidate agent is identified as an agent that increases translation if the test level of translation is greater than the reference level of translation.

18. The method of claim 17, wherein the RNA further comprises a second nucleotide sequence encoding a reporter polypeptide, wherein the first nucleotide sequence is operably linked to the second nucleotide sequence.

19. The method of claim 18, wherein the reporter polypeptide is selected from the group consisting of luciferase and green fluorescent protein.

20. The method of claim 17, wherein comparing the level of translation comprises a cell-based assay.

21. A method for identifying an agent that decreases translation of an mRNA encoding spermidine/spermine acetyltransferase comprising the steps of:
    translating an RNA in the absence of a candidate agent to provide a reference level of translation, wherein the RNA is a nucleic acid comprising a first nucleotide sequence encoding the polypeptide of SEQ ID No. 2, wherein the nucleotide sequence encoding Arg142 of SEQ ID No. 2 is CGC,
    translating the RNA in the presence of the candidate agent to obtain a test level of translation,
    comparing the test level of translation with the reference level of translation, wherein the candidate agent is identified as an agent that decreases translation if the test level of translation is less than the reference level of translation.

22. The method according to claim 21, wherein the first nucleotide sequence encodes the polypeptide SEQ ID NO: 3.

23. The method according to claim 22, wherein the first nucleotide sequence consists of SEQ ID NO: 19.

24. The method of claim 21, wherein the RNA further comprises a second nucleotide sequence encoding a reporter polypeptide, wherein the first nucleotide sequence is operably linked to the second nucleotide sequence.

25. The method of claim 24, wherein the reporter polypeptide is selected from the group consisting of luciferase and green fluorescent protein.

26. The method of claim 21, wherein comparing the level of translation is comprises a cell-based assay.

27. A method of increasing the amount of SSAT polypeptide in a cell comprising administering to a cell a vector comprising an expression cassette wherein said expression cassette comprises the nucleic acid of claim 1, wherein expression of said nucleic acid increases the amount of SSAT polypeptide in the cell.

28. The method according to claim 27, wherein the nucleotide sequence encodes the polypeptide SEQ ID NO: 3.

29. The method according to claim 28, wherein the first nucleotide sequence consists of SEQ ID NO: 19.

30. The method of claim 27, wherein the cell is a cell of a cellular proliferative disorder or disease.

31. The method of claim 27, wherein the cell is a human cell.

32. The method of claim 30, wherein the cell is a melanoma cell or a prostate carcinoma cell.

33. The isolated nucleic acid according to claim 10, wherein the first nucleotide sequence consists of nucleotides 1-78 of SEQ ID NO: 19, and the second nucleotide sequence consists of nucleotides 400-513 of SEQ ID NO: 19.

34. An isolated nucleic acid comprising a first nucleotide sequence consisting of nucleotides 1-222 of SEQ ID NO: 19 operably linked to a second nucleotide sequence consisting of nucleotides 400-513 of SEQ ID NO: 19.

35. The kit according to claim 14, wherein the isolated nucleic acid comprises the first nucleotide sequence consisting of nucleotides 1-78 of SEQ ID NO: 19 operably linked to a second nucleotide sequence consisting of nucleotides 400-513 of SEQ ID NO: 19.

\* \* \* \* \*